(12) United States Patent
Ji et al.

(10) Patent No.: US 7,872,017 B2
(45) Date of Patent: Jan. 18, 2011

(54) FUSED BICYCLOHETEROCYCLE SUBSTITUTED AZABICYCLIC ALKANE DERIVATIVES

(75) Inventors: Jianguo Ji, Libertyville, IL (US); Tao Li, Grayslake, IL (US); Christopher L. Lynch, Trevor, WI (US); Murali Gopalakrishnan, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/748,527

(22) Filed: May 15, 2007

(65) Prior Publication Data

US 2008/0045539 A1 Feb. 21, 2008

Related U.S. Application Data

(60) Provisional application No. 60/802,195, filed on May 19, 2006.

(51) Int. Cl.
*A61K 31/439* (2006.01)
*C07D 451/06* (2006.01)
*C07D 519/00* (2006.01)
*A61P 25/28* (2006.01)
*A61P 29/00* (2006.01)
*C07D 241/18* (2006.01)
*C07D 295/02* (2006.01)
*C07D 333/54* (2006.01)
*C07D 409/14* (2006.01)
*C07D 451/02* (2006.01)
*C07F 5/02* (2006.01)

(52) U.S. Cl. ............ 514/300; 544/238; 544/405; 544/409; 546/113; 546/129; 546/127; 546/126; 548/110; 548/405; 549/4; 568/6; 514/304

(58) Field of Classification Search ............ 514/299, 514/304; 546/112, 183, 125, 113, 129, 127, 546/126; 544/238, 405, 409
See application file for complete search history.

(56) References Cited

U.S. PATENT DOCUMENTS

| | | | |
|---|---|---|---|
| 4,921,860 A | 5/1990 | Cliffe | |
| 4,929,625 A | 5/1990 | Cliffe | |
| 5,461,053 A | 10/1995 | Boigegrain et al. | |
| 2004/0138286 A1 | 7/2004 | Imazaki et al. | |
| 2006/0258691 A1 | 11/2006 | Barbosa et al. | |
| 2007/0054912 A1 | 3/2007 | Astles et al. | |
| 2007/0185156 A1 | 8/2007 | Napier et al. | |
| 2009/0192186 A1 | 7/2009 | Ji et al. | |

FOREIGN PATENT DOCUMENTS

| | | |
|---|---|---|
| EP | 149088 | 7/1985 |
| EP | 1707202 | 3/2006 |
| JP | 2000-26408 | 2/2000 |
| WO | 9315052 | 8/1993 |
| WO | 9534561 | 12/1995 |
| WO | 9709311 | 3/1997 |
| WO | 0044755 | 8/2000 |
| WO | 0134604 | 5/2001 |
| WO | 0244182 | 6/2002 |
| WO | 02/058695 | 8/2002 |
| WO | 02076440 | 10/2002 |
| WO | 03/062235 | 7/2003 |
| WO | 03/106452 | 12/2003 |
| WO | 2004052888 | 6/2004 |
| WO | 2004/113334 | 12/2004 |
| WO | 2004110990 | 12/2004 |
| WO | 2005030140 | 4/2005 |
| WO | 2005037269 | 4/2005 |
| WO | 2005061457 | 7/2005 |
| WO | 2006030925 | 3/2006 |
| WO | 2006075004 | 7/2006 |
| WO | 2006076317 | 7/2006 |
| WO | 2006091963 | 8/2006 |
| WO | 2006101745 | 9/2006 |
| WO | 2006103277 | 10/2006 |
| WO | 2006108059 | 10/2006 |
| WO | 2007053435 | 5/2007 |
| WO | 2007063071 | 6/2007 |
| WO | WO/2007/063071 | * 6/2007 |

OTHER PUBLICATIONS

Becker, D.P., et al., "A Short Synthesis of 1-Azaadamantan-4-one and the 4r and 4s Isomers of 4-Amino-1-azaadamantane", Synthesis, pp. 1080-1082, (1992).
Stereochemistry of Organic Compounds, E.L. Eliel, S.H. Wilen; John Wiley and Sons, Inc., "Table of Contents", (1994).
Furniss, B.S., et al., "Practical Organic Chemistry", 5th Ed., Longman Scientific & Technical & John Wiley & Sons, Inc., "Table of Contents", (1989).
Levin, E.D., "Nicotinic Receptor Subtypes and Cognitive Function", J Neurobiology, vol. 53, pp. 633-640, (2002).
Paterson, D., et al., "Neuronal nicotinic receptors in the human brain", Progress in Neurobiology, vol. 61, pp. 75-111, (2000).
Adler et al., Schizophrenia Bull. 24: 189-202 (1998).
Cordero-Erausquin et al., PNAS 98: 2803-2807 (2001).
Friedman et al., Biol. Psychiatry 51: 349-357 (2002).
Heeschen et al., J. Clin. Invest. 110: 527-536 (2002).
Heeschen et al., Nature Medicine 7: 833-839 (2001).
Jonnala et al., J. Neurosci. Res. 66: 565-572 (2001).
Kihara et al., J. Biol. Chem. 276: 13541-13546 (2001).
Leonard et al., Eur. J. Pharmacol. 393: 237-242 (2000).
Liu et al., PNAS 98: 4734-4739 (2001).
Rowley et al., J. Med. Chem. 44: 477-501 (2001).
Shimohama et al., Brain Res. 779: 359-363 (1998).
Son et al., Biol. Reproduct. 68: 1348-1353 (2003).
Stevens et al., Psychopharmacology 136: 320-327 (1998).
Wang et al., Nature 421: 384-388 (2003).
PCT International Search Report, PCT/US2007/068930, mailed May 28, 2008.

* cited by examiner

*Primary Examiner*—James O Wilson
*Assistant Examiner*—Cecilia M Jaisle
(74) *Attorney, Agent, or Firm*—Antonia M. Holland

(57) ABSTRACT

The invention relates to fused bicycloheterocycle substituted azabicyclic alkane derivatives, compositions comprising such compounds, and methods of treating conditions and disorders using such compounds and compositions.

14 Claims, No Drawings

FUSED BICYCLOHETEROCYCLE SUBSTITUTED AZABICYCLIC ALKANE DERIVATIVES

RELATED APPLICATION INFORMATION

This application claims priority to U.S. Application No. 60/802,195 filed on May 19, 2006, the contents of which are herein incorporated by reference.

TECHNICAL FIELD

The invention relates to fused bicycloheterocycle substituted azabicyclic alkane derivatives, compositions comprising such compounds, and methods of treating conditions and disorders using such compounds and compositions.

DESCRIPTION OF RELATED TECHNOLOGY

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins, $\alpha2$-$\alpha10$ and $\beta2$-$\beta4$, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha4)_2(\beta2)_3$ (the $\alpha4\beta2$ subtype), while another major population of receptors is comprised of homomeric $(\alpha7)_5$ (the $\alpha7$ subtype) receptors.

Certain compounds, like the plant alkaloid nicotine, interact with all subtypes of the nAChRs, accounting for the physiological effects of this compound. While nicotine has been demonstrated to have many biological activities, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The $\alpha7$ and $\alpha4\beta2$ nAChRs have been shown to play a significant role in enhancing cognitive function, including aspects of learning, memory and attention (Levin, E. D., J. Neurobiol. 53: 633-640, 2002). For example, $\alpha7$ nAChRs have been linked to conditions and disorders related to attention deficit disorder, attention deficit hyperactivity disorder (ADHD), Alzheimer's disease (AD), mild cognitive impairment, senile dementia, dementia associated with Lewy bodies, dementia associated with Down's syndrome, AIDS dementia, Pick's Disease, as well as cognitive deficits associated with schizophrenia, among other systemic activities. The $\alpha4\beta2$ receptor subtype is implicated in attention, cognition, schizophrenia, epilepsy, and pain control (Paterson and Norberg, *Progress in Neurobiology* 61 75-111, 2000).

The activity at both $\alpha7$ and $\alpha4\beta2$ nAChRs can be modified or regulated by the administration of subtype selective nAChR ligands. The ligands can exhibit antagonist, agonist, or partial agonist properties. Compounds that function as positive allosteric modulators are also known.

Although compounds that nonselectively demonstrate activity at a range of nicotinic receptor subtypes including the $\alpha4\beta2$ and $\alpha7$ nAChRs are known, it would be beneficial to provide compounds that interact selectively with $\alpha7$-containing neuronal nAChRs, $\alpha4\beta2$ nAChRs, or both $\alpha7$ and $\alpha4\beta2$ nAChRs compared to other subtypes.

SUMMARY OF THE INVENTION

The invention is directed to fused bicycloheterocycle substituted azabicyclic compounds as well as compositions comprising such compounds, and method of using the same.

One aspect of the present invention is directed toward a compound of formula (I)

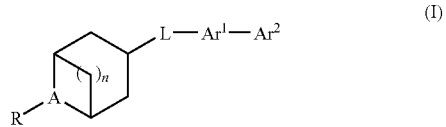

or a pharmaceutically acceptable salt, ester, amide, or prodrug thereof, wherein n is 1, 2 or 3;

A is N or $N^+$—$O^-$;

R is hydrogen, alkyl, cycloalkylalkyl and arylalkyl;

L is selected from the group consisting of O, S, and —N($R_a$)—;

$Ar^1$ is a 6-membered aryl or 6 membered heteroaryl ring;

$Ar^2$ is a bicyclic heteroaryl; and $R_a$ is selected from the group consisting of hydrogen, alkyl and alkylcarbonyl;

provided that if $Ar^1$ is

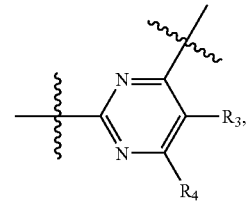

then L is O or S.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly $\alpha7$ nAChR activity.

Yet another aspect of the invention relates to a method of selectively modulating to nAChR activity, for example $\alpha7$ nAChR activity. The method is useful for treating and/or preventing conditions and disorders related to $\alpha7$ nAChR activity modulation in mammals. More particularly, the method is useful for conditions and disorders related to attention deficit disorder, attention deficit hyperactivity disorder (ADHD), Alzheimer's disease (AD), mild cognitive impairment, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, need for new blood vessel growth associated with wound healing, need for new blood vessel growth associated with vascularization of skin grafts, and lack of circulation, more particularly circulation around a vascular occlusion, among other systemic activities, for example inflammatory response mediated by TNF.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl", as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy", as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl", as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy", as used herein, means an alkyl group as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy", as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl", as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl", as used herein, means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxyimino", as used herein, means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl", as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl", as used herein, means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl", as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio", as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl", as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido", as used herein, means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl", as used herein, means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —$NR_gR_j$, ($NR_gR_j$)alkyl, ($NR_gR_j$)alkoxy, ($NR_gR_j$)carbonyl, and ($NR_gR_j$)sulfonyl, wherein $R_g$ and $R_j$ are each independently selected from the group consisting of hydrogen and alkyl.

The term "arylcarbonyl", as used herein, means an aryl group, as defined herein, or a benzyl group appended to the parent molecular moiety through a carbonyl group, represented by —C(O)—, as defined herein. Representative examples of arylcarbonyl include, but are not limited to, phenylcarbonyl and benzylcarbonyl.

The term "aryloxycarbonyl", as used herein, means an aryl-O— group, wherein the aryl of aryl-O— is as defined herein, or a benzoxyl group appended to the parent molecular moiety through a carbonyl group, represented by —C(O)—, as defined herein. Representative examples of aryloxycarbonyl include, but are not limited to, phenoxycarbonyl and benzyloxycarbonyl.

The term "arylsulfonyl", as used herein, means an aryl group, as defined herein, appended to the parent molecular moiety through a sulfonyl group, as defined herein. Representative examples of arylsulfonyl include, but are not limited to, phenylsulfonyl, (methylaminophenyl)sulfonyl, (dimethylaminophenyl)sulfonyl, and (naphthyl)sulfonyl.

The term "carbonyl", as used herein, means a —C(O)— group.

The term "carboxy", as used herein, means a —CO$_2$H group.

The term "cyano", as used herein, means a —CN group.

The term "formyl", as used herein, means a —C(O)H group.

The term "halo" or "halogen", as used herein, means —Cl, —Br, —I or —F.

The term "haloalkoxy", as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl", as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl" means an aromatic five- or six-membered ring containing 1, 2, 3, or 4 heteroatoms independently selected from group consisting of nitrogen, oxygen and sulfur. The heteroaryl groups are connected to the parent molecular moiety through a carbon or nitrogen atom. Representative examples of heteroaryl include, but are not limited to, furyl, imidazolyl, indazolyl, benzothiozolyl, isoxazolyl, isothiazolyl, oxadiazolyl, oxazolyl, pyrazinyl, pyrazolyl, pyridazinyl, pyridinyl, pyrimidinyl, pyrrolyl, tetrazolyl, thiadiazolyl, thiazolyl, thienyl, triazinyl, and triazolyl.

The heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_g$R$_j$, (NR$_g$R$_j$)alkyl, (NR$_g$R$_j$)alkoxy, (NR$_g$R$_j$)carbonyl, and (NR$_g$R$_j$)sulfonyl, wherein R$_g$ and R$_j$ are each independently selected from the group consisting of hydrogen and alkyl.

The term "bicyclic heteroaryl" refers to fused aromatic nine- and ten-membered bicyclic rings containing 1, 2, 3, or 4 heteroatoms independently selected from the group consisting of nitrogen, oxygen and sulfur. The bicyclic heteroaryl groups are connected to the parent molecular moiety through a carbon or nitrogen atom. Representative examples of bicyclic heteroaryl rings include, but are not limited to, indolyl, benzothiazolyl, benzofuranyl, isoquinolinyl, and quinolinyl. Bicyclic heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_g$R$_j$, (NR$_g$R$_j$)alkyl, (NR$_g$R$_j$)alkoxy, (NR$_g$R$_j$)carbonyl, and (NR$_g$R$_j$)sulfonyl, wherein R$_g$ and R$_j$ are each independently selected from the group consisting of hydrogen and alkyl.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of nitrogen, oxygen and sulfur. The 3 or 4 membered ring contains 1 heteroatom selected from the group consisting of nitrogen, oxygen and sulfur. The 5 membered ring contains zero or one double bond and one, two or three heteroatoms selected from the group consisting of nitrogen, oxygen and sulfur. The 6 or 7 membered ring contains zero, one or two double bonds and one, two or three heteroatoms selected from the group consisting of nitrogen, oxygen and sulfur. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle that is either fused to a cycloalkyl ring, a heteroaryl ring or another heterocyclic ring, or is formed by an alkyl chain attached to two non-adjacent carbons contained within the monocyclic heterocyclic ring. The bicyclic heterocycle is connected to the parent molecular moiety through any carbon atom or any nitrogen atom contained within the monocyclic heterocycle. Representative examples of bicyclic heterocycle include, but are not limited to, azabicyclo[3.1.1]heptane, azabicyclo[3.2.1]octane, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The heterocyclic groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_g$R$_j$, (NR$_g$R$_j$)alkyl, (NR$_g$R$_j$)alkoxy, (NR$_g$R$_j$)carbonyl, and (NR$_g$R$_j$)sulfonyl, wherein R$_g$ and R$_j$ are each independently selected from the group consisting of hydrogen and alkyl.

The term "hydroxy", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto", as used herein, means a —SH group.

The term "nitro", as used herein, means a —NO$_2$ group.

The term "—NR$_g$R$_j$", as used herein, means two groups, R$_g$ and R$_j$, which are appended to the parent molecular moiety through a nitrogen atom. R$_g$ and R$_j$ are each independently hydrogen or alkyl. Representative examples of —NR$_g$R$_j$ include, but are not limited to, amino, methylamino, dimethylamino, and methylethylamino.

The term "(NR$_g$R$_j$)alkyl", as used herein, means a —NR$_g$R$_j$ group, as defined herein, appended to the parent molecular moiety through an alkyl group, as defined herein. Representative examples of (NR$_g$R$_j$)alkyl include, but are not limited to, (amino)methyl, (dimethylamino)methyl, and (ethylamino)methyl.

The term "(NR$_g$R$_j$)alkoxy", as used herein, means a —NR$_g$R$_j$ group, as defined herein, appended to the parent molecular moiety through an alkoxy group, as defined herein. Representative examples of (NR$_g$R$_j$)alkoxy include, but are not limited to, (amino)methoxy, (dimethylamino)methoxy, and (diethylamino)ethoxy.

The term "(NR$_g$R$_j$)carbonyl", as used herein, means a —NR$_g$R$_j$ group, as defined herein, appended to the parent molecular moiety through a carbonyl group, as defined herein. Representative examples of (NR$_g$R$_j$)carbonyl include, but are not limited to, aminocarbonyl, (methylamino)carbonyl, (dimethylamino)carbonyl, and (ethylmethylamino)carbonyl.

The term "(NR$_g$R$_j$)sulfonyl", as used herein, means a —NR$_g$R$_j$ group, as defined herein, appended to the parent molecular moiety through a sulfonyl group, as defined herein. Representative examples of (NR$_g$R$_j$)sulfonyl include, but are not limited to, aminosulfonyl, (methylamino)sulfonyl, (dimethylamino)sulfonyl, and (ethylmethylamino)sulfonyl.

The term "sulfonyl", as used herein, means a —S(O)$_2$— group.

The term "thioalkoxy", as used herein, means an alkyl group, as defined herein, appended to the parent molecular moiety through a sulfur atom. Representative examples of thioalkoxy include, but are no limited to, methylthio, ethylthio, and propylthio.

Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric (α7)$_5$ receptors and α7* receptors, which denote a nAChR containing at least one α7 subunit.

Compounds of the Invention

Compounds of the invention have the formula (I) as described above. More particularly, compounds of formula (I) can include, but are not limited to, compounds wherein A is N, and n is 1 or 2. Certain preferred compounds exist wherein A is N; L is O; n is 2.

More particularly, in compounds of formula (I) Ar$^1$ is selected from:

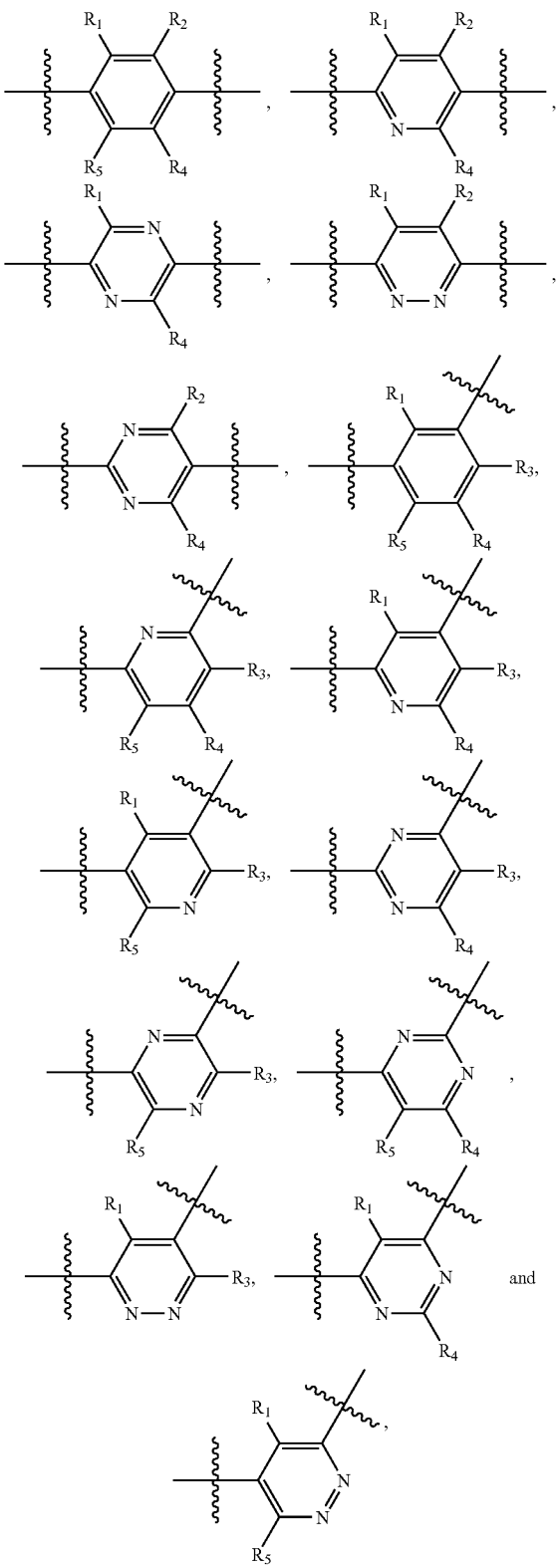

wherein R$_1$, R$_2$, R$_3$, R$_4$ and R$_5$ are independently acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —NR$_g$R$_j$, (NR$_g$R$_j$)alkyl, (NR$_g$R$_j$)alkoxy, (NR$_g$R$_j$)carbonyl, or (NR$_g$R$_j$)sulfonyl; R$_g$ and R$_j$ are each independently hydrogen or alkyl. More preferably, Ar$^1$ is

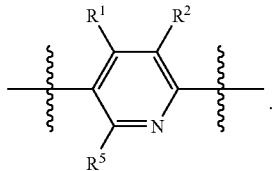

Particularly, the invention includes, but is not limited to, compounds of formula (I) wherein A is N; R is methyl; L is O; n is 2; Ar$^1$ is

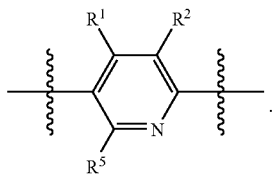

Ar$^2$ in compounds of formula (I) is selected from:

(i)

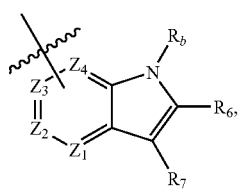

(ii)

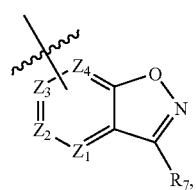

(iii)

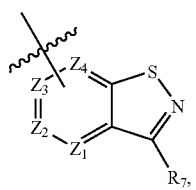

(iv)

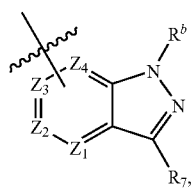

-continued (v)

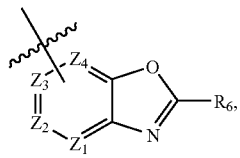

(vi)

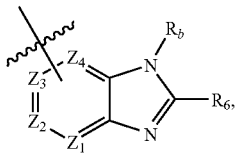

(vii)

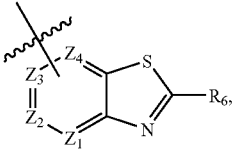

(viii)

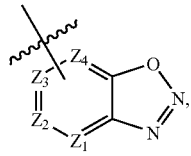

(ix)

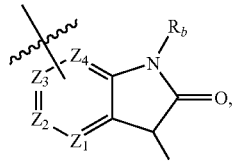

(x)

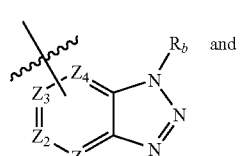

and (xi)

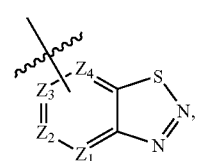

wherein Z$_1$, Z$_2$, Z$_3$ and Z$_4$ are each independently nitrogen or are carbon, wherein the carbon atom is optionally substituted with a substituent selected from the group consisting of hydrogen, halogen, alkyl, —OR$_c$, -alkyl-OR$_c$, —NR$_d$R$_e$, and -alkyl-NR$_d$R$_e$; R$_b$ is selected from the group consisting of hydrogen, alkyl and alkylcarbonyl; R$_c$ is alkyl; R$_d$ and R$_e$ are each independently selected from the group consisting of hydrogen and alkyl, R$_6$ and R$_7$ are each independently selected from the group consisting of hydrogen, alkenyl, alkoxy, alkoxyalkoxy, alkoxyalkyl, alkoxycarbonyl, alkoxyimino, alkoxysulfonyl, alkyl, alkylcarbonyl, alkylcarbonyloxy, alkylsulfonyl, alkynyl, carboxy, cyano, formyl, haloalkoxy, haloalkyl, halo, hydrogen, hydroxy, hydroxyalkyl, mercapto, nitro, thioalkoxy, —NR$_g$R$_j$, (NR$_g$R$_j$)alkyl, (NR$_g$R$_j$)alkoxy, (NR$_g$R$_j$)carbonyl, and (NR$_g$R$_j$)sulfonyl; R$_g$ and R$_j$ are each independently selected from the group consisting of hydrogen and alkyl.

R is selected from hydrogen, alkyl, cycloalkylalkyl, and arylalky. Preferred compounds are disclosed wherein R is hydrogen and alkyl. Preferably, R is methyl and hydrogen.

Preferred compounds are disclosed wherein $Ar^2$ is

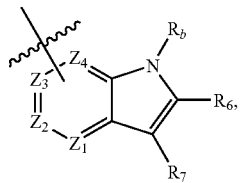
(i)

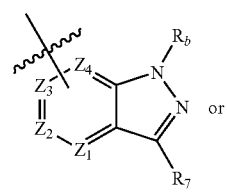
(iv)

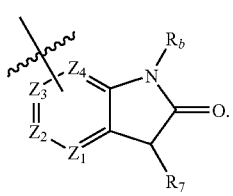
(ix)

More preferably $Ar^2$ is

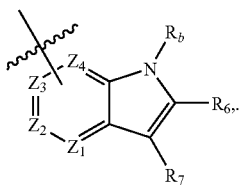
(i)

Particularly, the invention relates to compounds of formula (I) wherein A is N; R is selected from methyl and hydrogen; L is O; n is 2; and $Ar^2$ is selected from the group of consisting of:

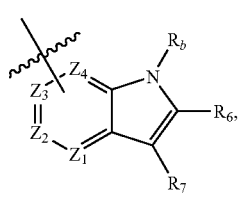
(i)

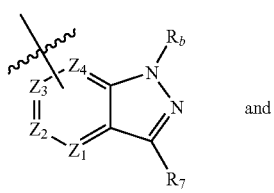
(iv)
and

-continued

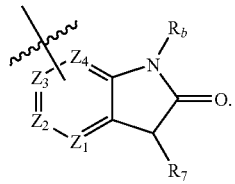
(ix)

More particularly, the invention relates to compounds of formula (I) wherein A is N; R is methyl or hydrogen; L is O; n is 2; $Ar^1$ is

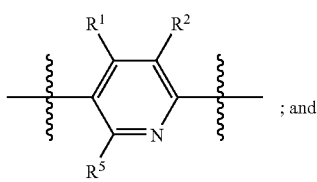
; and

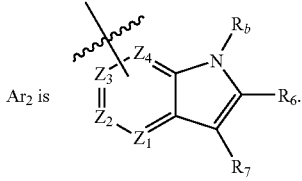
(i)

$Ar_2$ is

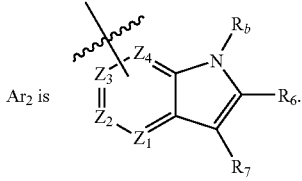

Compounds for the method of the invention, including but not limited to those specified in the examples or otherwise specifically named, can modulate, and often possess an affinity for, nAChRs, and more particularly α7 nAChRs. As α7 nAChRs ligands, the compounds of the invention can be useful for the treatment or prevention of a number of α7 nAChR-mediated diseases or conditions.

Specific examples of compounds that can be useful for the treatment or prevention of α7 nAChR-mediated diseases or conditions include, but are not limited to, compounds described in the Compounds of the Invention and also in the Examples, and also compounds such as:

5-{6-[(endo)-8-methyl-8-aza-bicyclo[3.2.1]oct-3-yloxy]-pyridazin-3-yl}-1H-indole;
(endo)-3-(6-benzo[b]thiophen-5-yl-pyridazin-3-yloxy)-8-methyl-8-aza-bicyclo[3.2.1]octane;
(endo)-3-[6-(benzofuran-5-yl)-pyridazin-3-yloxy]-8-methyl-8-aza-bicyclo[3.2.1]octane;
6-{6-[(endo)-8-methyl-8-aza-bicyclo[3.2.1]oct-3-yloxy]-pyridazin-3-yl}-1H-indole;
5-{6-[(endo)-8-methyl-8-aza-bicyclo[3.2.1]oct-3-yloxy]-pyridazin-3-yl}-1H-indazole;
1-methyl-5-{6-[(endo)-8-methyl-8-aza-bicyclo[3.2.1]oct-3-yloxy]-pyridazin-3-yl}-1H-indole;
5-{6-[(endo)-8-methyl-8-aza-bicyclo[3.2.1]oct-3-yloxy]-pyridazin-3-yl}-2-trifluoromethyl-1H-indole;
5-{6-[(exo)-8-methyl-8-aza-bicyclo[3.2.1]oct-3-yloxy]-pyridazin-3-yl}-1H-indole;
5-{5-[(endo)-8-methyl-8-aza-bicyclo[3.2.1]oct-3-yloxy]-pyridin-2-yl}-1H-indole;
(endo)-3-(6-benzo[b]thiophen-5-yl-pyridin-3-yloxy)-8-methyl-8-aza-bicyclo[3.2.1]octane;
5-{5-[(exo)-8-methyl-8-aza-bicyclo[3.2.1]oct-3-yloxy]-pyridin-2-yl}-1H-indole;

(exo)-3-[6-(benzofuran-5-yl)-pyridin-3-yloxy]-8-methyl-8-aza-bicyclo[3.2.1]octane;
5-{5-[(exo)-8-methyl-8-aza-bicyclo[3.2.1]oct-3-yloxy]-pyridin-2-yl}-1H-indazole;
5-{5-[(exo)-8-methyl-8-aza-bicyclo[3.2.1]oct-3-yloxy]-pyridin-2-yl}-2-trifluoromethyl-1H-indole;
4-{5-[(exo)-8-methyl-8-aza-bicyclo[3.2.1]oct-3-yloxy]-pyridin-2-yl}-1H-indole;
5-{6-[(endo)-8-methyl-8-aza-bicyclo[3.2.1]oct-3-yloxy]-pyridin-3-yl}-1H-indole;
(endo)-3-(5-benzo[b]thiophen-5-yl-pyridin-2-yloxy)-8-methyl-8-aza-bicyclo[3.2.1]octane;
5-{6-[(exo)-8-methyl-8-aza-bicyclo[3.2.1]oct-3-yloxy]-pyridin-3-yl}-1H-indole;
[6-(1H-indol-5-yl)-pyridin-3-yl]-[(endo)-8-methyl-8-aza-bicyclo[3.2.1]oct-3-yl]-amine;
[6-(benzofuran-5-yl)-pyridin-3-yl]-[(endo)-8-methyl-8-aza-bicyclo[3.2.1]oct-3-yl]-amine;
[(endo)-8-methyl-8-aza-bicyclo[3.2.1]oct-3-yl]-[6-(2-trifluoromethyl-1H-indol-5-yl)-pyridin-3-yl]-amine;
[6-(1H-indazol-5-yl)-pyridin-3-yl]-[(endo)-8-methyl-8-aza-bicyclo[3.2.1]oct-3-yl]-amine;
[6-(1H-indol-4-yl)-pyridin-3-yl]-[(endo)-8-methyl-8-aza-bicyclo[3.2.1]oct-3-yl]-amine;
[(endo)-8-aza-bicyclo[3.2.1]oct-3-yl]-[6-(1H-indol-5-yl)-pyridin-3-yl]-amine;
[4-(1H-indol-5-yl)-phenyl]-[(endo)-8-methyl-8-aza-bicyclo[3.2.1]oct-3-yl]-amine;
[4-(1H-indazol-5-yl)-phenyl]-[(endo)-8-methyl-8-aza-bicyclo[3.2.1]oct-3-yl]-amine;
[(endo)-8-methyl-8-aza-bicyclo[3.2.1]oct-3-yl]-[4-(1-methyl-1H-indol-5-yl)-phenyl]-amine;
(4-benzo[b]thiophen-5-yl-phenyl)-[(endo)-8-methyl-8-aza-bicyclo[3.2.1]oct-3-yl]-amine;
[4-(benzofuran-5-yl)-phenyl]-[(endo)-8-methyl-8-aza-bicyclo[3.2.1]oct-3-yl]-amine;
[4-(1H-indol-4-yl)-phenyl]-[(endo)-8-methyl-8-aza-bicyclo[3.2.1]oct-3-yl]-amine;
[3-(1H-indol-5-yl)-phenyl]-[(endo)-8-methyl-8-aza-bicyclo[3.2.1]oct-3-yl]-amine;
[3-(1H-indol-4-yl)-phenyl]-[(endo)-8-methyl-8-aza-bicyclo[3.2.1]oct-3-yl]-amine;
5-{6-[(endo)-8-methyl-8-aza-bicyclo[3.2.1]oct-3-yloxy]-pyridazin-3-yl}-2-trifluoromethyl-1H-indole;
4-{6-[(exo)-8-methyl-8-aza-bicyclo[3.2.1]oct-3-yloxy]-pyridazin-3-yl}-1H-indole;
5-{6-[(exo)-8-methyl-8-aza-bicyclo[3.2.1]oct-3-yloxy]-pyridin-3-yl}-1H-indole;
5-{6-[(exo)-8-methyl-8-aza-bicyclo[3.2.1]oct-3-yloxy]-pyridin-3-yl}-2-trifluoromethyl-1H-indole;
4-{6-[(exo)-8-methyl-8-aza-bicyclo[3.2.1]oct-3-yloxy]-pyridazin-3-yl}-1H-indole;
6-{5-[(exo)-8-methyl-8-aza-bicyclo[3.2.1]oct-3-yloxy]-pyridin-2-yl}-1H-indole;
5-{5-[(endo)-8-methyl-8-aza-bicyclo[3.2.1]oct-3-yloxy]-pyrazin-2-yl}-1H-indole;
4-{5-[(endo)-8-methyl-8-aza-bicyclo[3.2.1]oct-3-yloxy]-pyrazin-2-yl}-1H-indole;
6-{5-[(endo)-8-methyl-8-aza-bicyclo[3.2.1]oct-3-yloxy]-pyrazin-2-yl}-1H-indole;
[6-(1H-indol-6-yl)-pyridin-3-yl]-[(endo)-8-methyl-8-aza-bicyclo[3.2.1]oct-3-yl]-amine;
5-{6-[(endo)-9-methyl-9-azabicyclo[3.3.1]nonan-3-yloxy]pyridazin-3-yl}-1H-indole;
(endo)-3-[6-(benzo[b]thiophen-5-yl)pyridazin-3-yloxy)-9-methyl-9-azabicyclo[3.3.1]nonane;
5-{5-[(endo)-8-methyl-8-aza-bicyclo[3.2.1]oct-3-yloxy]-pyrazin-2-yl}-1H-pyrrolo[2,3-b]pyridine;
5-{5-[(exo)-8-methyl-8-aza-bicyclo[3.2.1]oct-3-yloxy]-pyridin-2-yl}-1H-pyrrolo[2,3-b]pyridine;
5-{5-[(exo)-8-methyl-8-aza-bicyclo[3.2.1]oct-3-yloxy]-pyridin-3-yl}-1H-indole;
5-{5-[(exo)-8-methyl-8-aza-bicyclo[3.2.1]oct-3-yloxy]-pyrazin-2-yl}-1H-indole;
4-{5-[(exo)-8-methyl-8-aza-bicyclo[3.2.1]oct-3-yloxy]-pyrazin-2-yl}-1H-indole;
6-{5-[(exo)-8-methyl-8-aza-bicyclo[3.2.1]oct-3-yloxy]-pyrazin-2-yl}-1H-indole;
(endo)-N-(5-(1H-Indol-5-yl)pyridin-3-yl)-8-methyl-8-azabicyclo[3.2.1]octan-3-amine;
(endo)-N-(5-(1H-Indol-4-yl)pyridin-3-yl)-8-methyl-8-azabicyclo[3.2.1]octan-3-amine;
(endo)-N-(5-(1H-Indol-6-yl)pyridin-3-yl)-8-methyl-8-azabicyclo[3.2.1]octan-3-amine;
(endo)-N-{5-[2-(trifluoromethyl)-1H-indol-5-yl]pyridin-3-yl}-8-Methyl-8-azabicyclo[3.2.1]octan-3-amine;
5-{5-[(endo)-8-Methyl-8-azabicyclo[3.2.1]octan-3-yloxy]pyridin-2-yl}-1H-pyrrolo[2,3-b]pyridine;
5-{5-[(endo)-8-Methyl-8-azabicyclo[3.2.1]octan-3-yloxy]pyridin-2-yl}indolin-2-one;
5-{5-[(endo)-8-Azabicyclo[3.2.1]octan-3-yloxy]pyridin-2-yl}-1H-indole;
(1R,3r,5S,8s)-3-(6-(1H-Indol-5-yl)pyridin-3-yloxy)-8-methyl-8-azabicyclo[3.2.1]octane 8-oxide;
(1R,3r,5S,8r)-3-(6-(1H-Indol-5-yl)pyridin-3-yloxy)-8-methyl-8-azabicyclo[3.2.1]octane 8-oxide;
4-{5-[(endo)-8-Azabicyclo[3.2.1]octan-3-yloxy]pyridin-2-yl}-1H-indole;
5-{5-[(exo)-8-Azabicyclo[3.2.1]octan-3-yloxy]pyridin-2-yl}-1H-indole;
5-{5-[(endo)-8-Azabicyclo[3.2.1]octan-3-yloxy]pyridin-2-yl}indolin-2-one;
5-{5-[(endo)-8-Azabicyclo[3.2.1]octan-3-yloxy]pyridin-2-yl}-1H-pyrrolo[2,3-b]pyridine;
5-{5-[(exo)-8-Azabicyclo[3.2.1]octan-3-yloxy]pyridin-2-yl}-1H-pyrrolo[2,3-b]pyridine, or pharmaceutically acceptable salts, esters, amides, and prodrugs thereof.

Compound names are assigned by using AutoNom naming software, which is provided by MDL Information Systems GmbH (formerly known as Beilstein Informationssysteme) of Frankfurt, Germany, and is part of the CHEMDRAW® ULTRA v. 6.0.2 software suite.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30.

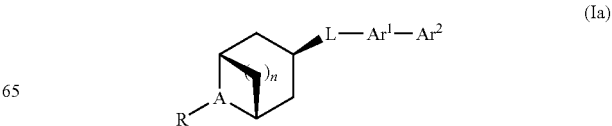
(Ia)

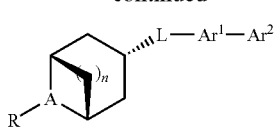
(Ib)

The attachment of L to the azabicyclic alkane may be considered to encompass both the endo and exo geometries, such as isomer (Ia) and (Ib). The configurational assignment of structures of formula (Ia) are assigned endo in accordance with that described in Stereochemistry of Organic Compounds, E. L. Eliel, S. H Wilen; John Wiley and Sons, Inc. 1994. Structures of formula (Ib) are assigned exo using the same methods.

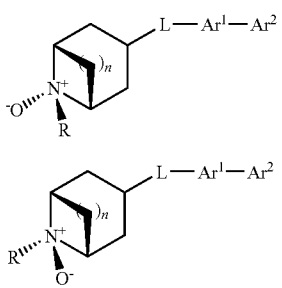

The N$^+$—O$^-$ portion of isomer (Ic) and isomer (Id) are diastereomers. The configurational assignment of structures of formula (Ic) are assigned (r) in accordance with that described in Synthesis, 1992, 1080, Becker, D. P.; Flynn, D. L. and as defined in Stereochemistry of Organic Compounds, E. L. Eliel, S. H Wilen; John Wiley and Sons, Inc. 1994. In addition the configurational assignment of structures of formula (Id) are assigned (s) using the same methods.

The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

The reactions exemplified in the schemes are performed in a solvent appropriate to the reagents and materials employed and suitable for the transformations being effected. The described transformations may require modifying the order of the synthetic steps or selecting one particular process scheme over another in order to obtain a desired compound of the invention, depending on the functionality present on the molecule.

The methods described below can entail use of various enantiomers. Where the stereochemistry is shown in the Schemes, it is intended for illustrative purposes only.

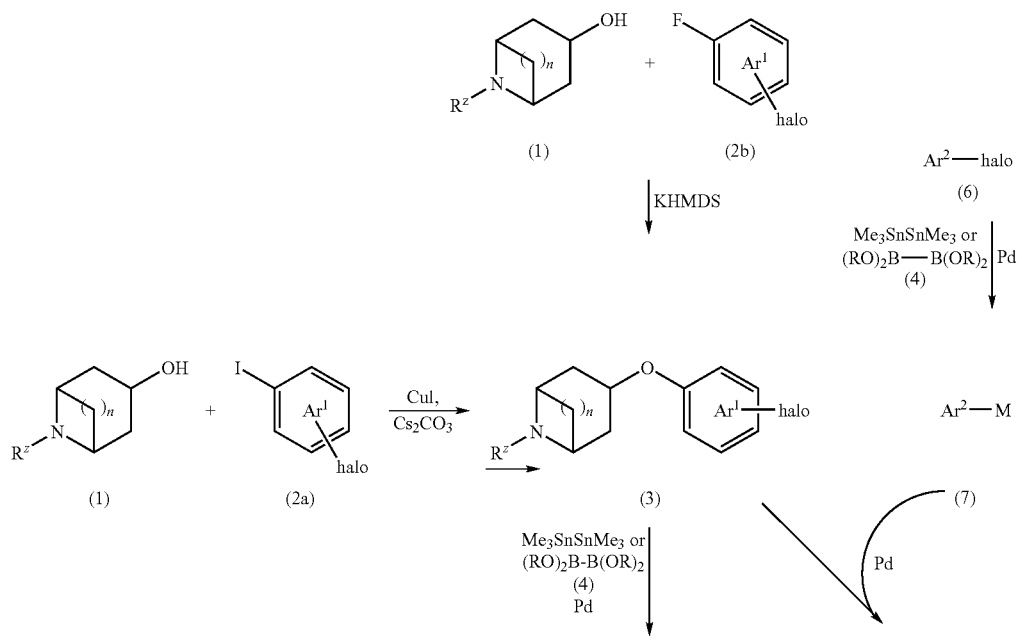

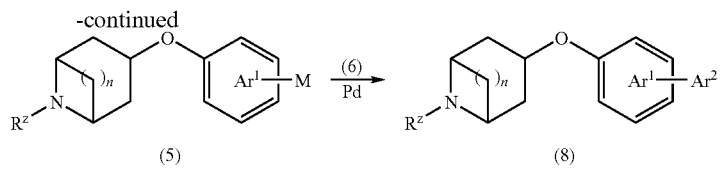

Compounds of formula (8), wherein $Ar^1$, $Ar^2$ are as defined in formula (I), can be prepared as described in Scheme 1.

formula (3) in the presence of a palladium catalyst will provide a compound of formula (8).

Scheme 2

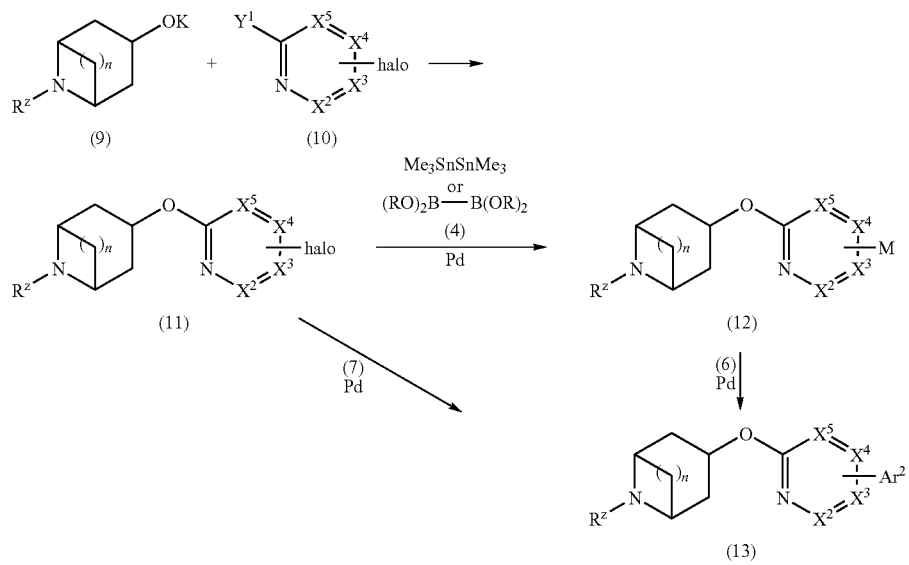

Compounds of formula (1) when treated with a compound of formula (2a), wherein halo is bromide, chloride, or iodide, in the presence of CuI, 1,10-phenanthroline and $Cs_2CO_3$ in a solvent such as, but not limited to, toluene as described in Org. Lett., 2002, 4, 973, will provide compounds of formula (3). Compounds of formula (3) can also be prepared through the reaction of compounds of formula (1) with compounds of formula (2b) in the presence of a base, such as, but not limited to, KHMDS, in a solvent such as but not limited to THF, DME and toluene. Compounds of formula (3) when treated with hexamethylditin or an organo-borane compound of formula (4), such as bis(pinacolato)diboron or bis(catecholato)diboron, wherein R is hydrogen, alkyl or aryl, in the presence of a palladium catalyst will provide the corresponding tin or boronic acid of formula (5), wherein M is $-Sn-(Me)_3$ or $-B(OR)_2$. Compounds of formula (5) when treated with compounds of formula (6), $Ar^2$-halo, wherein $Ar^2$ is a bicyclic heteroaryl ring and halo is bromide, chloride, or iodide, in the presence of a palladium catalyst to provide compounds of formula (8). Alternatively, compounds of formula (6) when treated with hexamethylditin or a di-borane containing compound of formula (4), such as bis(pinacolato)diboron and bis(catecholato)diboron, in the presence of a palladium catalyst will provide a corresponding tin or boronic acid containing compound of formula (7), wherein $Ar^2$ is a bicyclic heteroaryl and wherein M is $-Sn-(Me)_3$ or $-B(OR)_2$. Compounds of formula (7) when treated with a compound of formula (3) in the presence of a palladium catalyst will provide a compound of formula (8).

Compounds of formula (13), wherein $Ar^1$ is a nitrogen-containing heteroaryl, for examples pyridazine, pyrimidine, pyrazine, 2-pyridyl, and $Ar^2$ is as defined for formula (1), can be prepared as shown in Scheme 2. Compounds of formula (9), wherein $R^z$ is alkoxyalkyl, alkyl, alkyloxycarbonyl, alkylcarbonyl, aryl, arylalkyloxycarbonyl, cycloalkylalkyl, arylcarbonyl and aryloxycarbonyl and K represents the potassium, which are prepared from treating hydroxyl containing heterocycles of similar formula with potassium tert-butoxide in solvents such as but not limited to THF or DMF to provide the potassium oxide containing compounds of formula (9). The compounds of formula (9) when treated with compounds of formula (10), wherein $Y^1$ and halo are both bromo, chloro and iodo, and $X^2$, $X^3$, $X^4$ and $X^5$ are independently either carbon or nitrogen, for example, dichloropyridazine, will provide compounds of formula (11). Compounds of formula (11) when treated with hexamethylditin or a di-borane containing compound of formula (4) in the presence of a palladium catalyst according to the procedure outlined in Scheme 1 will provide compounds of formula (12). Compounds of formula (12) treated with compounds of formula 6 in the presence of a palladium catalyst will provide compounds of formula (13). Alternatively, the compounds of formula (11) when treated with organo stannane or organo boronic acid containing compounds of formula (7), as described in Scheme 1, in the presence of a palladium catalyst will provide a compound of formula (13).

Scheme 3

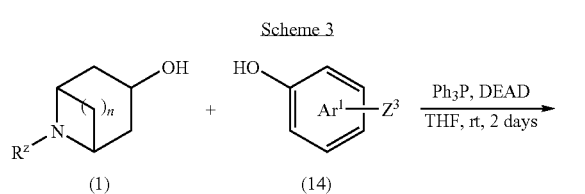

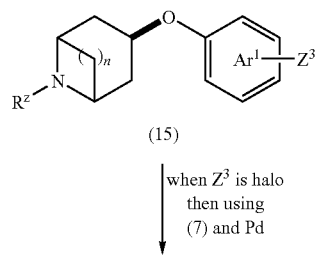

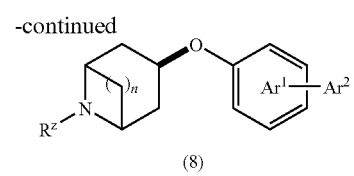

Alternatively, compounds of formula (8) may be prepared as outlined in Scheme 3. Compounds of formula (1) when treated with a compound of formula (14), wherein $Z^3$ is bromo, chloro or iodo or is $Ar^2$, in the presence of diethyl azodicarboxylate or di(isopropyl)l azodicarboxylate and a phosphine, such as triphenylphosphine, will provide compounds of formula (15). When $Z^3$ is $Ar^2$, compounds of formula (15) are representative of the present invention. When $Z^3$ is a halogen, the further treatment of the compound according to conditions outlined in Schemes 1-2 outlining the Suzuki type coupling to provide compounds of formula (8) which are representative of the compounds of the present invention.

Scheme 4

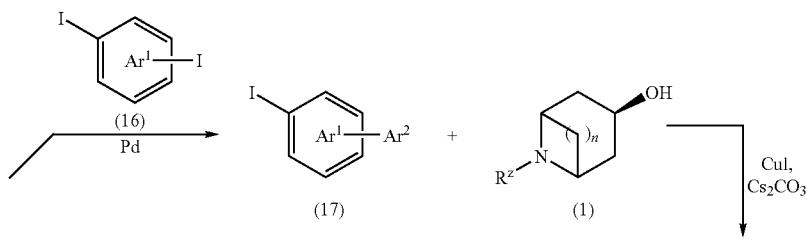

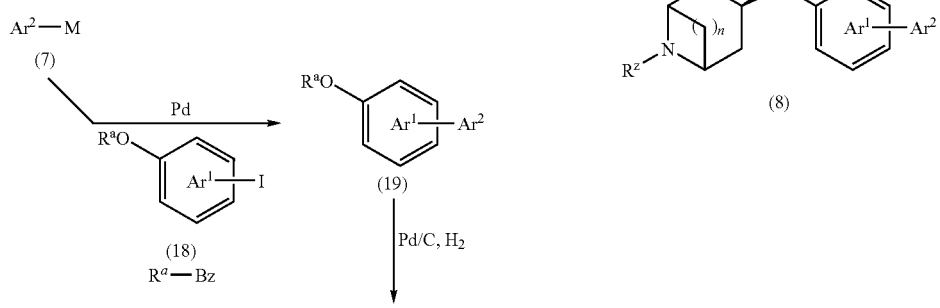

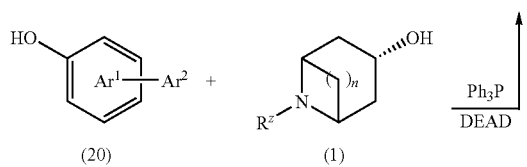

Another method of generating compounds of formula (8) is described in Scheme 4. The activated tin or boronic acid compounds of formula (7) can be coupled with a variety of aryl halides that will provide a method of generating biaryl compounds of formula (17) and of formula (20). For example compounds of formula (7) when treated with diiodobenzene of formula (16) in the presence of a palladium catalyst will provide compounds of formula (17). Compounds of formula (17) when treated with compounds of formula (1) in the presence of cuprous iodide and cesium carbonate and 1,10-phenanthroline as described in scheme 1, will provide compounds of formula (8). Alternatively, compounds of formula (7) when treated with a compound of formula (18), wherein $R^a$ is benzyl or another appropriate alcohol protecting group, in the presence of a palladium catalyst will provide compounds of formula (19). The deprotection of the alcohol protecting group, for example when $R^a$ is benzyl the deprotection is generally achieved utilizing palladium on carbon and an atmosphere of hydrogen, will provide compounds of formula (20). Compounds of formula (20) when treated with compounds of formula (1) in the presence of triphenylphosphine and diethyldiazocarboxylate or a similar reagent will provide compounds of formula (8).

Compounds of formula (25), which are representative of compounds of formula (1), wherein L is —NH—, can be prepared as shown in Scheme 5. Compounds of formula (21) when treated with compounds of formula (22), wherein halo is bromide, chloride, or iodide, along with sodium triacetoxy borohydride and $Na_2SO_4$ in acetic acid will provide compounds of formula (23). Alternatively, a compound of formula (23) can be obtained by treating compounds of formula (24) with a compound of formula (2), wherein Y is bromo or iodo, in the presence of palladium catalyst, preferably in toluene. Compounds of formula (23) when further treated with a tin or diboron of formula (4), such as bis(pinacolato)diboron and bis(catecholato)diboron, under conditions described in Scheme 2, will provide the corresponding tin or boronic acid compounds of formula (26). Compounds of formula (26) when treated with a compound of formula (6) in the presence of a palladium catalyst, will provide the compound of formula (25). Alternatively, the compound of formula (23) when treated with a tin or boronic acid containing compound of formula (7) in the presence of a palladium catalyst will also provide compounds of formula (25).

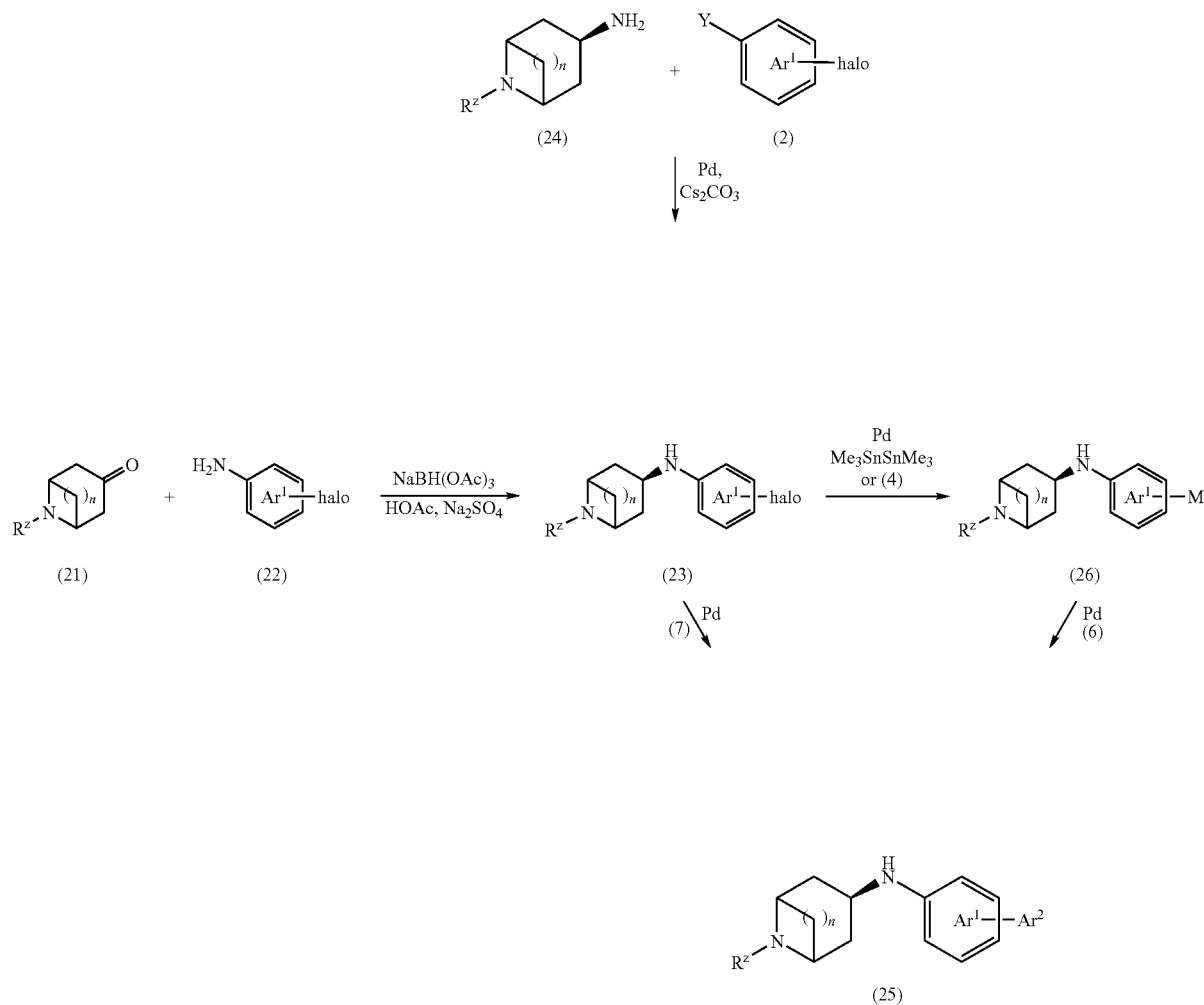

Scheme 6

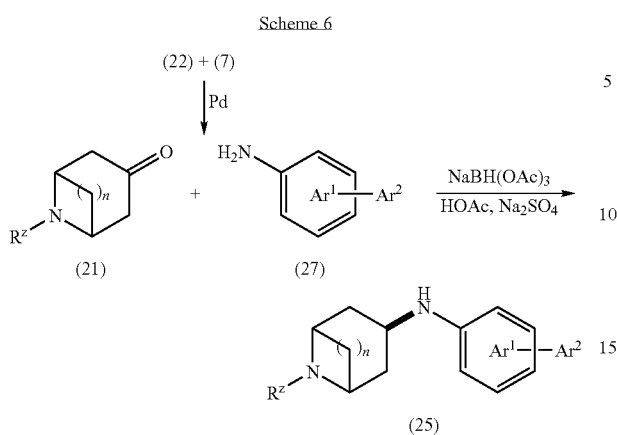

In addition, compounds of formula (25) can be prepared as shown in Scheme 6. Ketone containing compounds of formula (21), when treated with compounds of formula (27), prepared via the coupling reaction of haloarylamine of formula (22) and a suitable tin or boron agent of formula (7) in the presence of a palladium catalyst, followed by treatment with sodium triacetate borohydride and $Na_2SO_4$ in acetic acid will provide compounds of formula (25) as described in Tetrahedron Lett. 1996, 37, 6045.

Scheme 7

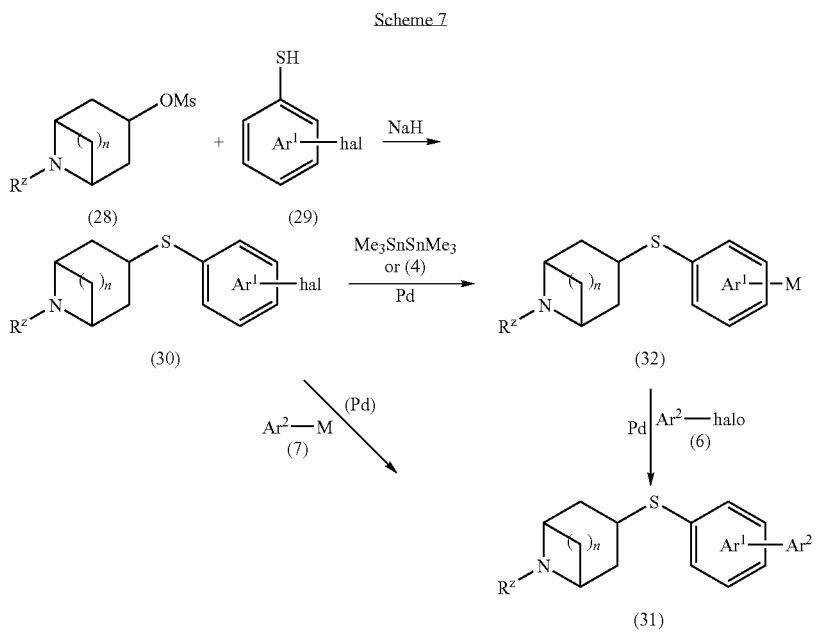

Compounds of formula (31), wherein L is S and $Ar^1$ and $Ar^2$ are as defined in formula (I), can be prepared as shown in Scheme 7. Compounds of formula (29), wherein halo is bromide, chloride, or iodide, when pretreated with sodium hydride in a solvent such as but not limited to DMF followed by treatment with compounds of formula (28) will provide compounds of formula (30). Compounds of formula (30) when treated with a compound of formula (7) as described in Scheme 1, will provide compounds of formula (31), which are representative of compounds of formula (I) wherein L is S. Alternatively, the compound of formula (30) when treated with a hexamethylditin or diboron reagent of formula (4), such as bis(pinacolato)diboron and bis(catecholato)diboron, in the presence of a palladium catalyst will provide a compound of formula (32). Compounds of formula (32) when treated with compounds of formula (6), wherein halo is bromo, chloro or iodo, in the presence of a palladium catalyst will provide compounds of formula (31).

Scheme 8

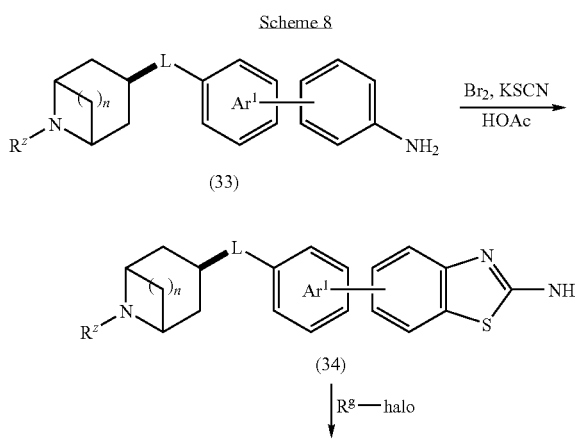

-continued

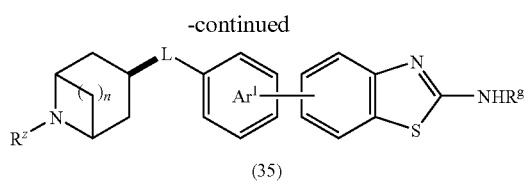

Compounds of formula (35) which are representative of compounds of formula (I), wherein L is O, S, or —N(R$_a$)—, Ar$^1$ is as previously defined in formula (I), and Ar$^2$ is an aminosubstituted benzothiazole are prepared according to the conditions outlined in Scheme 8. Compounds of formula (33) which are obtained by methods described in Schemes 1-7, wherein Ar$^2$ is substituted with —NH$_2$, when treated with bromine and KSCN in acetic acid will provide compounds of formula (34). Compounds of formula (34) can be further treated with the halide of a desired R$^g$ group, wherein R$^g$ is as defined under the scope compounds of the present invention to provide compounds of formula (35).

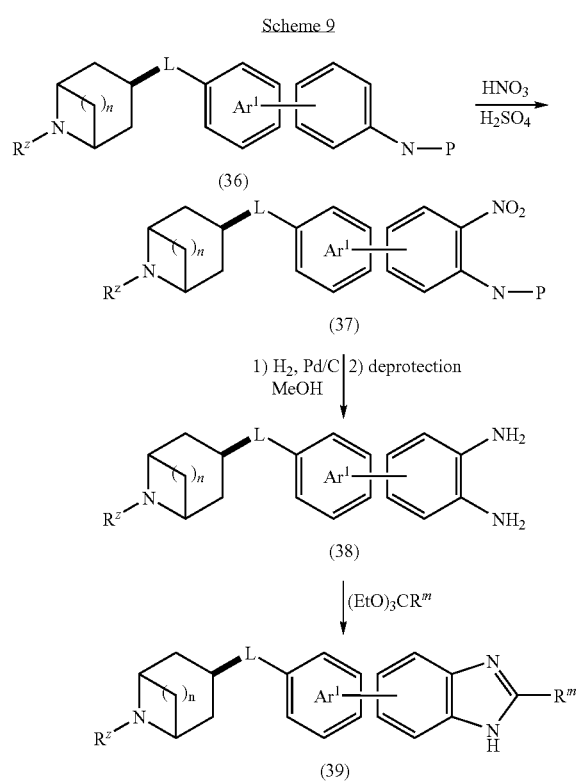

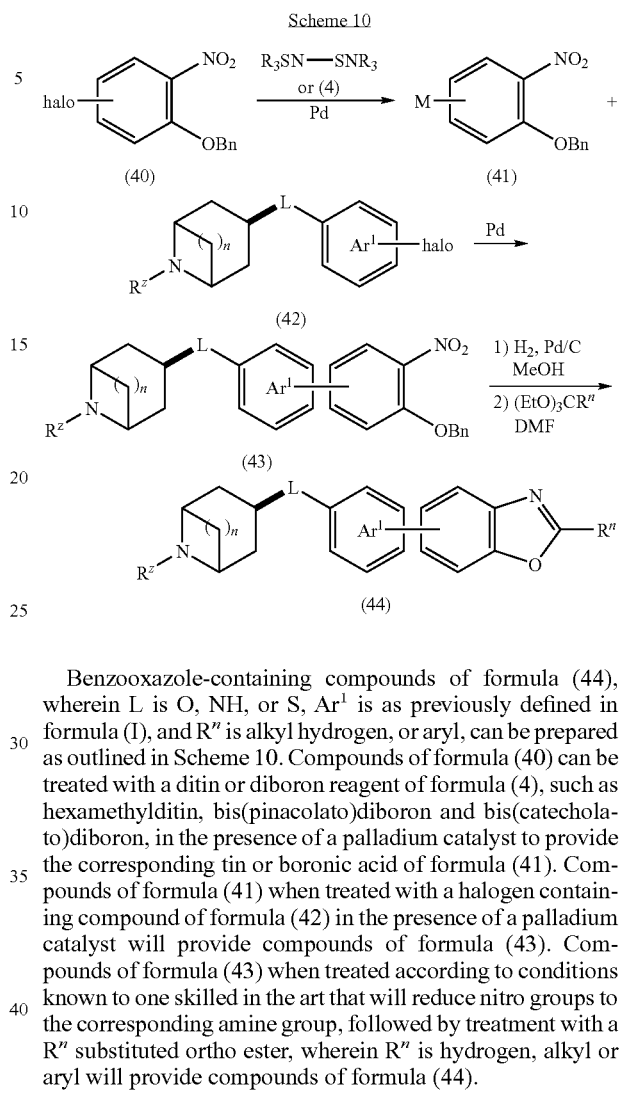

Compounds of formula (39), wherein L is O, NH, or S; Ar$^1$ is as previously defined in formula (I), Ar$^2$ is a benzoimidazole as defined for compounds of formula (I), are prepared as outlined in Scheme 9. Compounds of formula (36), are obtained by treating compounds of formula (33) of Scheme 8, using conditions known to one skilled in the art that will incorporate a nitrogen-protecting group to the nitrogen atom of Ar$^2$ wherein P is tert-butyloxycarbonyl, benzyloxycarbonyl, alkoxycarbonyl, alkylcarbonyl, arylcarbonyl or trialkylsilane. Compounds of formula (36) when treated with nitric acid in sulfuric acid will provide compounds of formula (37). Compounds of formula (37) when subjected to reducing conditions such as but not limited to treatment with a palladium catalyst and an atmosphere of hydrogen will reduce the nitro group to the corresponding amine, which is subjected to conditions known to one skilled in the art that will remove the nitrogen protecting group to provide compounds of formula (38). Compounds of formula (38) were then further subjected to treatment with an excess of an orthoester of formula (EtO)$_3$CR$^m$ will provide compounds of formula (39) wherein R$^m$ is alkyl or aryl.

Benzooxazole-containing compounds of formula (44), wherein L is O, NH, or S, Ar$^1$ is as previously defined in formula (I), and R″ is alkyl hydrogen, or aryl, can be prepared as outlined in Scheme 10. Compounds of formula (40) can be treated with a ditin or diboron reagent of formula (4), such as hexamethylditin, bis(pinacolato)diboron and bis(catecholato)diboron, in the presence of a palladium catalyst to provide the corresponding tin or boronic acid of formula (41). Compounds of formula (41) when treated with a halogen containing compound of formula (42) in the presence of a palladium catalyst will provide compounds of formula (43). Compounds of formula (43) when treated according to conditions known to one skilled in the art that will reduce nitro groups to the corresponding amine group, followed by treatment with a R″ substituted ortho ester, wherein R″ is hydrogen, alkyl or aryl will provide compounds of formula (44).

In addition, compounds of formula (I) wherein A is N can be converted to compounds of formula (I) wherein A is N$^+$—O$^-$ by treatment with an oxidizing agent. Examples of the oxidizing agent include, but not limited to, aqueous hydrogen peroxide and m-chloroperbenzoic acid. The reaction is generally performed in a solvent such as, but not limited to, acetonitrile, water, dichloromethane, acetone or mixture thereof, preferably a mixture of acetonitrile and water, at a temperature from about 0° C. to about 80° C., for a period of about 1 hour to about 4 days.

The compounds and intermediates of the invention may be isolated and purified by methods well known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group may be removed by treatment with an acid such as trifluoroacetic acid or hydrochloric acid. The Cbz and Bn protecting groups may be removed by catalytic hydrogenation. The acetyl and trifluoroacetyl protecting groups may be removed by a hydroxide ion.

The compounds and processes of the invention will be better understood by reference to the following Examples, which are intended as an illustration of and not a limitation upon the scope of the invention.

EXAMPLE 1

5-{6-[(endo)-8-Methyl-8-aza-bicyclo[3.2.1]oct-3-yloxy]-pyridazin-3-yl}-1H-indole trifluoroacetate

EXAMPLE 1A (endo)-3-(6-chloro-pyridazin-3-yloxy)-8-methyl-8-aza-bicyclo[3.2.1]octane A mixture of (endo)-tropine (Aldrich, 706 mg, 5.0 mmol), 3,6-dichloropyridazine (Aldrich, 745 mg, 5.0 mmol) and potassium t-butoxide (Aldrich, 1.12 g, 10 mmol) in THF (anhydrous, Aldrich, 25 mL) was stirred at 60° C. under an atmosphere of nitrogen for 16 hours. The mixture was concentrated under reduced pressure and the residue purified by chromatography (150 g SiO$_2$, EtOAc:MeOH:NH$_3$.H$_2$O, 90:10:1, R$_f$ 0.20) to provide the title compound. $^1$H NMR (300 MHz, CD$_3$OD) δ 2.03-2.36 (m, 8H), 2.45 (s, 3H), 3.38 [s (br.), 2H], 5.40 (t, J=5.09 Hz, 1H), 7.20 (d, J=9.16 Hz, 1H), 7.66 (d, J=9.16 Hz, 1H) ppm; MS (DCI/NH$_3$) m/z 254 (M+H)$^+$.

EXAMPLE 1B

5-{6-[(endo)-8-Methyl-8-aza-bicyclo[3.2.1]oct-3-yloxy]-pyridazin-3-yl}-1H-indole trifluoroacetate The mixture of Example 1A (112 mg, 0.44 mmol), 5-(4,4,5,5-tetramethyl-[1,3,2]dioxaborolan-2-yl)-1H-indole (Aldrich, 232 mg, 0.954 mmol), bis(triphenylphosphine)palladium(II) chloride (Aldrich, 7.02 mg, 0.01 mmol) and biphenyl-2-yl-dicyclohexyl-phosphane (Strem Chemicals, 10.5 mg, 0.03 mmol) in dioxane/EtOH/Na$_2$CO$_3$ (aq., 1 M) (v. 1/1/1, 3 mL) were heated and microwaved to 150° C. and 300 watts for 15 minutes in an Emry™ Creator microwave. The solid was filtered off with a syringe filter and the organic solution was directly purified by preparative HPLC (Gilson, column, Xterra® 5 µm, 40×100 mm. Eluting Solvent, MeCN/H$_2$O containing 0.1% v. TFA (90% to 10% over 25 minutes, Flow rate of 40 mL/minute, uv detector set to 254 nm). The fractions containing the desired product were collected and concentrated under reduced pressure and the residue was stirred in ether/ethanol (v. 10/1, 5 mL) at ambient temperature for 16 hours to provide the title compound. $^1$H NMR (300 MHz, CD$_3$OD) δ 2.31-2.60 (m, 8H), 2.85 (s, 3H), 3.97 [s (br.), 2H], 5.53-5.62 (m, 1H), 6.56 (d, J=3.05 Hz, 1H), 7.24-7.34 (m, 2H), 7.51 (d, J=8.48 Hz, 1H), 7.74 (dd, J=8.65, 1.86 Hz, 1H), 8.09-8.17 (m, 2H) ppm; MS (DCI/NH$_3$) m/z 335 (M+H)$^+$. Anal. Calculated for C$_{20}$H$_{22}$N$_4$O.1.05 CF$_3$CO$_2$H.0.50C$_2$H$_5$OH: C, 58.14; H, 5.50; N, 11.74. Found: C, 58.07; H, 5.44; N, 11.75.

EXAMPLE 2

(endo)-3-(6-Benzo[b]thiophen-5-yl-pyridazin-3-yloxy)-8-methyl-8-aza-bicyclo[3.2.1]octane trifluoroacetate The product from Example 1A (121 mg, 0.48 mmol) and 2-benzo[b]thiophen-5-yl-4,4,5,5-tetramethyl-[1,3,2]dioxaborolane (Maybridge, 219 mg, 0.84 mmol) were treated according to the procedure outlined in Example 1B to provide the title compound. $^1$H NMR (300 MHz, CD$_3$OD) δ 2.33-2.58 (m, 8H), 2.86 (s, 3H), 3.94-4.02 (m, 2H), 5.57-5.64 (m, 1H), 7.34 (d, J=9.15 Hz, 1H), 7.50 (d, J=5.42 Hz, 1H), 7.67 (d, J=5.42 Hz, 1H), 7.98 (dd, J=8.48, 1.70 Hz, 1H), 8.06 (d, J=8.48 Hz, 1H), 8.20 (d, J=9.15 Hz, 1H), 8.44 (d, J=1.36 Hz, 1H) ppm. MS (DCI/NH$_3$): m/z 352 (M+H)$^+$. Anal. Calculated for C$_{20}$H$_{21}$N$_3$OS.1.10 CF$_3$CO$_2$H: C, 55.91; H, 4.67; N, 8.81. Found: C, 55.90; H, 4.41; N, 8.59.

EXAMPLE 3

(endo)-3-[6-(Benzofuran-5-yl)-pyridazin-3-yloxy]-8-methyl-8-aza-bicyclo[3.2.1]octane trifluoroacetate The product from Example 1A (131 mg, 0.52 mmol) and 1-benzofuran-5-ylboronic acid (Apollo, 166 mg, 1.02 mol) were treated according to the procedure outlined in Example 1B to provide the title compound. $^1$H NMR (300 MHz, CD$_3$OD) δ 2.33-2.64 (m, 8H), 2.86 (s, 3H), 3.94-4.02 (m, 2H), 5.56-5.63 (m, 1H), 6.96 (d, J=1.36 Hz, 1H), 7.32 (d, J=9.16 Hz, 1H), 7.65 (d, J=8.82 Hz, 1H), 7.84 (d, J=2.37 Hz, 1H), 7.93 (dd, J=8.82, 2.03 Hz, 1H), 8.15 (d, J=9.49 Hz, 1H), 8.22 (d, J=1.36 Hz, 1H) ppm; MS (DCI/NH$_3$): m/z 336 (M+H)$^+$. Anal. Calculated for C$_{20}$H$_{21}$N$_3$O$_2$1.1CF$_3$CO$_2$H: C, 57.86; H, 4.83; N, 9.12. Found: C, 58.10; H, 4.54; N, 9.06.

EXAMPLE 4

6-{6-[(endo)-8-Methyl-8-aza-bicyclo[3.2.1]oct-3-yloxy]-pyridazin-3-yl}-1H-indole trifluoroacetate The product of Example 1A (158 mg, 0.62 mmol) was coupled with indole-6-boronic acid (Frontier, 162 mg, 1.01 mol) were treated according to the procedure outlined in Example 1B to provide the title compound. $^1$H NMR (300 MHz, CD$_3$OD) δ 2.33-2.59 (m, 8H), 2.85 (s, 3H), 3.93-4.01 (m, 2H), 5.58 (t, J=3.05 Hz, 1H), 6.51 (d, J=3.05 Hz, 1H), 7.29 (d, J=9.16 Hz, 1H), 7.35 (d, J=3.05 Hz, 1H), 7.58-7.64 (m, 1H), 7.66-7.73 (m, 1H), 8.01 (s, 1H), 8.13 (d, J=9.49 Hz, 1H) ppm. MS (DCI/NH$_3$): m/z 335 (M+H)$^+$. Anal. Calculated for $C_{20}H_{21}N_4O.1.10\ CF_3CO_2H$: C, 57.99; H, 5.06; N, 12.18. Found: C, 58.09; H, 4.95; N, 11.97.

EXAMPLE 5

5-{6-[(endo)-8-Methyl-8-aza-bicyclo[3.2.1]oct-3-yloxy]-pyridazin-3-yl}-1H-indazole fumarate

EXAMPLE 5A 5-(4,4,5,5-tetramethyl-1,3,2-dioxaborolan-2-yl)-1H-indazole

A flask containing 5-bromo-1H-indazole (Ref. US 2003199511, 9.45 g, 48 mmol) and bis(pinacolato)diboron (Aldrich, 15.5 g, 61 mmol) in dry DMF (160 mL) was added KOAc (16.7 g, 170 mmol). The mixture was degassed and purged with $N_2$ three times followed by the addition of $PdCl_2$ (dppf).$CH_2Cl_2$ (Aldrich, 985 mg, 1.21 mmol). The mixture was heated to 90° C. and stirred for 24 hours. The mixture was cooled to ambient temperature, diluted with ethyl acetate (250 mL), washed with water (2×50 mL). The organic phase was concentrated under reduced pressure and the residue was purified by chromatography (400 g $SiO_2$, hexane:EtOAc 90:10, $R_f$=0.6) to provide the title compound. $^1$H NMR (300 MHz, $CD_3OD$) δ 1.36 (s, 12H), 7.51 (dt, J=8.48, 1.02 Hz, 1H), 7.73 (dd, J=8.48, 1.02 Hz, 1H), 8.08 (d, J=1.02 Hz, 1H), 8.23 (t, J=1.02 Hz, 1H) ppm. MS (DCI/$NH_3$): m/z 245 (M+H)$^+$.

EXAMPLE 5B

5-{6-[(endo)-8-Methyl-8-aza-bicyclo[3.2.1]oct-3-yloxy]-pyridazin-3-yl}-1H-indazole A mixture of Example 1A (158 mg, 0.62 mmol) and the product of Example 5A (308 mg, 1.26 mol) were treated with bis(triphenylphosphine)palladium(II) chloride (Aldrich, 7.02 mg, 0.01 mmol) and biphenyl-2-yl-dicyclohexyl-phosphane (Strem Chemicals, 10.5 mg, 0.03 mmol) in dioxane/EtOH/$Na_2CO_3$ (aq., 1 M) (v. 1/1/1, 3 mL) were heated and microwaved to 150° C. and 300 watts for 15 minutes in an Emry™ Creator microwave reactor. The mixture was cooled to ambient temperature, solid was filtered off with a syringe filter and the organic solution was directly purified by chromatography (40 g $SiO_2$, EtOAc:MeOH:$NH_3$.$H_2O$, 90:10:1, $R_f$=0.10) to provide the title compound. $^1$H NMR (300 MHz, $CD_3OD$) δ 2.02-2.33 (m, 8H), 2.36 (s, 3H), 3.25 [s (br.), 2H], 5.47 (t, J=4.92 Hz, 1H), 7.23 (d, J=9.16 Hz, 1H), 7.67 (dt, J=8.82, 0.85 Hz, 1H), 8.07 (dd, J=8.82, 1.70 Hz, 1H), 8.10-8.19 (m, 2H), 8.36 (dd, J=1.53, 0.85 Hz, 1H) ppm; MS (DCI/$NH_3$): m/z 336 (M+H)$^+$.

EXAMPLE 5C

5-{6-[(endo)-8-Methyl-8-aza-bicyclo[3.2.1]oct-3-yloxy]-pyridazin-3-yl}-1H-indazole fumarate The product of Example 5B (128 mg, 0.38 mmol) was treated with fumaric acid (46 mg, 0.40 mmol) in EtOAc/EtOH (v. 1:1, 5 mL) at ambient temperature for 15 hours. The mixture was filtered to provide the titled compound. $^1$H NMR (300 MHz, $CD_3OD$) δ 2.29-2.61 (m, 8H), 2.86 (s, 3H), 3.90-3.99 (m, 2H), 5.59 (t, J=4.92 Hz, 1H), 6.69 (s, 2H), 7.32 (d, J=9.16 Hz, 1H), 7.68 (d, J=8.82 Hz, 1H), 8.08 (dd, J=8.82, 1.70 Hz, 1H), 8.15-8.21 (m, 2H), 8.38 (dd, J=1.70, 0.68 Hz, 1H) ppm; MS (DCI/$NH_3$): m/z 336 (M+H)$^+$. Anal. Calcd. for $C_{19}H_{21}N_5O.1.20C_4H_4O_4$: C, 60.22; H, 5.48; N, 14.75. Found: C, 60.03; H, 5.17; N, 14.85.

EXAMPLE 6

1-Methyl-5-{6-[(endo)-8-methyl-8-aza-bicyclo[3.2.1]oct-3-yloxy]-pyridazin-3-yl}-1H-indole trifluoroacetate The product of Example 1A (121 mg, 0.48 mmol) and N-methylindole-5-boronic acid (Frontier, 175 mg, 1.0 mol) were treated according to the procedure outlined in Example 1B to provide the title compound. $^1$H NMR (300 MHz, $CD_3OD$) δ 2.22-2.70 (m, 8H), 2.86 (s, 3H), 3.93-4.03 (m, 2H), 5.53-5.62 (m, 1H), 6.57 (d, J=3.05 Hz, 1H), 7.26 (d, J=3.39 Hz, 1H), 7.37 (d, J=9.49 Hz, 1H), 7.54 (d, J=8.82 Hz, 1H), 7.80 (dd, J=8.65, 1.87 Hz, 1H), 8.16 (d, J=1.70 Hz, 1H), 8.21 (d, J=9.16 Hz, 1H) ppm; MS (DCI/$NH_3$): m/z 349 (M+H)$^+$. Anal. Calculated for $C_{21}H_{24}N_4O.1.60\ CF_3CO_2H$: C, 54.75; H, 4.86; N, 10.55. Found: C, 54.69; H, 4.80; N, 10.58.

EXAMPLE 7

5-{6-[(endo)-8-Methyl-8-aza-bicyclo[3.2.1]oct-3-yloxy]-pyridazin-3-yl}-2-trifluoromethyl-1H-indole trifluoroacetate

EXAMPLE 7A 5-(4,4,5,5-Tetramethyl-[1,3,2]dioxaborolan-2-yl)-2-trifluoromethyl-1H-indole A mixture of 5-Bromo-2-trifluoromethyl-1H-indole (Ref. US 2005043347, 6.05 g, 22.9 mmol), bis(pinacolato)diboron (7.74 g, 30.5 mmol), KOAc (8.05 g, 82 mmol) and $PdCl_2$(dppf).$CH_2Cl_2$ (901 mg, 1.1 mmol) in anhydrous DMF (242 mL) were processed according to the procedure of outlined in Example 5A to provide the titled compound. $^1$H NMR (300 MHz, $CD_3OD$) δ 1.36 (s, 12H), 6.91 (s, 1H), 7.43 (d, J=8.48 Hz, 1H), 7.64 (d, J=8.14 Hz, 1H), 8.11 (s, 1H) ppm; MS (DCI/$NH_3$): 312 (M+H)$^+$.

EXAMPLE 7B (exo)-8-Methyl-8-aza-bicyclo[3.2.1]oct-3-yl-4-nitrobenzoate

To a mixture of (endo)-tropine (2.82 g, 20.0 mmol), 4-nitrobenzoic acid (3.34 g, 20.0 mmol) and triphenylphosphine (5.24 g, 20.0 mmol) in dry THF (100 mL) at room temperature was added diisopropyl azodicarboxylate (4.04 g, 20.0 mmol) and the resulting mixture stirred for 40 hours. The mixture was concentrated under reduced pressure and the residue purified by chromatography (140 g $SiO_2$, EtOAc:MeOH:$NH_3$.$H_2O$, 90:10:1, Rf=0.30) to provide the titled compound. $^1$H NMR (300 MHz, $CD_3OD$) δ 1.74-2.23 (m, 8H), 2.38 (s, 3H), 3.32-3.38 (m, 2H), 5.23-5.38 (m, 1H), 8.21 (d, J=8.82 Hz, 2H), 8.32 (d, J=8.82 Hz, 2H) ppm; MS (DCI/$NH_3$): 291 (M+H)$^+$.

EXAMPLE 7C (exo)-8-methyl-8-aza-bicyclo[3.2.1]octan-3-ol

The product of Example 7B (5.0 g, 0.017 mol) in ethanol (10 mL) was treated with NaOH (1N, 200 mL) at room temperature for 40 hours. The mixture was extracted with the mixture of 10% isopropanol in chloroform (3×100 mL) and the combined extracts concentrated under reduced pressure to provide the title compound. $^1$H NMR (300 MHz, CD$_3$OD) δ 1.55-1.69 (m, 4H), 1.80 (m, 2H), 1.99-2.09 (m, 2H), 2.28 (s, 3H), 3.14-3.21 (m, 2H), 3.79-3.93 (m, 1H) ppm. MS (DCI/NH$_3$): 142 (M+H)$^+$.

EXAMPLE 7D (exo)-3-(6-chloro-pyridazin-3-yloxy)-8-methyl-8-aza-bicyclo[3.2.1]octane The product of Example 7C (721 mg, 5.1 mmol) and 3,6-dichlropyridazine (1.04 g, 7.0 mmol) were treated according to the procedure outlined in Example 1A to provide the title compound. $^1$H NMR (300 MHz, CD$_3$OD) δ 1.87-2.07 (m, 4H), 2.23-2.31 (m, 2H), 2.37 (m, 2H), 3.60-3.69 (m, 2H), 5.54 (m, 1H), 7.15 (d, J=9.16 Hz, 1H), 7.64 (d, J=9.16 Hz, 1H) ppm; MS (DCI/NH$_3$): 254 (M+H)$^+$.

EXAMPLE 7E

5-{6-[(endo)-8-Methyl-8-aza-bicyclo[3.2.1]oct-3-yloxy]-pyridazin-3-yl}-2-trifluoromethyl-1H-indole trifluoroacetate The product of Example 7D (128 mg, 0.5 mmol) and the product of Example 7A (311 mg, 1.0 mmol) were treated according to the procedure outlined in Example 1B to provide the title compound. $^1$H NMR (300 MHz, CD$_3$OD) δ 2.01-2.73 (m, 8H), 2.85 (s, 3H), 4.01-4.10 (m, 2H), 5.64-5.80 (m, 1H), 7.02 (s, 1H), 7.23 (d, J=9.15 Hz, 1H), 7.60 (d, J=8.48 Hz, 1H), 7.95 (dd, J=8.48, 1.70 Hz, 1H), 8.13 (d, J=9.49 Hz, 1H), 8.26 (d, J=1.02 Hz, 1H) ppm; MS (DCI/NH$_3$): m/z 403 (M+H)$^+$. Anal. Calculated for C$_{21}$H$_{21}$F$_3$N$_4$O.1.55 CF$_3$CO$_2$H: C, 49.98; H, 3.92; N, 9.67. Found: C, 49.93; H, 4.09; N, 9.69.

EXAMPLE 8

5-{6-[(exo)-8-Methyl-8-aza-bicyclo[3.2.1]oct-3-yloxy]-pyridazin-3-yl}-1H-indole fumarate The product of Example 7D (154 mg, 0.61 mmol) and 5-(4,4,5,5-tetramethyl-[1,3,2]dioxaborolan-2-yl)-1H-indole (Aldrich, 243 mg, 1.0 mmol) were treated with bis(triphenylphosphine)palladium(II) chloride (Aldrich, 7.02 mg, 0.01 mmol) and biphenyl-2-yl-dicyclohexyl-phosphane (Strem Chemicals, 10.5 mg, 0.03 mmol) in dioxane/EtOH/aqueous 1M Na$_2$CO$_3$ (v. 1/1/1, 3 mL) were heated and microwaved to 150° C. and 300 watts for 15 minutes in an Emry™ Creator microwave. The mixture was cooled to ambient temperature, the solid was filtered off with a syringe filter and the organic solution was directly purified by preparative HPLC (Gilson, Xterra® column, 7 μm, 40×100 mm, eluting solvent, MeCN/H$_2$O (with 0.1 M NH$_4$HCO$_3$/NH$_4$OH, PH=10) (v. 90/10 to 10/90 over 25 minutes), flow rate, 40 mL/min., uv, 254 nm) to provide the free base of the titled compound. The free base was treated with fumaric acid (65 mg, 0.57 mmol) according to the procedure of Example 5C to provide the title compound. $^1$H NMR (300 MHz, CD$_3$OD) δ 2.04-2.50 (m, 6H), 2.57-2.69 (m, 2H), 2.85 (s, 3H), 3.99-4.05 (m, 2H), 5.63-5.78 (m, 1H), 6.56 (d, J=3.05 Hz, 1H), 6.69 (s, 2H), 7.20 (d, J=9.15 Hz, 1H), 7.31 (d, J=3.39 Hz, 1H), 7.51 (d, J=8.48 Hz, 1H), 7.74 (dd, J=8.48, 1.70 Hz, 1H), 8.09 (d, J=9.49 Hz, 1H), 8.14 (d, J=1.02 Hz, 1H) ppm; MS (DCI/NH$_3$): m/z 335 (M+H)$^+$; Anal. Calculated for C$_{20}$H$_{22}$N$_4$O.1.20C$_4$H$_4$O$_4$: C, 62.88; H, 5.70; N, 11.83. Found: C, 62.63; H, 5.70; N, 11.96.

EXAMPLE 9

5-{5-[(endo)-8-Methyl-8-aza-bicyclo[3.2.1]oct-3-yloxy]-pyridin-2-yl}-1H-indole bistosylate

EXAMPLE 9A (endo)-3-(6-Chloro-pyridin-3-yloxy)-8-methyl-8-aza-bicyclo[3.2.1]octane The mixture of (endo)-tropine (Aldrich, 2.82 g, 20 mmol), 2-chloro-5-iodo-pyridine (Aldrich, 2.39 g, 24 mmol), CuI (Strem Chemicals, 0.19 g, 1 mmol) and 1,10-phenanthroline (Aldrich, 0.36 g, 2 mmol), Cs$_2$CO$_3$ (Aldrich, 6.52 g, 20 mmol) in toluene (anhydrous, Aldrich, 25 mL) was stirred at 110° C. for 40 hours. The mixture allowed to cool to ambient temperature and was diluted with CH$_2$Cl$_2$ (100 mL) and washed with water (2×10 mL). The organic solution was concentrated and the title compound was purified by chromatography (SiO$_2$, CH$_2$Cl$_2$:MeOH:NH$_3$.H$_2$O, 90:10:1, R$_f$ 0.10) to provide the titled compound. $^1$H NMR (300 MHz, CD$_3$OD) δ 1.97-2.08 (d, J=14.5 Hz, 2H), 2.13-2.18 (d, J=2.37 Hz, 2H), 2.45 (s, 3H), 3.35-3.41 (m, 2H), 4.66 (t, J=4.8 Hz, 1H), 7.35-7.42 (m, 2H), 7.96-8.04 (dd, J=2.3, 1.0 Hz, 1H) ppm. MS (DCI/NH$_3$) m/z 255 (M+H)$^+$, 253 (M+H)$^+$.

EXAMPLE 9B

5-{5-[(endo)-8-Methyl-8-aza-bicyclo[3.2.1]oct-3-yloxy]-pyridin-2-yl}-1H-indole

The mixture of the product from Example 9A (150 mg, 0.59 mmol), 5-indolylboronic acid (Rsycor, 143.3 mg, 0.89 mmol), Pd(PPh$_3$)$_4$ (Aldrich, 6.8 mg, 0.006 mmol) and K$_2$CO$_3$ (2 M, 1 mL) was heated to 85° C. in dioxane (4 mL) for 12 hours. The mixture was cooled to ambient, filtered and purified by preparative HPLC [Waters XTerra RP18 column, 30×100 mm, eluting solvents, MeCN/H$_2$O (0.1 M aqueous ammonium bicarbonate, adjusted to pH 10 with ammonium hydroxide) (v. 90/10 to 10/90 over 20 min.), flow rate 40 mL/min, uv, 250 nm] to provide the titled compound. $^1$H NMR (300 MHz, CD$_3$OD) δ 1.94-2.06 (m, 2H), 2.06-2.27 (m, 6H), 2.34 (s, 3H), 3.21 [s(br.), 2H], 4.67 (t, J=4.75 Hz, 1H), 6.52 (dd, J=3.05, 1.00 Hz, 1H), 7.26 (d, J=3.39 Hz, 1H), 7.40 (dd, J=8.82, 3.05 Hz, 1H), 7.45 (dt, J=8.48, 0.7 Hz, 1H), 7.63 (dd, J=8.65, 1.87 Hz, 1H), 7.77 (dd, J=8.82, 0.70 Hz, 1H), 7.99-8.08 (m, 1H), 8.18 (d, J=3.05 Hz, 1H) ppm. MS (DCI/NH$_3$) m/z 334 (M+H)$^+$.

EXAMPLE 9C

5-{5-[(endo)-8-Methyl-8-aza-bicyclo[3.2.1]oct-3-yloxy]-pyridin-2-yl}-1H-indole bistosylate The product of Example 9B (40 mg, 0.12 mmol) was treated with p-toluenesulfonic acid monohydrate TsOH.H$_2$O (Aldrich, 38 mg, 0.2 mmol) in a mixture of 25% isopropanol in iso-propylacetate (5 mL) at ambient temperature for 10 hours. The mixture was filtered to provide the titled compound. $^1$H NMR (300 MHz, CD$_3$OD) δ 2.25-2.56 (m, 13H), 2.77-2.89 (m, 4H), 3.87-4.03 (m, 2H), 4.90-2.04 (m, 1H), 6.66 (dd, J=3.1, 0.7 Hz, 1H), 7.19 (d, J=8.10 Hz, 4H), 7.43 (d, J=3.39 Hz, 1H), 7.55-7.65 (m, 2H), 7.68 (d, J=8.14 Hz, 4H), 8.10-8.17 (m, 1H), 8.22-8.38 (m, 2H), 8.46 (d, J=2.03 Hz, 1H) ppm. MS (DCI/NH$_3$): m/z 334 (M+H)$^+$. Anal. Calculated for C$_{21}$H$_{23}$N$_3$O.2.05C$_7$H$_8$SO$_3$.2.00H$_2$O: C, 57.52; H, 6.17; N, 5.72. Found: C, 57.88; H, 5.99; N, 5.33.

EXAMPLE 10

(endo)-3-(6-Benzo[b]thiophen-5-yl-pyridin-3-yloxy)-8-methyl-8-aza-bicyclo[3.2.1]octane bistosylate

EXAMPLE 10A

2-Benzo[b]thiophen-5-yl-4,4,5,5-tetramethyl-[3.2.1]dioxaborolane

A mixture of 5-bromo-benzo[b]thiophene (Maybridge, 4.26 g, 0.0200 mol), bis(pinacolato)diboron (Aldrich, 6.09 g, 0.0240 mol) and potassium acetate (Aldrich, 2.94 g, 0.0300 mol) in 1,4-dioxane (Aldrich, 50 mL) was degassed and purged with $N_2$ three times. [1,1'-Bis(diphenylphosphino)ferrocene]dichloropalladium(II) $PdCl_2(dppf).CH_2Cl_2$ (300 mg, 0.4 mmol, Aldrich) was and the solution was heated to 100° C. for 20 hours. The mixture was then cooled to room temperature, diluted with 300 mL of EtOAc and washed with brine (2×20 mL). The organic solution was concentrated under reduced pressure and the residue was chromatographed to provide the title product. $^1H$ NMR (300 MHz, $CDCl_3$) δ 1.36-1.41 (S, 12H), 7.35 (d, J=5.50 Hz, 1H), 7.42 (d, J=5.70 Hz, 1H), 7.75 (d, J=8.14 Hz, 1H), 7.89 (d, J=8.14 Hz, 1H), 8.31 (s, 1H) ppm. MS (DCI/$NH_3$) m/z 278 (M+H)$^+$.

EXAMPLE 10B (endo)-3-(6-Benzo[b]thiophen-5-yl-pyridin-3-yloxy)-8-methyl-8-aza-bicyclo[3.2.1]octane The product from Example 9A (150 mg, 0.59 mmol) and the product of 10A (231.6 mg, 0.89 mmol) was treated with Pd(PPh$_3$)$_4$ (Aldrich, 6.8 mg, 0.006 mmol) according to the procedure of outlined in Example 9B. The title product was purified by preparative HPLC [Waters XTerra Rβ18 column, 30×100 mm, eluting solvents, MeCN/$H_2O$ (0.1 M aqueous ammonium bicarbonate, adjusted to pH 10 with ammonium hydroxide) (v. 90/10 to 10/90 over 20 min.), flow rate 40 mL/min, uv, 250 nm]. $^1H$ NMR (300 MHz, $CD_3OD$) δ 1.93-2.07 (m, 2H), 2.06-2.28 (m, 6H), 2.34 (s, 3H), 3.21 [s(br.), 2H], 4.70 (t, J=5.26 Hz, 1H), 7.37-7.50 (m, 2H), 7.61 (d, J=5.43 Hz, 1H), 7.80-7.92 (m, 2H), 7.94-8.02 (m, 1H), 8.25 (d, J=2.71 Hz, 1H), 8.34 (d, J=1.36 Hz, 1H) ppm. MS (DCI/$NH_3$) m/z 351 (M+H)$^+$.

EXAMPLE 10C (endo)-3-(6-Benzo[b]thiophen-5-yl-pyridin-3-yloxy)-8-methyl-8-aza-bicyclo[3.2.1]octane bistosylate The product of Example 10B (70 mg, 0.20 mmol) was treated with p-toluenesulfonic acid monohydrate TsOH.$H_2O$ (Aldrich, 38 mg, 0.2 mmol) in a mixture of 25% isopropanol in isopropyl acetate as outlined in Exampled 9C. The mixture was filtered to provide the titled compound. $^1H$ NMR (300 MHz, $CD_3OD$) δ 2.35 (s, 6H), 2.48-2.62 (m, 8H), 2.78 (s, 3H), 3.88-4.05 (m, 2H), 5.02 (t, J=4.58 Hz, 1H), 7.22 (d, J=7.80 Hz, 4H), 7.55 (d, J=5.76 Hz, 1H), 7.70 (d, J=8.48 Hz, 4H), 7.75-7.84 (m, 2H), 8.12-8.22 (m, 2H), 8.29 (d, J=9.20 Hz, 1H) 8.37 (d, J=1.70 Hz, 1H), 8.56 (d, J=3.05 Hz, 1H) ppm. MS (DCI/$NH_3$): m/z 351 (M+H)$^+$. Anal. Calculated for $C_{21}H_{23}N_2OS.2.00C_7H_8SO_3.1.00H_2O$: C, 58.97; H, 5.66; N, 3.93. Found: C, 58.86; H, 5.61; N, 5.71.

EXAMPLE 11

5-{5-[(exo)-8-Methyl-8-aza-bicyclo[3.2.1]oct-3-yloxy]-pyridin-2-yl}-1H-indole tosylate

EXAMPLE 11A (exo)-3-(6-Chloro-pyridin-3-yloxy)-8-methyl-8-aza-bicyclo[3.2.1]octane tosylate To the mixture of (endo)-tropine (Aldrich, 2.82 g, 20 mmol), 2-chloro-5-hydroxy-pyridine (Aldrich, 1.29 g, 10 mmol) and Ph$_3$P (Aldrich, 5.24 g, 20 mmol) was added diisopropyl azadicarboxylate (Aldrich, 4.04 g, 20 mmol) in THF (anhydrous, Aldrich, 100 mL) and the mixture was stirred for two days. The mixture was concentrated under reduced pressure and the title product was purified by chromatography ($SiO_2$, $CH_2Cl_2$:MeOH:$NH_3$.$H_2O$, 90:10:1, $R_f$ 0.40) as solid (1.98 g, yield, 78.3%). $^1H$ NMR (300 MHz, $CD_3OD$) δ 1.63-1.92 (m, 4H), 1.97-2.20 (m, 4H), 2.33 (s, 3H), 3.34 (s, 2H), 4.51-4.75 (m, 1H), 7.27-7.37 (dd, J=8.80, 0.7 Hz, 1H), 7.37-7.49 (dd, J=8.80, 3.00 Hz, 1H), 8.01 (d, J=3.05 Hz, 1H) ppm. MS (DCI/$NH_3$) m/z 255 (M+H)$^+$, 253 (M+H)$^+$.

EXAMPLE 11B

5-{5-[(exo)-8-Methyl-8-aza-bicyclo[3.2.1]oct-3-yloxy]-pyridin-2-yl}-1H-indole

The mixture of the product from Example 11A (150 mg, 0.59 mmol), 5-Indolylboronic acid (Rsycor, 143.3 mg, 0.89 mmol) and Pd(PPh$_3$)$_4$ (Aldrich, 6.8 mg, 0.006 mmol) and $K_2CO_3$ (2 M, 1 mL) in dioxane (4 mL) was stirred at 85° C. for 12 hours according to the procedure of outlined in Example 9B. The title product was purified by preparative HPLC [Waters XTerra RP18 column, 30×100 mm, eluting solvents, MeCN/$H_2O$ (0.1 M aqueous ammonium bicarbonate, adjusted to pH 10 with ammonium hydroxide) (v. 90/10 to 10/90 over 20 min.), flow rate 40 mL/min, uv, 250 nm]. $^1H$ NMR (300 MHz, $CD_3OD$) δ 1.61-1.97 (m, 4H), 2.00-2.23 (m, 4H), 2.35 (s, 3H), 3.22-3.38 (m, 2H), 4.56-4.78 (m, 1H), 6.51 (d, J=4.07 Hz, 1H), 7.26 (d, J=3.39 Hz, 1H), 7.40-7.52 (m, 2H), 7.62 (dd, J=8.48, 1.70 Hz, 1H), 7.75 (d, J=8.82 Hz, 1H), 8.03 (s, 1H), 8.21 (d, J=2.37 Hz, 1H) ppm. MS (DCI/$NH_3$) m/z 334 (M+H)$^+$.

EXAMPLE 11C

5-{5-[(exo)-8-Methyl-8-aza-bicyclo[3.2.1]oct-3-yloxy]-pyridin-2-yl}-1H-indole tosylate The product of Example 11B (50 mg, 0.15 mmol) was treated with p-toluenesulfonic acid monohydrate TsOH.$H_2O$ (Aldrich, 38 mg, 0.2 mmol) in a mixture of 25% isopropanol in isopropyl acetate (5 mL) at ambient temperature for 10 hours according to the procedure of Example 9C. The mixture was filtered to provide the titled compound. $^1H$ NMR (300 MHz, $CD_3OD$) δ 1.90-2.13 (m, 2H), 2.17-2.31 (m, 2H), 2.33-2.42 (m, 5H), 2.44-2.58 (m, 2H), 2.83 (s, 3H), 4.02 [s (br.), 2H], 4.86-5.03 (m, 1H), 6.53 (dd, J=3.22, 0.85 Hz, 1H), 7.22 (d, J=8.14 Hz, 1H), 7.26-7.32 (m, 1H), 7.47 (d, J=8.48 Hz, 1H), 7.56-7.66 (m, 2H), 7.70 (dt, J=8.10, 1.80 Hz, 2H), 7.82 (d, J=8.82 Hz, 1H), 8.05 (d, J=1.36 Hz, 1H), 8.28 (d, J=3.05

Hz, 1H) ppm. MS (DCI/NH$_3$): m/z 334 (M+H)$^+$. Anal. Calculated for C$_{21}$H$_{23}$N$_3$O.1.00C$_7$H$_8$SO$_3$.1.00H$_2$O: C, 64.22; H, 6.35; N, 8.02. Found: C, 64.07; H, 6.16; N, 7.69.

EXAMPLE 12

(exo)-3-[6-(Benzofuran-5-yl)-pyridin-3-yloxy]-8-methyl-8-aza-bicyclo[3.2.1]octane bistrifluoroacetate The product of Example 11A (130 mg, 0.52 mmol) and 1-benzofuran-5-ylboronic acid (Maybridge, 166 mg, 1.0 mmol) were treated according to the procedure outlined in Example 1B to provide the title compound. $^1$H NMR (300 MHz, CD$_3$OD) δ 1.98-2.58 (m, 8H), 2.84 (s, 3H), 3.98-4.09 (m, 2H), 4.93-5.07 (m, 1H), 6.94 (d, J=1.36 Hz, 1H), 7.62 (d, J=8.81 Hz, 1H), 7.73 (dd, J=8.81, 3.05 Hz, 1H), 7.80-7.86 (m, 2H), 7.92 (d, J=8.48 Hz, 1H), 8.13 (d, J=1.36 Hz, 1H), 8.38 (d, J=2.37 Hz, 1H) ppm; MS (DCI/NH$_3$): m/z 335 (M+H)$^+$. Anal. Calculated for C$_{21}$H$_{22}$N$_2$O$_2$.2.00 CF$_3$CO$_2$H: C, 53.39; H, 4.30; N, 4.98. Found: C, 53.28; H, 4.04; N, 4.95.

EXAMPLE 13

5-{5-[(exo)-8-Methyl-8-aza-bicyclo[3.2.1]oct-3-yloxy]-pyridin-2-yl}-1H-indazole hemifumarate The product of Example 11A (139 mg, 0.55 mmol) and the product of Example 5A (325 mg, 1.3 mmol) were treated according to the procedure outlined in Example 8 to provide the title compound. $^1$H NMR (300 MHz, CD$_3$OD) δ 1.97-2.45 (m, 8H), 2.73 (s, 3H), 3.80-3.89 (m, 2H), 4.84-4.96 (m, 1H), 6.68 (s, 1H), 7.56 (dd, J=8.82, 3.05 Hz, 1H), 7.62 (d, J=8.82 Hz, 1H), 7.84 (d, J=8.82 Hz, 1H), 7.97 (dd, J=8.82, 1.70 Hz, 1H), 8.12 (d, J=1.02 Hz, 1H), 8.27 (dd, J=1.53, 0.85 Hz, 1H), 8.32 (d, J=3.05 Hz, 1H) ppm; MS (DCI/NH$_3$): m/z 335 (M+H)$^+$.

EXAMPLE 14

5-{5-[(exo)-8-Methyl-8-aza-bicyclo[3.2.1]oct-3-yloxy]-pyridin-2-yl}-2-trifluoromethyl-1H-indole fumarate The product of Example 11A (130 mg, 0.52 mmol) and the product of Example 7A (319 mg, 1.0 mmol) were treated according to the procedure outlined in Example 8 to provide the title compound. $^1$H NMR (300 MHz, CD$_3$OD) δ 1.99-2.53 (m, 8H), 2.83 (s, 3H), 3.96-4.03 (m, 2H), 4.85-5.02 (m, 1H), 6.69 (s, 2H), 6.97 (s, 1H), 7.50-7.62 (m, 2H), 7.78-7.88 (m, 2H), 8.16 (d, J=1.36 Hz, 1H), 8.31 (d, J=2.71 Hz, 1H) ppm; MS (DCI/NH$_3$): m/z 402 (M+H)$^+$. Anal. Calculated for C$_{22}$H$_{22}$F$_3$N$_3$O1.20C$_4$O$_4$H$_4$: C, 59.53; H, 5.00; N, 7.77. Found: C, 59.26; H, 5.06; N, 7.86.

EXAMPLE 15

4-{5-[(exo)-8-Methyl-8-aza-bicyclo[3.2.1]oct-3-yloxy]-pyridin-2-yl}-1H-indole bistrifluoroacetate The product of Example 11A (130 mg, 0.52 mmol) and indole-4-boronic acid (Apollo, 165 mg, 1.0 mmol) were treated according to the procedure outlined in Example 1B to provide the title compound. $^1$H NMR (300 MHz, CD$_3$OD) δ 2.03-2.64 (m, 8H), 2.85 (s, 3H), 4.00-4.10 (m, 2H), 5.02-5.16 (m, 1H), 6.70 (d, J=2.37 Hz, 1H), 7.25-7.40 (m, 2H), 7.44 (d, J=3.05 Hz, 1H), 7.59 (d, J=7.80 Hz, 1H), 8.01-8.17 (m, 2H), 8.50 (d, J=2.71 Hz, 1H) ppm; MS (DCI/NH$_3$): m/z 334 (M+H)$^+$; Anal. Calculated for C$_{21}$H$_{23}$N$_3$O.2.00C$_2$F$_3$O$_2$H: C, 53.48; H, 4.49; N, 7.48. Found: C, 53.29; H, 4.17; N, 7.35.

EXAMPLE 16

4-{5-[(exo)-8-Methyl-8-aza-bicyclo[3.2.1]oct-3-yloxy]-pyridin-2-yl}-phenylamine bistrifluoroacetate

EXAMPLE 16A

4-{5-[(exo)-8-Methyl-8-aza-bicyclo[3.2.1]oct-3-yloxy]-pyridin-2-yl}-phenylamine

The product of Example 11A (379 mg, 1.5 mmol) and 4-(4,4,5,5-tetramethyl-[1,3,2]dioxaborolan-2-yl)-phenylamine (Aldrich, 552 mg, 2.5 mmol) were processed according to the procedure of Example 5B. The mixture was purified by chromatography (140 g SiO$_2$, EtOAc:MeOH:NH$_3$.H$_2$O, 90:10:1) to provide the title compound. $^1$H NMR (300 MHz, CD$_3$OD) δ 1.76-1.91 (m, 4H), 2.08-2.21 (m, 4H), 3.35-3.42 [s (br.), 2H], 4.62-4.76 (m, 1H), 6.73-6.81 (m, 2H), 7.42 (dd, J=8.81, 3.05 Hz, 1H), 7.57-7.68 (m, 3H), 8.15 (d, J=2.37 Hz, 1H) ppm; MS (DCI/NH$_3$): m/z 310 (M+H)$^+$.

EXAMPLE 16B

4-{5-[(exo)-8-Methyl-8-aza-bicyclo[3.2.1]oct-3-yloxy]-pyridin-2-yl}-phenylamine bistrifluoroacetate The product of Example 16A (135 mg, 0.44 mmol) was repurified by preparative HPLC (Gilson, Xterra® column, 5 μm, 40×100 mm. Eluting Solvent, MeCN/H$_2$O (with 0.1% v. TFA) (v. 90/10 to 10/90 over 25 min.) Flow rate, 40 mL/min., uv, 254 nm). The fractions of the desired product were collected and concentrated under reduced pressure and the residue was stirred in Ether/Ethanol (v. 10/1, 5 mL) at room temperature for 16 hours. The mixture was filtered to provide the bis trifluoroacetate salt. $^1$H NMR (300 MHz, CD$_3$OD) δ 1.99-2.56 (m, 8H), 4.03 [s (br.), 2H], 4.93-5.07 (m, 1H), 6.96-7.07 (m, 2H), 7.73-7.86 (m, 3H), 7.88-7.98 (m, 1H), 8.32 (d, J=3.05 Hz, 1H) ppm; MS (DCI/NH$_3$) m/z 310 (M+H)$^+$; Anal. Calculated for C$_{19}$H$_{23}$N$_3$O.2.30 CF$_3$CO$_2$H: C, 49.58; H, 4.46; N, 7.53. Found: C, 49.58; H, 4.36; N, 7.44.

EXAMPLE 17

5-{6-[(endo)-8-Methyl-8-aza-bicyclo[3.2.1]oct-3-yloxy]-pyridin-3-yl}-1H-indole tosylate

EXAMPLE 17A (endo)-3-(5-Bromo-pyridin-2-yloxy)-8-methyl-8-aza-bicyclo[3.2.1]octane (endo)-Tropine (Aldrich, 282 mg, 2 mmol) was treated with $^t$BuOK (Aldrich, 224 mg, 2 mmol) in THF (20 mL) at ambient temperature for 1 hour followed by the addition of 3,6-dibromopyridine (Aldrich, 569 mg, 2.4 mmol). The mixture was stirred at 60° C. for additional 10 hours and then concentrated under reduced pressure. The residue was dissolved in CHCl$_3$/isopropanol (10:1, 50 mL) and washed with brine (2×5 mL). The organic solution was concentrated under reduced pressure and the title compound was purified by chromatography (SiO$_2$, CH$_2$Cl$_2$:MeOH:NH$_3$.H$_2$O, 90:10:1, R$_f$. 0.10). $^1$H NMR (300 MHz, CD$_3$OD) δ 1.93 (d, J=14.50 Hz, 2H), 2.02-2.23 (m, 6H), 2.31 (s, 3H), 3.17 [s (br.), 2H], 5.16 (t, J=5.26 Hz, 1H), 6.70 (d, J=8.82 Hz, 1H), 7.77 (dd, J=8.81, 2.71 Hz, 1H), 8.16 (d, J=2.71 Hz, 1H) ppm. MS (DCI/NH$_3$): 299 (M+H)$^+$, 297 (M+H)$^+$.

EXAMPLE 17B

5-{6-[(endo)-8-Methyl-8-aza-bicyclo[3.2.1]oct-3-yloxy]-pyridin-3-yl}-1H-indole

The mixture of the product from Example 17A (150 mg, 0.50 mmol), 5-indolylboronic acid (Rsycor, 121.9 mg, 0.75 mmol), Pd(PPh$_3$)$_4$ (Aldrich, 6.8 mg, 0.006 mmol) and K$_2$CO$_3$ (2 M, 1 mL) in dioxane (4 mL) was stirred at 85° C. for 12 hours according to the procedure of outlined in Example 9B. The title product was purified by preparative HPLC [Waters XTerra RP18 column, 30×100 mm, eluting solvents, MeCN/H$_2$O (0.1 M aqueous ammonium bicarbonate, adjusted to pH 10 with ammonium hydroxide) (v. 90/10 to 10/90 over 20 min.), flow rate 40 mL/min, uv, 250 nm]. $^1$H NMR (300 MHz, CD$_3$OD) δ 2.01 (d, J=14.30 Hz, 2H), 2.06-2.28 (m, 6H), 2.34 (s, 3H), 3.17-3.26 (m, 2H), 5.19 (t, J=5.26 Hz, 1H), 6.49 (d, J=2.37 Hz, 1H), 6.82 (d, J=8.48 Hz, 1H), 7.26 (d, J=3.05 Hz, 1H), 7.31 (dd, J=8.48, 1.70 Hz, 1H), 7.45 (d, J=8.48 Hz, 1H), 7.73 (s, 1H), 7.96 (dd, J=8.65, 2.54 Hz, 1H), 8.35 (d, J=2.03 Hz, 1H) ppm. MS (DCI/NH$_3$) m/z 334 (M+H)$^+$.

EXAMPLE 17C

5-{6-[(endo)-8-Methyl-8-aza-bicyclo[3.2.1]oct-3-yloxy]-pyridin-3-yl}-1H-indole bistosylate The product of Example 11B (40 mg, 0.15 mmol) was treated with p-toluenesulfonic acid monohydrate TsOH.H$_2$O (Aldrich, 38 mg, 0.2 mmol) in a mixture of 25% isopropanol in isopropyl acetate (5 mL) at ambient temperature for 10 hours according to the procedure outlined in Example 9C. The mixture was filtered to provide the title compound. $^1$H NMR (300 MHz, CD$_3$OD) δ 2.32-2.58 (m, 14H), 2.81-2.88 (s, 3H), 3.89-4.01 (m, 2H), 5.27-5.41 (m, 1H), 6.52 (d, J=3.39 Hz, 1H), 7.13 (d, J=8.48 Hz, 1H), 7.23 (d, J=7.80 Hz, 4H), 7.35 (dd, J=8.48, 2.03 Hz, 1H), 7.49 (d, J=8.48 Hz, 1H), 7.70 (d, J=8.14 Hz, 4H), 7.79 (s, 1H), 8.24 (dd, J=8.65, 2.54 Hz, 1H), 8.47 (d, J=2.71 Hz, 1H) ppm. MS (DCI/NH$_3$): m/z 334 (M+H)$^+$. Anal. Calculated for C$_{21}$H$_{23}$N$_3$O.2.20C$_7$H$_8$SO$_3$.2.00H$_2$O: C, 58.42; H, 6.01; N, 5.62. Found: C, 58.02; H, 5.84; N, 5.31.

EXAMPLE 18

(endo)-3-(5-Benzo[b]thiophen-5-yl-pyridin-2-yloxy)-8-methyl-8-aza-bicyclo[3.2.1]octane tosylate

EXAMPLE 18A (endo)-3-(5-Benzo[b]thiophen-5-yl-pyridin-2-yloxy)-8-methyl-8-aza-bicyclo[3.2.1]octane The mixture of Example 17A (150 mg, 0.50 mmol), the product of Example 10A (197.0 mg, 0.75 mmol), Pd(PPh$_3$)$_4$ (Aldrich, 6.8 mg, 0.006 mmol) and K$_2$CO$_3$ (2 M, 1 mL) in dioxane (4 mL) was processed according to the procedure outlined in Example 9B. The title product was purified by preparative HPLC [Waters XTerra RP18 column, 30×100 mm, eluting solvents, MeCN/H$_2$O (0.1 M aqueous ammonium bicarbonate, adjusted to pH 10 with ammonium hydroxide) (v. 90/10 to 10/90 over 20 min.), flow rate 40 mL/min, uv, 250 nm]. $^1$H NMR (300 MHz, CD$_3$OD) δ 1.99 (d, J=14.50 Hz, 2H), 2.03-2.28 (m, 6H), 2.33 (s, 3H), 3.14-3.25 (m, 2H), 5.23 (t, J=5.26 Hz, 1H), 6.86 (d, J=8.48 Hz, 1H), 7.43 (d, J=5.43 Hz, 1H), 7.57 (dd, J=8.48, 1.70 Hz, 1H), 7.61 (d, J=5.43 Hz, 1H), 7.91-8.09 (m, 3H), 8.42 (d, J=1.70 Hz, 1H) ppm. MS (DCI/NH$_3$) m/z 351 (M+H)$^+$.

EXAMPLE 18B (endo)-3-(5-Benzo[b]thiophen-5-yl-pyridin-2-yloxy)-8-methyl-8-aza-bicyclo[3.2.1]octane tosylate The product of Example 18A (60 mg, 0.17 mmol) was treated with p-toluenesulfonic acid monohydrate TsOH.H$_2$O (Aldrich, 38 mg, 0.2 mmol) in a mixture of 25% isopropanol in isopropyl acetate (5 mL) at ambient temperature for 10 hours according to the procedure outlined in Example 9C. The mixture was filtered to provide the titled compound. $^1$H NMR (300 MHz, CD$_3$OD) δ 2.34-2.45 (m, 9H), 2.48-2.55 (m, 2H), 2.84 (s, 3H), 3.88-4.00 (m, 2H), 5.39 (t, J=4.41 Hz, 1H), 7.06 (d, J=8.82 Hz, 1H), 7.23 (d, J=7.80 Hz, 2H), 7.45 (d, J=5.43 Hz, 1H), 7.59 (dd, J=8.48, 1.70 Hz, 1H), 7.64 (d, J=5.76 Hz, 1H), 7.70 (d, J=8.48 Hz, 2H), 8.00 (d, J=8.48 Hz, 1H), 8.08 (d, J=1.36 Hz, 1H), 8.18 (dd, J=8.82, 2.37 Hz, 1H), 8.51 (d, J=2.03 Hz, 1H) ppm. MS (DCI/NH$_3$): m/z 351 (M+H)$^+$. Anal. Calculated for C$_{21}$H$_{23}$N$_2$OS.1.10C$_7$H$_8$SO$_3$.1.00H$_2$O: C, 61.79; H, 5.93; N, 5.02. Found: C, 61.44; H, 5.63; N, 4.68.

EXAMPLE 19

5-{6-[(exo)-8-Methyl-8-aza-bicyclo[3.2.1]oct-3-yloxy]-pyridin-3-yl}-1H-indole fumarate

EXAMPLE 19A (exo)-3-(5-Bromo-pyridin-2-yloxy)-8-methyl-8-aza-bicyclo[3.2.1]octane The product of Example 7C (721 mg, 5.1 mmol) and 2,5-dibromopyridine (1.66 g, 7.0 mmol) were treated according to the procedure outlined in Example 1A to provide the title compound. $^1$H NMR (300 MHz, CD$_3$OD) δ 1.88-2.47 (m, 8H), 2.74 (s, 3H), 3.82-3.90 (m, 2H), 5.34-5.48 (m, 1H), 6.71 (d, J=8.82 Hz, 1H), 7.78 (dd, J=8.82, 2.71 Hz, 1H), 8.20 (d, J=2.37 Hz, 1H) ppm; MS (DCI/NH$_3$): 2997 (M+H)$^+$, 297 (M+H)$^+$.

EXAMPLE 19B

5-{6-[(exo)-8-Methyl-8-aza-bicyclo[3.2.1]oct-3-yloxy]-pyridin-3-yl}-1H-indole fumarate The product of Example 19A (129 mg, 0.434 mmol) and 5-indolylboronic acid (165 mg, 1.02 mmol) were treated according to the procedure outlined in Example 8 to provide the title compound. $^1$H NMR (300 MHz, CD$_3$OD) δ 1.97-2.12 (m, 2H), 2.20-2.46 (m, 4H), 2.48-2.60 (m, 2H), 2.84 (s, 3H), 3.96-4.07 (m, 2H), 5.43-5.60 (m, 1H), 6.49 (d, J=3.05 Hz, 1H), 6.70 (s, 2H), 6.82 (d, J=8.48 Hz, 1H), 7.23-7.35 (m, 2H), 7.46 (d, J=8.14 Hz, 1H), 7.73 (d, J=1.70 Hz, 1H), 7.95 (dd, J=8.65, 2.54 Hz, 1H), 8.37 (d, J=2.03 Hz, 1H) ppm; MS DCI/NH$_3$): m/z 334 (M+H)$^+$; Anal. Calculated for C$_{21}$H$_{23}$N$_3$O1.10C$_4$O$_4$H$_4$1.00H$_2$O: C, 63.67; H, 6.18; N, 8.77. Found: C, 63.77; H, 6.26; N, 8.64.

EXAMPLE 20

[6-(1H-Indol-5-yl)-pyridin-3-yl]-[(endo)-8-methyl-8-aza-bicyclo[3.2.1]oct-3-yl]-amine bis(hydrochloride)

EXAMPLE 20A (6-Chloro-pyridin-3-yl)-[(endo)-8-methyl-8-aza-bicyclo[3.2.1]oct-3-yl]-amine A mixture of tropinone (Aldrich, 2.78 g, 20 mmol), 6-chloro-pyridin-3-ylamine (Aldrich, 2.83 g, 22 mmol), $Na_2SO_4$ (anhydrous, Aldrich, 21.3 g, 150 mmol) and $NaBH(OAc)_3$ (Aldrich, 8.48 g, 40 mmol) in HOAc (50 mL) at ambient temperature was stirred for 15 hours. The mixture was filtered and the filtrate washed with EtOH (2×10 mL). The organic solution was concentrated under reduced pressure and the title compound obtained by purified using chromatography ($SiO_2$, $CH_2Cl_2$:MeOH:$NH_3$.$H_2O$, 90:10:2, $R_f$ 0.10). $^1$H NMR (300 MHz, $CD_3OD$) δ 2.16 (d, J=15.26 Hz, 2H), 2.25-2.35 (m, 2H), 2.37-2.60 (m, 4H), 2.81 (s, 3H), 3.65 (t, J=5.93 Hz, 1H), 3.79-3.98 (m, J=2.71 Hz, 1H), 7.09 (dd, J=8.50, 3.00 Hz, 1H), 7.21 (d, J=8.80 Hz, 1H), 7.73 (d, J=2.71 Hz, 1H) ppm. MS (DCI/$NH_3$) m/z 254 (M+H)$^+$, 252 (M+H)$^+$.

EXAMPLE 20B

[6-(1H-Indol-5-yl)-pyridin-3-yl]-[(endo)-8-methyl-8-aza-bicyclo[3.2.1]oct-3-yl]-amine The mixture of Example 20A (250 mg, 1.0 mmol), 5-indolylboronic acid (Rsycor, 241.0 mg, 1.50 mmol), bis(triphenylphosphine)palladium(II) chloride (Aldrich, 10.0 mg, 0.01 mmol) and biphenyl-2-yl-dicyclohexyl-phosphane (Strem Chemicals, 11.0 mg, 0.03 mmol) in dioxane/EtOH/ 1M aqueous $Na_2CO_3$ (v. 1/1/1 3 mL) were heated and microwaved to 130° C. and 300 watts for 15 minutes in an Emry™ Creator microwave. The mixture was filtered through a syringe filter and the liquid was purified by preparative HPLC [Waters XTerra RP18 column, 30×100 mm, eluting solvents, MeCN/$H_2O$ (0.1 M aqueous ammonium bicarbonate, adjusted to pH 10 with ammonium hydroxide) (v. 90/10 to 10/90 over 20 min.), flow rate 40 mL/min, uv, 250 nm] to provide the titled compound. $^1$H NMR (300 MHz, $CD_3OD$) δ 1.88 (d, J=15.20 Hz, 2H) 2.05-2.18 (m, 4H), 2.18-2.31 (m, 2H), 2.37 (s, 3H), 3.26 [s (br.), 2H)], 3.60 (t, J=6.44 Hz, 1H), 6.49 (d, J=3.05 Hz, 1H), 7.05 (dd, J=8.82, 2.71 Hz, 1H), 7.24 (d, J=3.05 Hz, 1H), 7.42 (d, J=8.48 Hz, 1H), 7.49-7.64 (m, 2H), 7.95 (s, 1H) ppm. MS (DCI/$NH_3$) m/z 333 (M+H)$^+$.

EXAMPLE 20C

[6-(1H-Indol-5-yl)-pyridin-3-yl]-[(endo)-8-methyl-8-aza-bicyclo[3.2.1]oct-3-yl]-amine bis(hydrochloride)

The solution of Example 20B (160 mg, 0.48 mmol) in EtOAc (10.0 mL) at ambient temperature was treated with 4M hydrochloric acid in dioxane (0.5 mL, 2.0 mmol) for 10 hours. The title compound was obtained by filtration. $^1$H NMR (300 MHz, $CD_3OD$) δ 2.25 (d, J=15.65 Hz, 2H), 2.32-2.53 (m, 4H), 2.54-2.64 (m, 2H), 2.84 (s, 3H), 3.83 (t, J=6.14 Hz, 1H), 3.97 [s (br.), 2H), 6.63 (d, J=3.07 Hz, 1H), 7.40-7.41 (m, 1H), 7.54 (dd, J=8.60, 1.90 Hz, 1H), 7.62 (d, J=8.60 Hz, 1H), 7.83-7.95 (m, 2H), 8.06 (d, J=1.53 Hz, 1H), 8.12 (d, J=8.90 Hz, 1H) ppm. MS (DCI/$NH_3$): m/z 333 (M+H)$^+$. Anal. Calculated for $C_{21}H_{24}N_4$.2.30HCl 3.35$H_2O$: C, 52.92; H, 6.98; N, 11.75. Found: C, 52.87; H, 6.78; N, 11.35.

EXAMPLE 21

[6-(Benzofuran-5-yl)-pyridin-3-yl]-[(endo)-8-methyl-8-aza-bicyclo[3.2.1]oct-3-yl]-amine fumarate The product of Example 20A (136 mg, 0.54 mmol) and 1-benzofuran-5-ylboronic acid (Aldrich, 185 mg, 1.14 mmol) were treated according to the procedure outlined in Example 8 to provide the title compound. $^1$H NMR (300 MHz, $CD_3OD$) δ 2.14-2.57 (m, 8H), 2.83 (s, 3H), 3.74 (t, J=5.93 Hz, 1H), 3.90 [s (br.), 2H], 6.69 (s, 2H), 6.89 (d, J=1.36 Hz, 1H), 7.13 (dd, J=8.65, 2.88 Hz, 1H), 7.54 (d, J=8.82 Hz, 1H), 7.68 (d, J=8.82 Hz, 1H), 7.72-7.79 (m, 2H), 7.99-8.07 (m, 2H) ppm; MS DCI/$NH_3$): m/z 334 (M+H)$^+$.

EXAMPLE 22

[(endo)-8-Methyl-8-aza-bicyclo[3.2.1]oct-3-yl]-[6-(2-trifluoromethyl-1H-indol-5-yl)-pyridin-3-yl]-amine bistrifluoroacetate The product of Example 20A (130 mg, 0.52 mmol) and the product of Example 7A (262 mg, 0.84 mmol) were treated according to the procedure outlined in Example 1B to provide the title compound. $^1$H NMR (300 MHz, $CD_3OD$) δ 2.17-2.62 (m, 8H), 2.84 (s, 3H), 3.82 (t, J=5.93 Hz, 1H), 3.96 [s (br.), 2H], 7.06 (s, 1H), 7.63-7.80 (m, 3H), 7.95 (d, J=2.71 Hz, 1H), 8.06 (d, J=9.16 Hz, 1H), 8.15 (d, J=1.36 Hz, 1H) ppm; MS DCI/$NH_3$): m/z 401 (M+H)$^+$; Anal. Calculated for $C_{22}H_{22}F_3N_3O$.2.00 $CF_3CO_2H$.0.70 $NH_4OH$: C, 47.75; H, 4.24; N, 7.92. Found: C, 47.69; H, 3.91; N, 8.14.

EXAMPLE 23

[6-(1H-Indazol-5-yl)-pyridin-3-yl]-[(endo)-8-methyl-8-aza-bicyclo[3.2.1]oct-3-yl]-amine fumarate The product of Example 20A (128 mg, 0.51 mmol) and the product of Example 5A (205 mg, 0.84 mmol) were treated according to the procedure outlined in Example 8 to provide the title compound. $^1$H NMR (300 MHz, $CD_3OD$) δ 2.11-2.55 (m, 8H), 2.79 (s, 3H), 3.73 (t, J=5.93 Hz, 1H), 3.85 [s (br.), 2H], 6.67 (s, 3H), 7.13 (dd, J=8.65, 2.88 Hz, 1H), 7.59 (d, J=8.82 Hz, 1H), 7.70 (d, J=8.82 Hz, 1H), 7.90 (dd, J=8.82, 1.70 Hz, 1H), 8.04 (d, J=2.71 Hz, 1H), 8.09 (s, 1H), 8.18 (s, 1H) ppm; MS DCI/$NH_3$): m/z 334 (M+H)$^+$; Anal. Calculated for $C_{20}H_{23}N_5$.1.50$C_4O_4H_4$.1.00 $NH_4OH$: C, 57.55; H, 6.32; N, 15.49. Found: C, 57.46; H, 6.26; N, 15.55.

EXAMPLE 24

[6-(1H-Indol-4-yl)-pyridin-3-yl]-[(endo)-8-methyl-8-aza-bicyclo[3.2.1]oct-3-yl]-amine fumarate The product of Example 20A (130 mg, 0.52 mmol) and indole-4-boronic acid (Apollo, 165 mg, 1.0 mmol) were treated according to the procedure outlined in Example 8 to provide the title compound. $^1$H NMR (300 MHz, $CD_3OD$) δ 2.16-2.60 (m, 8H), 2.84 (s, 3H), 3.76 (t, J=5.76 Hz, 1H), 3.88-3.95 [s (br.), 2H], 6.69 (s, 2H), 6.70 (d, J=3.39 Hz, 1H), 7.14-7.32 (m, 4H), 7.40 (d, J=7.80 Hz, 1H), 7.68 (d, J=8.48 Hz, 1H), 8.06 (d, J=2.71 Hz, 1H) ppm; MS DCI/$NH_3$): m/z 333 (M+H)$^+$; Anal. Calculated for $C_{21}H_{24}N_4 \cdot 1.40C_4O_4H_4 \cdot 0.90H_2O$: C, 62.50; H, 6.19; N, 10.96. Found: C, 62.40; H, 6.17; N, 11.04.

EXAMPLE 25

[(endo)-8-aza-bicyclo[3.2.1]oct-3-yl]-[6-(1H-indol-5-yl)-pyridin-3-yl]-amine

EXAMPLE 25A (endo)-3-(6-Chloro-pyridin-3-ylamino)-8-aza-bicyclo[3.2.1]octane]-8-carboxylic acid tert-butyl ester The mixture of 3-oxo-8-aza-bicyclo[3.2.1]octane-8-carboxylic acid tert-butyl ester (Fluka, 3.50 g, 15.50 mmol), 6-chloro-pyridin-3-ylamine (Aldrich, 2.20 g, 17.1 mmol), $Na_2SO_4$ (anhydrous, Aldrich, 16.6 g, 116 mmol) and NaBH$(OAc)_3$ (Aldrich, 6.59 g, 31.1 mmol) in HOAc (40 mL) was stirred at ambient temperature for 15 hours according to the procedure outlined in Example 20A. The title compound was purified by chromatography ($SiO_2$, hexane:EtOAc, 50:50, $R_f$ 0.40). $^1$H NMR (300 MHz, $CD_3OD$) δ 1.41-1.56 (m, 9H), 1.58-2.90 (m, 8H) 4.13-4.33 (m, 1H), 4.37-4.54 (m, 2H), 7.00 (dd, J=8.81, 3.05 Hz, 0.5H), 7.15 (d, J=8.14 Hz, 0.5H), 7.26 (dd, J=8.30, 3.10 Hz, 0.5H) 7.41 (d, J=8.48 Hz, 0.5H), 7.68 (d, J=3.05 Hz, 0.5H) 7.84 (d, J=2.37 Hz, 0.5H) ppm. MS (DCI/$NH_3$) m/z 340 (M+H)$^+$, 338 (M+H)$^+$.

EXAMPLE 25B

[(endo)-8-Aza-bicyclo[3.2.1]oct-3-yl]-(6-chloro-pyridin-3-yl)-amine

The product of Example 25A (2.92 g, 8.7 mmol) was treated with trifluoroacetic acid (5 mL) in dichloromethane (20 mL) at ambient temperature for 4 hours. The mixture was concentrated under reduced pressure and the residue purified by chromatography ($SiO_2$, $CH_2Cl_2$:MeOH:$NH_3 \cdot H_2O$, 90:10:2, $R_f$ 0.10) to provide the title compound. $^1$H NMR (300 MHz, $CD_3OD$) δ 1.71-1.94 (m, 4H) 2.03-2.22 (m, 4H), 3.42-3.64 (m, 3H), 6.98 (dd, J=8.82, 3.05 Hz, 1H), 7.14 (d, J=8.14 Hz, 1H), 7.65 (d, J=3.05 Hz, 1H) ppm. MS (DCI/$NH_3$) m/z 238 (M+H)$^+$, 240 (M+H)$^+$.

EXAMPLE 25C

[(endo)-8-aza-bicyclo[3.2.11]oct-3-yl]-[6-(1H-indol-5-yl)-pyridin-3-yl]-amine

The product of Example 20A (250 mg, 1.0 mmol), 5-indolylboronic acid (Rsycor, 241.0 mg, 1.50 mmol), bis(triphenylphosphine)palladium(II) chloride (Aldrich, 10.0 mg, 0.01 mmol) and biphenyl-2-yl-dicyclohexyl-phosphane (Strem Chemicals, 11.0 mg, 0.03 mmol) in dioxane/EtOH/1M aqueous $Na_2CO_3$ (1/1/1 3 mL) were heated and microwaved to 130° C. and 300 watts for 15 minutes in an Emry™ Creator microwave. The solid was filtered off with a syringe filter and the liquid was purified by preparative HPLC [Waters XTerra RP18 column, 30×100 mm, eluting solvents, MeCN/$H_2O$ (0.1 M aqueous ammonium bicarbonate, adjusted to pH 10 with ammonium hydroxide) (v. 90/10 to 10/90 over 20 min.), flow rate 40 mL/min, uv, 250 nm] to provide the titled compound. $^1$H NMR (300 MHz, $CD_3OD$) δ 1.96-2.17 (m, 4H), 2.20-2.52 (m, 4H), 3.71 (t, J=6.1 Hz, 1H) 3.80-3.92 (m, 2H), 6.49 (d, J=2.37 Hz, 1H), 7.10 (dd, J=8.82, 3.05 Hz, 1H), 7.25 (d, J=3.05 Hz, 1H), 7.42 (d, J=8.48 Hz, 1H), 7.56 (dd, J=8.48, 1.70 Hz, 1H), 7.63 (d, J=8.48 Hz, 1H), 7.92-8.00 (s, 1H) ppm. MS (DCI/$NH_3$) m/z 319 (M+H)$^+$.

EXAMPLE 26

[6-(4-Amino-3-methyl-phenyl)-pyridin-3-yl]-[(endo)-8-methyl-8-aza-bicyclo[3.2.1]oct-3-yl]-amine fumarate

EXAMPLE 26A

[2-methyl-4-(4,4,5,5-tetramethyl-[3.2.1]dioxaborolan-2-yl)-phenyl]-trifluoroacetamide A mixture of N-(4-Bromo-2-methyl-phenyl)-2,2,2-trifluoro-acetamide (ref. US 2005-0043347, 4.23 g, 15.0 mmol), bis(pinacolato)diboron (Aldrich, 5.07 g, 20 mmol), KOAc (Aldrich, 5.27 g, 53.7 mmol) and $PdCl_2$(dppf):$CH_2Cl_2$ (Aldrich, 203 mg, 0.25 mmol) in anhydrous dioxane (50 mL) at 100° C. for 72 hours. The mixture was cooled to ambient temperature, diluted with EtOAc (150 mL), washed with water (2×25 mL). The organic solution was concentrated under reduced pressure and the residue was purified by chromatography (140 g $SiO_2$, hexane:EtOAc, 80:20, $R_f$ 0.6) to provide the titled compound. $^1$H NMR (300 MHz, $CDCl_3$) δ 1.35 (s, 12H), 2.31 (s, 3H), 7.66-7.80 (m, 3H), 7.90 (d, J=8.14 Hz, 1H) ppm; MS (DCI/$NH_3$): 347 (M+$NH_4$)$^+$.

EXAMPLE 26B

[6-(4-Amino-3-methyl-phenyl)-pyridin-3-yl]-[(endo)-8-methyl-8-aza-bicyclo[3.2.1]oct-3-yl]-amine fumarate The product of Example 20A (130 mg, 0.52 mmol) and the product of Example 26A (277 mg, 0.84 mmol) were treated according to the procedure outlined in Example 8 to provide the title compound. $^1$H NMR (300 MHz, $CD_3OD$) δ 2.12-2.57 (m, 11H), 2.82 (s, 3H), 3.71 (t, J=6.10 Hz, 1H), 3.85-3.94 (m, 2H), 6.69 (s, 2H), 6.77 (d, J=8.14 Hz, 1H), 7.10 (dd, J=8.65, 2.88 Hz, 1H), 7.42 (dd, J=8.14, 2.37 Hz, 1H), 7.47 (s, 1H), 7.53 (d, J=8.82 Hz, 1H), 7.92 (d, J=2.71 Hz, 1H) ppm; MS DCI/$NH_3$): m/z 323 (M+H)$^+$.

EXAMPLE 27

[4-(1H-Indol-5-yl)-phenyl]-[(endo)-8-methyl-8-aza-bicyclo[3.2.1]oct-3-yl]-amine fumarate

EXAMPLE 27A (4-Bromo-phenyl)-(3-endo-8-methyl-8-aza-bicyclo[3.2.1]oct-3-yl)-amine Tropinone (Aldrich, 2.78 g, 20 mmol) and p-bromoaniline (Aldrich, 3.78 g, 22 mmol) were treated according to the procedure outlined in Example 20A to provide the title compound. The title compound was purified by chromatography (140 g $SiO_2$, EtOAc:MeOH (v. 2% $NH_3 \cdot H_2O$), 50:50, $R_f$ 0.25). $^1$H NMR (300 MHz, MeOH-$D_4$) δ 1.71-1.82 (m, 2H), 2.00-2.22 (m, 6H), 2.29 (s, 3H), 3.14 [s (br.), 2H], 3.46 (t, J=6.61 Hz, 1H), 6.46 (d, J=8.81 Hz, 2H), 7.17 (d, J=9.15 Hz, 2H) ppm; MS (DCI/$NH_3$): 297 (M+H)$^+$ 295 (M+H)$^+$.

EXAMPLE 27B

[4-(1H-Indol-5-yl)-phenyl]-[(endo)-8-methyl-8-aza-bicyclo[3.2.1]oct-3-yl]-amine fumarate The product of Example 27A (134 mg, 0.45 mmol) and 5-(4,4,5,5-tetramethyl-[1,3,2]dioxaborolan-2-yl)-1H-indole (Aldrich, 198 mg, 0.81 mmol) were treated according to the procedure outlined in Example 8 to provide the title compound. $^1$H NMR (300 MHz, CD$_3$OD) δ 2.16-2.60 (m, 8H), 2.82 (s, 3H), 3.72 (t, J=5.76 Hz, 1H), 3.89 [s (br.), 2H], 6.44 (d, J=2.37 Hz, 1H), 6.66-6.74 (m, 5.3H), 7.21 (d, J=3.39 Hz, 1H), 7.26-7.32 (m, 1H), 7.35-7.41 (m, 1H), 7.46 (d, J=8.82 Hz, 2H), 7.67 (d, J=1.02 Hz, 1H) ppm; MS DCI/NH$_3$): m/z 332 (M+H)$^+$; Anal. Calculated for C$_{22}$H$_{25}$N$_3$.1.65C$_4$O$_4$H$_4$: C, 65.68; H, 6.09; N, 8.03. Found: C, 65.62; H, 6.40; N, 8.14.

EXAMPLE 28

[4-(1H-Indazol-5-yl)-phenyl]-[(endo)-8-methyl-8-aza-bicyclo[3.2.1]oct-3-yl]-amine fumarate The product of Example 27A (134 mg, 0.45 mmol) and the product of Example 5A (265 mg, 1.08 mmol) were treated according to the procedure outlined in Example 8 to provide the title compound. $^1$H NMR (300 MHz, CD$_3$OD) δ 2.14-2.61 (m, 8H), 2.82 (s, 3H), 3.72 (t, J=5.93 Hz, 1H), 3.89 [s (br.), 2H], 6.67-6.77 (m, 5H), 7.45-7.52 (m, 2H), 7.52-7.58 (m, 1H), 7.59-7.65 (m, 1H), 7.87 (s, 1H), 8.04 (s, 1H) ppm; MS DCI/NH$_3$): m/z 333 (M+H)$^+$; Anal. Calculated for C$_{21}$H$_{24}$N$_4$.1.48C$_4$O$_4$H$_4$: C, 64.12; H, 5.98; N, 11.11. Found: C, 64.00; H, 5.98; N, 11.22.

EXAMPLE 29

[(endo)-8-Methyl-8-aza-bicyclo[3.2.1]oct-3-yl]-[4-(1-methyl-1H-indol-5-yl)-phenyl]-amine fumarate The product of Example 27A (128 mg, 0.43 mmol) and N-methylindole-5-boronic acid (Frontier, 142 mg, 0.81 mmol) were treated according to the procedure outlined in Example 8 to provide the title compound. $^1$H NMR (300 MHz, CD$_3$OD) δ 2.12-2.63 (m, 8H), 2.82 (s, 3H), 3.72 (t, J=5.93 Hz, 1H), 3.80 (s, 3H), 3.88 [s (br.), 2H], 6.42 (d, J=3.05 Hz, 1H), 6.66-6.74 (m, 4H), 7.13 (d, J=3.05 Hz, 1H), 7.36 (d, J=1.0 Hz, 2H), 7.46 (d, J=8.48 Hz, 2H), 7.67 (t, J=1.20 Hz, 1H) ppm; MS DCI/NH$_3$): m/z 346 (M+H)$^+$. Anal. Calculated for C$_{23}$H$_{27}$N$_3$.1.10C$_4$O$_4$H$_4$: C, 69.55; H, 6.69; N, 8.88. Found: C, 69.29; H, 6.76; N, 8.85.

EXAMPLE 30

(4-Benzo[b]thiophen-5-yl-phenyl)-[(endo)-8-methyl-8-aza-bicyclo[3.2.1]oct-3-yl]-amine trifluoroacetate The product of Example 27A (129 mg, 0.44 mmol) and 2-benzo[b]thiophen-5-yl-4,4,5,5-tetramethyl-[1,3,2]dioxaborolane (Maybridge, 189 mg, 0.73 mmol) were treated according to the procedure outlined in Example 1B to provide the title compound. $^1$H NMR (300 MHz, CD$_3$OD) δ 2.17-2.60 (m, 8H), 2.82 (s, 3H), 3.73 (t, J=5.76 Hz, 1H), 3.90 [s (br.), 2H], 6.73 (d, J=8.82 Hz, 2H), 7.38 (d, J=5.76 Hz, 1H), 7.48-7.59 (m, 4H), 7.88 (d, J=8.48 Hz, 1H), 7.97 (d, J=1.70 Hz, 1H) ppm; MS DCI/NH$_3$): m/z 349 (M+H)$^+$; Anal. Calculated for C$_{22}$H$_{24}$N$_2$S.1.10C$_2$F$_3$O$_2$H: C, 61.33; H, 5.34; N, 5.91. Found: C, 61.03; H, 5.34; N, 5.76.

EXAMPLE 31

[4-(Benzofuran-5-yl)-phenyl]-[(endo)-8-methyl-8-aza-bicyclo[3.2.1]oct-3-yl]-amine fumarate The product of Example 27A (135 mg, 0.46 mmol) and 5-(4,4,5,5-tetramethyl-[1,3,2]dioxaborolan-2-yl)-benzofuran (Maybridge, 189 mg, 0.77 mmol) were treated according to the procedure outlined in Example 8 to provide the title compound. $^1$H NMR (300 MHz, CD$_3$OD) δ 2.15-2.60 (m, 8H), 2.82 (s, 3H), 3.72 (t, J=5.93 Hz, 1H), 3.88 [s (br.), 2H], 6.65-6.76 (m, 4H), 6.83 (d, J=2.71 Hz, 1H), 7.40-7.52 (m, 4H), 7.69-7.75 (m, 2H) ppm; MS DCI/NH$_3$): m/z 333 (M+H)$^+$; Anal. Calculated for C$_{22}$H$_{24}$N$_2$O.1.15C$_4$O$_4$H$_4$: C, 68.57; H, 6.19; N, 6.01. Found: C, 68.42; H, 6.17; N, 6.02.

EXAMPLE 32

[4-(1H-Indol-4-yl)-phenyl]-[(endo)-8-methyl-8-aza-bicyclo[3.2.1]oct-3-yl]-amine fumarate The product of Example 27A (125 mg, 0.42 mmol) and indole-4-boronic acid (Apollo, 131 mg, 0.81 mmol) were treated according to the procedure outlined in Example 8 to provide the title compound. $^1$H NMR (300 MHz, CD$_3$OD) δ 2.11-2.68 (m, 8H), 2.83 (s, 3H), 3.74 (t, J=8.31 Hz, 1H), 3.89 [s (br.), 2H] 6.58 (dd, J=3.39, 1.02 Hz, 1H), 6.68 (s, 2H), 6.74 (d, J=8.82 Hz, 2H), 6.99 (dd, J=7.12, 1.02 Hz, 1H), 7.08-7.15 (m, 1H), 7.23 (d, J=3.39 Hz, 1H), 7.29 (d, J=8.14 Hz, 1H), 7.51 (d, J=8.81 Hz, 2H) ppm; MS DCI/NH$_3$): m/z 332 (M+H)$^+$; Anal. Calculated for C$_{22}$H$_{25}$N$_3$.1.00C$_4$O$_4$H$_4$: C, 69.78; H, 6.53; N, 9.39. Found: C, 70.17; H, 6.69; N, 9.58.

EXAMPLE 33

[3-(1H-Indol-5-yl)-phenyl]-[(endo)-8-methyl-8-aza-bicyclo[3.2.1]oct-3-yl]-amine fumarate

EXAMPLE 33A (3-Bromo-phenyl)-[(endo)-8-methyl-8-aza-bicyclo[3.2.1]oct-3-yl]-amine Tropinone (696 mg, 5.0 mmol) and m-bromoaniline (946 mg, 5.5 mmol) were treated according to the procedure outlined in Example 20A to provide the title compound. The title compound was purified by chromatography [140 g SiO$_2$, EtOAc:MeOH (v. 2% NH$_3$.H$_2$O), 50:50, R$_f$=0.25]. $^1$H NMR (300 MHz, MeOH-D$_4$) δ 1.72-2.23 (m, 8H), 2.29 (s, 3H), 3.14 [s (br.), 2H], 3.47 (t, J=6.44 Hz, 1H), 6.46-6.52 (ddd, J=8.20, 2.00, 1.00 Hz, 1H), 6.64-6.72 (m, 2H), 6.92-7.02 (t, J=8.10 Hz, 1H) ppm; MS (DCI/NH$_3$): 297 (M+H)$^+$, 295 (M+H)$^+$.

EXAMPLE 33B

[3-(1H-Indol-5-yl)-phenyl]-[(endo)-8-methyl-8-aza-bicyclo[3.2.1]oct-3-yl]-amine fumarate The product of Example 33A (128 mg, 0.43 mmol) and indole-5-boronic acid (165 mg, 1.0 mmol) were treated according to the procedure outlined in Example 8 to provide the title compound. $^1$H NMR (300 MHz, CD$_3$OD) δ 2.19-2.61 (m, 8H), 2.81 (s, 3H), 3.75 (t, J=5.76 Hz, 1H), 3.83-3.92 (m, 2H), 6.47 (dd, J=3.05, 0.70 Hz, 1H), 6.55 (ddd, J=7.10, 2.60, 0.70 Hz, 1H), 6.68 (s, 2H), 6.89 (t, J=2.03 Hz, 1H), 6.96 (ddd, J=7.80, 1.70, 1.00 Hz, 1H), 7.20 (t, J=7.80 Hz, 1H), 7.24 (d, J=7.10 Hz, 1H), 7.34 (dd, J=8.50, 1.70 Hz, 1H), 7.39 (t, J=8.40 Hz, 1H), 7.74 (dd, J=1.70, 0.70 Hz 1H) ppm; MS DCI/NH$_3$): m/z 332 (M+H)$^+$; Anal. Calculated for $C_{22}H_{25}N_3 \cdot 1.10C_4H_4O_4 \cdot 0.40C_4H_8O_2$: C, 68.03; H, 6.65; N, 8.50. Found: C, 67.68; H, 6.85; N, 8.78.

EXAMPLE 34

[3-(1H-Indol-4-yl)-phenyl]-[(endo)-8-methyl-8-aza-bicyclo[3.2.1]oct-3-yl]-amine trifluoroacetate The product of Example 33A (128 mg, 0.43 mmol) and indole-4-boronic acid (Apollo, 168 mg, 1.0 mmol) were treated according to the procedure outlined in Example 1B to provide the title compound. $^1$H NMR (300 MHz, $CD_3OD$) δ 2.22-2.64 (m, 8H), 2.81 (s, 3H), 3.74 (t, J=5.42 Hz, 1H), 3.87-3.93 (m, 2H), 6.57-6.67 (m, 2H), 6.92 (t, J=2.10 Hz, 1H), 6.99 (dt, J=7.80, 1.00 Hz, 1H) 7.14 (t, J=7.56 Hz, 1H), 7.21-7.28 (m, 2H), 7.35 (d, J=8.14 Hz, 1H) ppm; MS DCI/$NH_3$): m/z 332 (M+H)$^+$; Anal. Calculated for $C_{22}H_{25}N_3 \cdot 1.10$ $CF_3CO_2H \cdot 0.60$ EtOH: C, 62.96; H, 6.18; N, 8.67. Found: C, 62.85; H, 5.98; N, 8.65.

EXAMPLE 35

5-{6-[(endo)-8-Methyl-8-aza-bicyclo[3.2.1]oct-3-yloxy]-pyridazin-3-yl}-2-trifluoromethyl-1H-indole trifluoroacetate The product of Example 1A (89 mg, 0.35 mmol) and the product of Example 7A (299 mg, 0.96 mmol) were treated according to the procedure outlined in Example 1B to provide the title compound. $^1$H NMR (300 MHz, $CD_3OD$) δ 2.22-2.67 (m, 8H), 2.86 (s, 3H), 3.93-4.01 [s (br), 2H], 5.55-5.62 (m, 1H), 7.02 (t, J=1.02 Hz, 1H), 7.32 (d, J=9.15 Hz, 1H), 7.60 (d, J=8.81 Hz, 1H), 7.94 (dd, J=8.82, 1.70 Hz, 1H), 8.16 (d, J=9.49 Hz, 1H), 8.26 (d, J=1.36 Hz, 1H) ppm; MS DCI/$NH_3$): m/z 403 (M+H)$^+$; Anal. Calculated for $C_{21}H_{21}F_3N_4O1.53CF_3CO_2H$: C, 50.09; H, 3.94; N, 9.71. Found: C, 50.07; H, 3.94; N, 9.66.

EXAMPLE 36

4-{6-[(exo)-8-Methyl-8-aza-bicyclo[3.2.1]oct-3-yloxy]-pyridazin-3-yl}-1H-indole fumarate The product of Example 7D (129 mg, 0.51 mmol) and indole-4-boronic acid (Apollo, 161 mg, 1.0 mmol) were treated according to the procedure outlined in Example 8 to provide the title compound. $^1$H NMR (300 MHz, $CD_3OD$) δ 2.05-2.50 (m, 6H), 2.66 (ddd, J=14.92, 5.76, 3.05 Hz, 2H), 2.85 (s, 3H), 4.03 (dd, J=3.73, 3.05 Hz, 2H), 5.67-5.83 (m, 1H), 6.79 (dd, J=3.22, 0.85 Hz, 1H), 7.22-7.30 (m, 2H), 7.37 (d, J=3.05 Hz, 1H), 7.41 (dd, J=7.29, 0.85 Hz, 1H), 7.54 (d, J=8.14 Hz, 1H), 8.08 (d, J=9.15 Hz, 1H) ppm; MS DCI/$NH_3$): m/z 335 (M+H)$^+$; Anal. Calculated for $C_{20}H_{22}N_4O \cdot 1.20C_4H_4O_4$: C, 62.88; H, 5.70; N, 11.83. Found: C, 62.90; H, 5.53; N, 11.79.

EXAMPLE 37

5-{6-[(exo)-8-Methyl-8-aza-bicyclo[3.2.1]oct-3-yloxy]-pyridin-3-yl}-1H-indole fumarate

EXAMPLE 37A (exo)-3-(5-Bromo-pyridin-2-yloxy)-8-methyl-8-aza-bicyclo[3.2.1]octane The product of Example 7C (721 mg, 5.1 mmol) and 2,5-dibromo-pyridine (Aldrich, 1.66 g, 7.0 mmol) were treated according to the procedure outlined in Example 1A to provide the title compound. $^1$H NMR (300 MHz, $CD_3OD$) δ 1.90-2.46 (m, 8H), 2.74 (s, 3H), 3.81-3.90 (m, 2H), 5.34-5.48 (m, 1H), 6.71 (d, J=8.82 Hz, 1H), 7.78 (dd, J=8.82, 2.71 Hz, 1H), 8.20 (d, J=2.37 Hz, 1H) ppm; MS DCI/$NH_3$): m/z 299 (M+H)$^+$ 297 (M+H)$^+$.

EXAMPLE 37B

5-{6-[(exo)-8-Methyl-8-aza-bicyclo[3.2.1]oct-3-yloxy]-pyridin-3-yl}-1H-indole fumarate The product of Example 37A (129 mg, 0.43 mmol) and indole-5-boronic acid (Ryscor Inc., 165 mg, 1.0 mmol) were treated according to the procedure outlined in Example 8 to provide the title compound. $^1$H NMR (300 MHz, $CD_3OD$) δ 1.96-2.62 (m, 8H), 2.84 (s, 3H), 3.97-4.04 (m, 2H), 5.44-5.58 (m, 1H), 6.49 (dd, J=3.22, 0.85 Hz, 1H), 6.70 (s, 2H), 6.82 (d, J=8.48 Hz, 1H), 7.27 (d, J=3.05 Hz, 1H), 7.30 (dd, J=8.48, 1.70 Hz, 1H), 7.46 (d, J=8.14 Hz, 1H), 7.73 (d, J=1.70 Hz, 1H), 7.95 (dd, J=8.65, 2.54 Hz, 1H), 8.37 (d, J=2.03 Hz, 1H) ppm; MS DCI/$NH_3$): m/z 334 (M+H)$^+$; Anal. Calculated for $C_{21}H_{23}N_3O \cdot 1.10C_4H_4O_4 \cdot 1.00H_2O$: C, 63.67; H, 6.18; N, 8.77. Found: C, 63.77; H, 6.26; N, 8.64.

EXAMPLE 38

5-{6-[(exo)-8-Methyl-8-aza-bicyclo[3.2.1]oct-3-yloxy]-pyridin-3-yl}-2-trifluoromethyl-1H-indole bisfumarate The product of Example 37A (129 mg, 0.43 mmol) and 5-(4,4,5,5-tetramethyl-[1,3,2]dioxaborolan-2-yl)-2-trifluoromethyl-1H-indole (Aldrich, 319 mg, 1.02 mmol) were treated according to the procedure outlined in Example 8 to provide the title compound. $^1$H NMR (300 MHz, $CD_3OD$) δ 1.92-2.63 (m, 8H), 2.85 (s, 3H), 4.02 [s (br), 2H], 5.46-5.61 (m, 1H), 6.71 (s, 4H), 6.84 (d, J=8.48 Hz, 1H), 6.95 (s, 1H), 7.47-7.59 (m, 2H), 7.85 (s, 1H), 7.97 (dd, J=8.65, 2.54 Hz, 2H), 8.40 (d, J=2.03 Hz, 1H) ppm; MS DCI/$NH_3$): m/z 402 (M+H)$^+$. Anal. Calculated for $C_{22}H_{22}F_3N_3O \cdot 2.00C_4H_4O_4$: C, 56.87; H, 4.77; N, 6.63. Found: C, 56.98; H, 5.09; N, 6.29.

EXAMPLE 39

4-{6-[(exo)-8-Methyl-8-aza-bicyclo[3.2.1]oct-3-yloxy]-pyridazin-3-yl}-1H-indole fumarate The product of Example 7D (129 mg, 0.51 mmol) was coupled with indole-4-boronic acid (Apollo, 161 mg, 1.0 mmol) to give the free base of the title compound (150 mg, 0.45 mmol). It was then was treated with fumaric acid (52.0 mg, 0.45 mmol) according to the procedure of Example of 5C to give the title compound as white solid. $^1$H NMR (300 MHz, $CD_3OD$) δ 2.05-2.49 (m, 6H) 2.60-2.71 (m, 2H) 2.85 (s, 3H) 4.01-4.07 (m, 2H) 5.69-5.81 (m, 1H) 6.69 (s, 2H) 6.79 (dd, J=3.22, 0.85 Hz, 1H) 7.23-7.29 (m, 2H) 7.37 (d, J=3.05 Hz, 1H) 7.41 (dd, J=7.29, 0.85 Hz, 1H) 7.54 (d, J=8.14 Hz, 1H) 8.08 (d, J=9.15 Hz, 1H) ppm. MS (DCI/$NH_3$): m/z 335 (M+H)$^+$. Anal. Calculated for $C_{20}H_{22}N_4O \cdot 1.2C_4O_4H_4$: C, 62.88; H, 5.70; N, 11.83. Found: C, 62.90; H, 5.53; N, 11.79.

EXAMPLE 40

6-{5-[(exo)-8-Methyl-8-aza-bicyclo[3.2.1]oct-3-yloxy]-pyridin-2-yl}-1H-indole hydrochloride

EXAMPLE 40A

6-{5-[(exo)-8-Methyl-8-aza-bicyclo[3.2.1]oct-3-yloxy]-pyridin-2-yl}-1H-indole

Under $N_2$, the mixture of the product from Example 11A (240 mg, 0.95 mmol) was coupled with 6-indolylboronic acid (Frontier Scientific, 229 mg, 1.42 mmol) according to the procedure of Example 11B to provide the title product. $^1$H NMR (300 MHz, $CD_3OD$) δ 1.72-1.93 (m, 4H), 2.00-2.25 (m, 4H), 2.39 (s, 3H), 3.23-3.35 (m, 2H), 4.56-4.82 (m, 1H), 7.29 (d, J=3.05 Hz, 1H), 7.46 (d, J=2.71 Hz, 1H), 7.47-7.51 (m, 1H), 7.53 (d, J=1.36 Hz, 1H), 7.60 (d, J=8.52 Hz, 1H), 7.76 (d, J=8.82 Hz, 1H), 7.88 (s, 1H), 8.22 (d, J=3.05 Hz, 1H) ppm; MS (DCI/$NH_3$) m/z 334 $(M+H)^+$.

EXAMPLE 40B

6-{5-[(exo)-8-Methyl-8-aza-bicyclo[3.2.1]oct-3-yloxy]-pyridin-2-yl}-1H-indole hydrochloride The product of Example 40A (210 mg, 0.63 mmol) was treated with HCl (Aldrich, 4 M in dioxane, 0.5 mL, 2.0 mmol) EtOAc (10 mL) at ambient temperature for 10 hours and concentrated under reduced pressure to provide the title compound. $^1$H NMR (300 MHz, $CD_3OD$) δ 2.14-2.32 (m, 2H), 2.26-2.49 (m, 4H), 2.49-2.65 (m, 2H), 2.85 (s, 3H), 3.99-4.18 (m, 2H), 5.07-5.31 (m, 1H), 6.60 (d, J=4.07 Hz, 1H), 7.46-7.56 (m, 2H), 7.82 (d, J=8.48 Hz, 1H), 7.98 (s, 1H), 8.34 (s, 1H), 8.35 (d, J=2.71 Hz, 1H), 8.55 (d, J=2.37 Hz, 1H) ppm. MS (DCI/$NH_3$): m/z 334 $(M+H)^+$. Anal. Calculated for $C_{21}H_{23}N_3O.1.00HCl.1.20H_2O$: C, 64.42; H, 6.80; N, 10.73. Found: C, 64.54; H, 6.61; N, 10.89.

EXAMPLE 41

5-{5-[(endo)-8-Methyl-8-aza-bicyclo[3.2.1]oct-3-yloxy]-pyrazin-2-yl)-1H-indole tosylate

EXAMPLE 41A

5-Bromo-pyrazin-2-ylamine

To the solution of 2-aminopyrazine (Aldrich, 4.75 g, 50 mmol) in anhydrous MeCN (Aldrich, 50 mL) was slowly added the solution of N-bromosuccinimide (Aldrich, 8.90 g, 50 mmol) in MeCN (anhydrous, 50 mL) at 0-10° C. The reaction mixture was then stirred at ambient temperature and quenched with saturated $Na_2S_2O_3$ (5.0 mL). The mixture was concentrated and the residue was extracted with EtOAc (3×50 mL). The combined extracts were concentrated and the title compound was purified by chromatography ($SiO_2$, EtOAc/hexane=1/1, v. $R_f$=0.50). $^1$H NMR (300 MHz, $CDCl_3$) δ 7.77 (d, J=1.36 Hz, 1H), 8.09 (d, J=1.36 Hz, 1H) ppm; m/z 174 $(M+H)^+$, 174 $(M+H)^+$.

EXAMPLE 41B

5-Bromo-2-iodopyrazine

Under $N_2$, to the mixture of the product of Example 41A (7.50 g, 43 mmol) in DME (anhydrous, Aldrich, 200 mL) was added CsI (Aldrich, 11.20 g, 43 mmol), iodine (Aldrich, 5.52 g, 21.6 mmol), CuI (Stream, 2.52 g, 13.2 mmol) and isoamyl nitrite (34.8 mL, 259.2 mmol) at ambient temperature. It was then heated to 60° C. and stirred for 30 min. till no gas evolution was observed. After being cooled down to room temperature, the dark mixtures was poured into a flask containing EtOAc (200 mL) and saturated $NH_4Cl$ (200 mL), stirred for 10 min. The organic layer was separated and the aqueous layer was extracted with EtOAc (2×1000 mL). The combined organic solution was washed with 5% of $Na_2S_2O_3$ aqueous (2×50 mL), brine (50 mL) and dried over MgSO4. The drying agents were filtered off and the organic solution was concentrated to provide the title compound. $^1$H NMR (300 MHz, $CDCl_3$) δ 8.50 (d, J=1.36 Hz, 1H), 8.62 (d, J=1.36 Hz, 1H) ppm; m/z 284 $(M+H)^+$, 286 $(M+H)^+$.

EXAMPLE 41C (endo)-3-(5-Iodo-pyrazin-2-yloxy)-8-methyl-8-aza-bicyclo[3.2.1]octane Under $N_2$, the mixture of (endo)-tropine (Aldrich, 1.54 g, 11 mmol) was treated with potassium t-butoxide (Aldrich, 0.96 g, 10 mmol) in THF (anhydrous, Aldrich, 50 mL) at ambient temperature for 1 h. The product of Example 41B (2.85 g, 10.0 mmol) and was added. The brown mixture was stirred at ambient temperature for 4 hours and quenched with water (5 mL). The mixture was concentrated and the residue was purified by chromatography (150 g $SiO_2$, EtOAc:MeOH:$NH_3.H_2O$, 90:10:1, $R_f$, 0.20) to give the title compound. $^1$H NMR (300 MHz, $CD_3OD$) δ 2.16-2.60 (m, 8H), 2.84 (s, 3H), 3.78-4.05 (m, 2H), 5.17-5.40 (m, 1H), 8.14 (d, J=1.36 Hz, 1H), 8.42 (d, J=1.36 Hz, 1H) ppm; MS (DCI/$NH_3$) m/z 346 $(M+H)^+$.

EXAMPLE 41D

5-{5-[(endo)-8-Methyl-8-aza-bicyclo[3.2.1]oct-3-yloxy]-pyrazin-2-yl}-1H-indole

The product from Example 41C (200 mg, 0.58 mmol), was coupled with 5-indolylboronic acid (Rsycor, 143.3 mg, 0.89 mmol) according to the procedure of Example 9B to provide the title product. $^1$H NMR (300 MHz, $CD_3OD$) δ 1.94-2.05 (m, 2H), 2.07-2.29 (m, 6H), 2.34 (s, 3H), 3.15-3.27 (m, 2H), 5.29 (t, J=5.09 Hz, 1H), 6.53 (d, J=2.37 Hz, 1H), 7.27 (d, J=3.39 Hz, 1H), 7.47 (d, J=8.48 Hz, 1H), 7.68 (dd, J=8.48, 1.70 Hz, 1H), 8.11 (s, 1H), 8.17 (d, J=1.70 Hz, 1H), 8.58 (d, J=1.36 Hz, 1H) ppm. MS (DCI/$NH_3$) m/z 335 $(M+H)^+$.

EXAMPLE 41E

5-{5-[(endo)-8-Methyl-8-aza-bicyclo[3.2.1]oct-3-yloxy]-pyrazin-2-yl}-1H-indole tosylate The product of Example 41D (90 mg, 0.27 mmol) was treated with p-toluenesulfonic acid monohydrate $TsOH.H_2O$ (Aldrich, 57 mg, 0.3 mmol) in EtOAc/EtOH (v. 4:1, 5 mL) at ambient temperature for 10 hour. The mixture was concentrated under reduced pressure to provide the title compound. $^1$H NMR (300 MHz, $CD_3OD$) δ 2.36 (s, 3H), 2.38-2.48 (m, 4H), 2.48-2.61 (m, 4H), 2.84 (s, 3H), 3.84-4.05 (m, 2H), 5.41 (t, J=4.41 Hz, 1H), 7.23 (d, J=7.80 Hz, 2H), 7.30 (s, 1H), 7.49 (d, J=8.48 Hz, 1H), 7.65-7.77 (m, 4H), 8.13 (d, J=1.70 Hz, 1H), 8.29 (s, 1H) ppm. MS (DCI/$NH_3$): m/z 335 $(M+H)^+$. Anal. Calculated for $C_{20}H_{22}N_4O.1.38C_7H_8SO_3.0.80H_2O$: C, 60.74; H, 5.95; N, 9.55. Found: C, 61.00; H, 5.63; N, 9.17.

EXAMPLE 42

4-{5-[(endo)-8-Methyl-8-aza-bicyclo[3.2.1]oct-3-yloxy]-pyrazin-2-yl}-1H-indole bistosylate

EXAMPLE 42A

4-{5-[(endo)-8-Methyl-8-aza-bicyclo[3.2.1]oct-3-yloxy]-pyrazin-2-yl}-1H-indole

The product from Example 41C (200 mg, 0.58 mmol), was coupled with 4-indolylboronic acid (Apollo, 143.3 mg, 0.89 mmol) according to the procedure of Example 9B to provide the title compound. $^1$H NMR (300 MHz, $CD_3OD$) δ 1.97-2.06 (m, 2H), 2.08-2.30 (m, 6H), 2.34 (s, 3H), 3.16-3.28 (m, 2H), 5.33 (t, J=5.09 Hz, 1H), 6.82 (d, J=3.39 Hz, 1H), 7.22 (t, J=7.50 Hz, 1H), 7.34 (d, J=3.05 Hz, 1H), 7.40 (d, J=7.46 Hz, 1H), 7.47 (d, J=8.14 Hz, 1H), 8.27 (d, J=1.36 Hz, 1H), 8.61 (d, J=1.36 Hz, 1H) ppm. MS (DCI/$NH_3$) m/z 335 (M+H)$^+$.

EXAMPLE 42B

4-{5-[(endo)-8-Methyl-8-aza-bicyclo[3.2.1]oct-3-yloxy]-pyrazin-2-yl}-1H-indole bistosylate The product of Example 42A (40 mg, 0.12 mmol) was treated with p-toluenesulfonic acid monohydrate TsOH.$H_2O$ (Aldrich, 27 mg, 0.15 mmol) in EtOAc/EtOH (v. 4:1, 5 mL) at ambient temperature for 10 hours. The mixture was concentrated under reduced pressure to provide the title compound. $^1$H NMR (300 MHz, $CD_3OD$) δ 2.36 (s, 6H) 2.40-2.48 (m, 4H), 2.50-2.64 (m, 2H), 2.85 (s, 3H), 3.87-4.04 (m, 2H), 5.26-5.63 (m, 1H), 7.19-7.29 (m, 6H), 7.35 (s, 1H), 7.42 (d, J=6.44 Hz, 1H), 7.49 (d, J=8.14 Hz, 1H), 7.71 (d, J=8.48 Hz, 4H), 8.38 (d, J=1.36 Hz, 1H), 8.68 (d, J=1.36 Hz, 1H) ppm. MS (DCI/$NH_3$): m/z 335 (M+H)$^+$. Anal. Calculated for $C_{20}H_{22}N_4O.2.00C_7H_8SO_3.0.50H_2O$: C, 59.37; H, 5.71; N, 8.15. Found: C, 59.56; H, 6.10; N, 8.17.

EXAMPLE 43

6-{5-[(endo)-8-Methyl-8-aza-bicyclo[3.2.1]oct-3-yloxy]-pyrazin-2-yl}-1H-indole tosylate

EXAMPLE 43A

6-{5-[(endo)-8-Methyl-8-aza-bicyclo[3.2.1]oct-3-yloxy]-pyrazin-2-yl}-1H-indole

The product from Example 41C (200 mg, 0.58 mmol), was coupled with 6-indolylboronic acid (Frontier Scientific, 143.3 mg, 0.89 mmol) according to the procedure of Example 9B to provide the title product. $^1$H NMR (300 MHz, $CD_3OD$) δ 1.93-2.05 (m, 2H), 2.08-2.28 (m, 6H), 2.33 (s, 3H), 3.13-3.26 (m, 2H), 5.29 (t, J=4.92 Hz, 1H), 6.47 (d, J=3.05 Hz, 1H), 7.30 (d, J=3.39 Hz, 1H), 7.54-7.68 (m, 2H), 7.96 (s, 1H), 8.19 (d, J=1.36 Hz, 1H), 8.60 (d, J=1.36 Hz, 1H) ppm. MS (DCI/$NH_3$) m/z 335 (M+H)$^+$.

EXAMPLE 43B

6-{5-[(endo)-8-Methyl-8-aza-bicyclo[3.2.1]oct-3-yloxy]-pyrazin-2-yl}-1H-indole tosylate The product of Example 43A (80 mg, 0.24 mmol) was treated with p-toluenesulfonic acid monohydrate TsOH.$H_2O$ (Aldrich, 57 mg, 0.30 mmol) in EtOAc/EtOH (v. 4:1, 5 mL) at ambient temperature for 10 hours. The mixture was concentrated under reduced pressure to provide the title compound. $^1$H NMR (300 MHz, $CD_3OD$) δ 2.36 (s, 3H), 2.37-2.48 (m, 6H), 2.47-2.63 (m, 2H), 2.84 (s, 3H), 3.83-4.02 (m, 2H), 5.27-5.50 (m, 1H), 6.48 (d, J=2.37 Hz, 1H), 7.32 (t, J=1.70 Hz, 1H), 7.53-7.67 (m, 2H), 7.71 (d, J=8.14 Hz, 2H), 7.99 (s, 1H), 8.29 (d, J=1.36 Hz, 1H), 8.64 (d, J=1.36 Hz, 1H) ppm. MS (DCI/$NH_3$): m/z 335 (M+H)$^+$. Anal. Calculated for $C_{20}H_{22}N_4O.1.15C_7H_8SO_3.0.75H_2O$: C, 61.71; H, 6.04; N, 10.26. Found: C, 61.74; H, 5.72; N, 9.87.

EXAMPLE 44

[6-(1H-Indol-6-yl)-pyridin-3-yl]-[(endo)-8-methyl-8-aza-bicyclo[3.2.1]oct-3-yl]-amine trifluoroacetate The product of Example 20A (139 mg, 0.55 mmol) was coupled with indole-6-boronic acid (Frontier Scientific, 165 mg, 1.02 mmol) according to the procedure of Example 8 to provide the title compound. $^1$H NMR (300 MHz, $CD_3OD$) δ 2.18-2.63 (m, 8H) 2.84 (s, 3H) 3.82 (t, J=6.10 Hz, 1H) 3.96 (s, 2H) 6.57 (dd, J=3.05, 0.68 Hz, 1H) 7.41-7.47 (m, 2H) 7.74-7.93 (m, 4H) 8.10 (d, J=9.16 Hz, 1H) ppm. MS (DCI/$NH_3$): m/z 333 (M+H)$^+$. Anal. Calculated for $C_{21}H_{24}N_4.2.45 CF_3CO_2H$: C, 50.85; H, 4.36; N, 9.16. Found: C, 50.72; H, 4.43; N, 9.25.

EXAMPLE 45

5-{6-[(endo)-9-methyl-9-azabicyclo[3.3.1]nonan-3-yloxy]pyridazin-3-yl}-1H-indole trifluoroacetate

EXAMPLE 45A (endo)-9-Methyl-9-azabicyclo[3.3.1]nonan-3-ol (endo)-9-methyl-9-azabicyclo[3.3.1]nonan-3-ol was prepared according to the procedure as described in WO 03062235. $^1$H NMR (300 MHz, $CD_3OD$) δ 1.22-1.32 (m, 2H), 1.35-1.47 (m, 3H), 1.98 (tt, J=13.60, 5.21 Hz, 2H), 2.30-2.56 (m, 6H), 2.87-2.96 (m, 2H), 4.04-4.15 (m, 1H) ppm. MS (DCI/$NH_3$): m/z 156 (M+H)$^+$.

EXAMPLE 45B (endo)-3-(6-chloropyridazin-3-yloxy)-9-methyl-9-azabicyclo[3.3.1]nonane The product of Example 45A (467 mg, 3.0 mmol) was coupled with 3,6-dichloropyridazine (614 mg, 3.3 mmol) according to the procedure of Example 1A. $^1$H NMR (300 MHz, $CD_3OD$) δ 1.59 (ddd, J=14.41, 6.27, 6.10 Hz, 1H), 1.77 (dd, J=14.92, 5.76 Hz, 2H), 2.06-2.28 (m, 4H), 2.52-2.82 (m, 3H), 2.90 (s, 3H), 3.51 (t, J=5.76 Hz, 2H), 5.55 (tt, J=6.91, 1.74 Hz, 1H), 7.26 (d, J=9.16 Hz, 1H), 7.69 (d, J=9.16 Hz, 1H) ppm. MS (DCI/$NH_3$): m/z 268 (M+H)$^+$.

EXAMPLE 45C

5-{6-[(endo)-9-methyl-9-azabicyclo[3.3.1]nonan-3-yloxy]pyridazin-3-yl}-1H-indole trifluoroacetate The product of example 45B (145 mg, 0.54 mmol) was coupled with indole-5-boronic acid (Ryscor, 165 mg, 1.02 mmol) according to the procedure of Example 1B to provide the title compound. $^1$H NMR (300 MHz, $CD_3OD$) δ 1.57-1.81 (m, 2H) 1.95-2.47 (m, 5H) 2.67-2.92 (m, 3H) 2.98-3.06

(m, 3H) 3.65 (t, J=5.09 Hz, 2H) 5.61 (t, J=6.95 Hz, 1H) 6.59 (d, J=3.05 Hz, 1H) 7.34 (d, J=3.05 Hz, 1H) 7.37-7.43 (m, 1H) 7.55 (d, J=8.48 Hz, 1H) 7.74 (dd, J=8.65, 1.86 Hz, 1H) 8.18 (d, J=1.70 Hz, 1H) 8.20-8.27 (m, 1H) ppm. MS (DCI/NH$_3$): m/z 349 (M+H)$^+$. Anal. Calculated for $C_{21}H_{24}N_4O.2.10$ $CF_3CO_2H$: C, 51.48; H, 4.47; N, 9.53. Found: C, 51.31; H, 4.33; N, 9.36.

EXAMPLE 46

(endo)-3-[6-(Benzo[b]thiophen-5-yl)pyridazin-3-yloxy]-9-methyl-9-azabicyclo[3.3.1]nonane trifluoroacetate The product of Example 45B (145 mg, 0.54 mmol) was coupled with the product of 10A (280 mg, 1.02 mmol) according to the procedure of Example 1B to provide the title compound. $^1$H NMR (300 MHz, CD$_3$OD) δ 1.56-1.81 (m, 2H), 1.94-2.48 (m, 5H), 2.68-2.92 (m, 3H), 2.98-3.08 (m, 3H), 3.65 (t, J=5.09 Hz, 2H), 5.66 (t, J=6.95 Hz, 1H), 7.34 (d, J=9.16 Hz, 1H), 7.50 (d, J=5.76 Hz, 1H), 7.68 (d, J=5.76 Hz, 1H), 7.96-8.02 (m, 1H), 8.04-8.10 (m, 1H), 8.20 (d, J=9.49 Hz, 1H), 8.45 (d, J=1.36 Hz, 1H) ppm. MS (DCI/NH$_3$): m/z 366 (M+H)$^+$. Anal. Calculated for $C_{21}H_{23}N_3OS.1.13CF_3CO_2H$: C, 56.51; H, 4.92; N, 8.50. Found: C, 56.56; H, 4.75; N, 8.44.

EXAMPLE 47

5-{5-[(endo)-8-Methyl-8-aza-bicyclo[3.2.1]oct-3-yloxy]-pyrazin-2-yl}-1H-pyrrolo[2,3-b]pyridine bistosylate

EXAMPLE 47A 5-(4,4,5,5-Tetramethyl-[1,3,2]dioxaborolan-2-yl)-1H-pyrrolo[2,3-b]pyridine 5-Bromo-1H-pyrrolo[2,3-b]pyridine (Chemgenx, 0.90 g, 4.57 mmol) was coupled with bis(pinacolato)diboron (Aldrich, 1.27 g, 5.0 mmol) according to the procedure of Example 10A. $^1$H NMR (300 MHz, CDCl$_3$) δ 1.37 (s, 12H) 6.52 (d, J=3.73 Hz, 1H), 7.38 (d, J=3.73 Hz, 1H), 8.34 (d, J=1.36 Hz, 1H), 8.49 (d, J=1.70 Hz, 1H) ppm; m/z 245 (M+H)$^+$.

EXAMPLE 47B

5-{5-[(endo)-8-Methyl-8-aza-bicyclo[3.2.1]oct-3-yloxy]-pyrazin-2-yl}-1H-pyrrolo[2,3-b]pyridine tosylate The product from Example 41C (207 mg, 0.60 mmol), was coupled with the product of Example 47A (200.0 mg, 0.82 mmol) according to the procedure of Example 10B. $^1$H NMR (300 MHz, CD$_3$OD) δ 1.98-2.09 (m, 2H), 2.10-2.32 (m, 6H), 2.40 (s, 3H), 5.32 (t, J=5.09 Hz, 1H), 6.58 (d, J=3.39 Hz, 1H), 7.44 (d, J=3.73 Hz, 1H), 8.25 (d, J=1.36 Hz, 1H), 8.53 (d, J=2.03 Hz, 1H), 8.65 (d, J=1.36 Hz, 1H), 8.78 (d, J=2.03 Hz, 1H) ppm. MS (DCI/NH$_3$) m/z 336 (M+H)$^+$.

EXAMPLE 47C

5-{5-[(endo)-8-Methyl-8-aza-bicyclo[3.2.1]oct-3-yloxy]-pyrazin-2-yl}-1H-pyrrolo[2,3-b]pyridine bistosylate The product of Example 47B (90 mg, 0.27 mmol) was treated with p-toluenesulfonic acid monohydrate TsOH.H$_2$O (Aldrich, 95 mg, 0.5 mmol) in EtOAc/EtOH (v. 4:1, 10 mL) at ambient temperature for 10 hours. The mixture was concentrated under reduced pressure to provide the title compound. $^1$H NMR (300 MHz, CD$_3$OD) δ 2.35 (s, 6H), 2.38-2.45 (m, 2H), 2.45-2.61 (m, 6H), 2.85 (s, 3H), 3.85-4.07 (m, 2H), 5.46 (t, J=4.75 Hz, 1H), 6.97 (d, J=3.39 Hz, 1H), 7.22 (d, J=7.80 Hz, 4H) 7.70 (d, J=8.14 Hz, 4H), 7.76 (d, J=3.73 Hz, 1H), 8.42 (d, J=1.36 Hz, 1H), 8.85 (d, J=1.36 Hz, 1H), 9.04 (d, J=1.70 Hz, 1H), 9.27 (d, J=1.70 Hz, 1H) ppm. MS (DCI/NH$_3$): m/z 336 (M+H)$^+$. Anal. Calculated for $C_{19}H_{21}N_5O.2.17C_7H_8SO_3.1.00H_2O$: C, 56.48; H, 5.59; N, 9.63. Found: C, 56.48; H, 5.37; N, 9.67.

EXAMPLE 48

5-{5-[(exo)-8-Methyl-8-aza-bicyclo[3.2.1]oct-3-yloxy]-pyridin-2-yl}-1H-pyrrolo[2,3-b]pyridine bistosylate

EXAMPLE 48A

5-{5-[(exo)-8-Methyl-8-aza-bicyclo[3.2.1]oct-3-yloxy]-pyridin-2-yl}-1H-pyrrolo[2,3-b]pyridine The product from Example 11A (152 mg, 0.60 mmol), was coupled with the product of Example 47A (200.0 mg, 0.82 mmol) according to the procedure of Example 9B. $^1$H NMR (300 MHz, CD$_3$OD) δ 1.76-1.92 (m, 4H), 2.06-2.20 (m, 4H), 2.36 (s, 3H), 3.18-3.31 (m, 2H), 4.64-4.79 (m, 1H), 6.57 (d, J=3.39 Hz, 1H), 7.43 (d, J=3.73 Hz, 1H), 7.81 (d, J=8.82 Hz, 1H), 8.29 (d, J=3.05 Hz, 1H), 8.45 (d, J=2.03 Hz, 1H), 8.72 (d, J=2.03 Hz, 1H) ppm. MS (DCI/NH$_3$) m/z 335 (M+H)$^+$.

EXAMPLE 48B

5-{5-[(exo)-8-Methyl-8-aza-bicyclo[3.2.1]oct-3-yloxy]-pyridin-2-yl}-1H-pyrrolo[2,3-b]pyridine bistosylate The product of Example 48A (100 mg, 0.30 mmol) was treated with p-toluenesulfonic acid monohydrate TsOH.H$_2$O (Aldrich, 95 mg, 0.5 mmol) in EtOAc/EtOH (v. 4:1, 10 mL) at ambient temperature for 10 hours. The mixture was concentrated under reduced pressure to provide the title compound. $^1$H NMR (300 MHz, CD$_3$OD) δ 2.18-2.47 (m, 2H), 2.15-2.40 (m, 10H), 2.46-2.60 (m, 2H), 2.85 (s, 3H), 3.99-4.06 (m, 2H), 4.95-5.19 (m, 1H), 6.83 (d, J=3.39 Hz, 1H), 7.22 (d, J=8.14 Hz, 4H), 7.66 (d, J=3.39 Hz, 1H), 7.70 (d, J=8.48 Hz, 4H), 8.09 (d, J=8.82 Hz, 1H), 8.48 (d, J=2.71 Hz, 1H), 8.87 (d, J=2.03 Hz, 1H), 8.91 (d, J=2.03 Hz, 1H) ppm. MS (DCI/NH$_3$): m/z 335 (M+H)$^+$. Anal. Calculated for $C_{20}H_{22}N_4O.2.14C_7H_8SO_3.0.50H_2O$: C, 59.01; H, 5.68; N, 7.87. Found: C, 58.88; H, 5.63; N, 7.47.

EXAMPLE 49

5-{5-[(exo)-8-Methyl-8-aza-bicyclo[3.2.1]oct-3-yloxy]-pyridin-3-yl}-1H-indole tri(hydrochloride)

EXAMPLE 49A (exo)-3-(5-Chloro-pyridin-3-yloxy)-8-methyl-8-azabicyclo[3.2.1]octane (endo)-Tropine (Aldrich, 0.56 g, 4.0 mmol), was coupled with 3-chloro-5-hydroxy-pyridine (Aldrich, 0.26 g, 2.0 mmol), in the presence of DIAD (di-isopropyl azadicarboxylate, Aldrich, 0.81 g, 4.0 mmol) and Ph$_3$P (Aldrich, 1.14 g, 4.0 mmol) in THF (anhydrous, Aldrich, 20 mL) at ambient temperature for two days. The reaction mixture was concentrated. The title product was purified by chromatography (SiO$_2$, CH$_2$Cl$_2$:MeOH:NH$_3$.H$_2$O, 90:10:1, R$_f$, 0.45). $^1$H NMR (300 MHz, CD$_3$OD) δ 1.66-1.91 (m, 4H), 1.98-2.19 (m, 4H), 2.33 (s, 3H), 3.22-3.28 (m, 2H), 4.58-4.79 (m, 1H), 7.49 (dd, J=2.37, 1.70 Hz, 1H), 8.11 (d, J=1.70 Hz, 1H), 8.15 (d, J=2.37 Hz, 1H) ppm. MS (DCI/NH$_3$) m/z 255 (M+H)$^+$, 253 (M+H)$^+$.

EXAMPLE 49B

5-{5-[(exo)-8-Methyl-8-aza-bicyclo[3.2.1]oct-3-yloxy]-pyridin-3-yl}-1H-indole

Under N$_2$, the mixture of the product from Example 49A (250 mg, 1.00 mmol) was coupled with 5-Indolylboronic acid (Rsycor, 240.0 mg, 1.50 mmol) according to the procedure of Example 9B. $^1$H NMR (300 MHz, CD$_3$OD) δ 1.71-1.92 (m, 4H), 2.02-2.21 (m, 4H), 2.34 (s, 3H), 3.23-3.30 (m, 2H), 4.63-4.80 (m, 1H), 6.54 (d, J=3.05 Hz, 1H), 7.29 (d, J=3.39 Hz, 1H), 7.38 (dd, J=8.48, 2.03 Hz, 1H), 7.47-7.53 (m, 1H), 7.58-7.64 (m, 1H), 7.83 (d, J=1.36 Hz, 1H), 8.15 (d, J=2.71 Hz, 1H), 8.39 (d, J=1.70 Hz, 1H) ppm. MS (DCI/NH$_3$) m/z 334 (M+H)$^+$.

EXAMPLE 49C

5-{5-[(exo)-8-Methyl-8-aza-bicyclo[3.2.1]oct-3-yloxy]-pyridin-3-yl}-1H-indole tri(hydrochloride)

The product of Example 49B (90 mg, 0.27 mmol) was treated with HCl (Aldrich, 4 M in dioxane, 0.25 mL, 1.0 mmol) in $^i$PrOAc/$^i$PrOH (v. 4:1, 5 mL) at ambient temperature for 2 hours to provide the title compound. $^1$H NMR (300 MHz, CD$_3$OD) δ 2.01-2.66 (m, 8H), 2.83 (s, 3H), 3.92-4.09 (m, 2H), 4.98-5.15 (m, 1H), 6.61 (d, J=3.05 Hz, 1H), 7.33-7.40 (m, 1H), 7.50-7.63 (m, 2H), 8.04-8.10 (m, 2H), 8.44 (d, J=1.70 Hz, 1H), 8.80 (s, 1H) ppm. MS (DCI/NH$_3$): m/z 334 (M+H)$^+$. Anal. Calculated for C$_{21}$H$_{23}$N$_3$O.3.00HCl 4.60H$_2$O: C, 47.98; H, 6.14; N, 7.85. Found: C, 47.62; H, 6.38; N, 7.62.

EXAMPLE 50

5-{5-[(exo)-8-Methyl-8-aza-bicyclo[3.2.1]oct-3-yloxy]-pyrazin-2-yl}-1H-indole tosylate

EXAMPLE 50A (exo)-3-(5-Iodo-pyrazin-2-yloxy)-8-methyl-8-aza-bicyclo[3.2.1]octane Under N$_2$, the mixture of product from 7C (0.42 g, 3.0 mmol) was treated with potassium t-butoxide (Aldrich, 0.32 g, 3.3 mmol) in THF (anhydrous, Aldrich, 50 mL) at ambient temperature for 1 hours. The product of Example 41B (1.00 g, 3.5 mmol) and was added. The mixture was stirred at ambient temperature for 4 hours and quenched with water (5 mL). The mixture was concentrated and the residue was purified by chromatography (150 g SiO$_2$, EtOAc:MeOH:NH$_3$.H$_2$O, 90:10:1, R$_f$, 0.40) to provide the title compound. $^1$H NMR (300 MHz, CD$_3$OD) δ 1.90-2.25 (m, 4H), 2.31-2.60 (m, 4H), 2.84 (s, 3H), 3.94-4.11 (m, 2H), 5.32-5.57 (m, 1H), 8.06 (d, J=1.36 Hz, 1H), 8.42 (d, J=1.36 Hz, 1H) ppm; MS (DCI/NH$_3$) m/z 346 (M+H)$^+$.

EXAMPLE 50B

5-{5-[(exo)-8-Methyl-8-aza-bicyclo[3.2.1]oct-3-yloxy]-pyrazin-2-yl}-1H-indole

The product from Example 50A (200 mg, 0.58 mmol), was coupled with 5-indolylboronic acid (Rsycor, 143.3 mg, 0.89 mmol) according to the procedure of Example 9B. $^1$H NMR (300 MHz, CD$_3$OD) δ 1.95-2.17 (m, 2H), 2.16-2.31 (m, 2H), 2.36-2.47 (m, 2H), 2.48-2.67 (m, 2H), 2.85 (s, 3H), 3.90-4.17 (m, 1H), 5.36-5.69 (m, 1H), 6.53 (d, J=3.39 Hz, 1H), 7.29 (d, J=3.05 Hz, 1H), 7.48 (d, J=8.48 Hz, 1H) 7.69 (dd, J=8.48, 1.70 Hz, 1H), 8.13 (s, 1H) 8.20 (d, J=1.36 Hz, 1H), 8.62 (d, J=1.36 Hz, 1H) ppm. MS (DCI/NH$_3$) m/z 335 (M+H)$^+$.

EXAMPLE 50C

5-{5-[(exo)-8-Methyl-8-aza-bicyclo[3.2.1]oct-3-yloxy]-pyrazin-2-yl}-1H-indole tosylate The product of Example 50B (170 mg, 0.50 mmol) was treated with p-toluenesulfonic acid monohydrate TsOH.H$_2$O (Aldrich, 100 mg, 0.51 mmol) in EtOAc/EtOH (v. 4:1, 5 mL) at ambient temperature for 10 hours. The mixture was concentrated under reduced pressure to provide the title compound. $^1$H NMR (300 MHz, CD$_3$OD) δ 2.01-2.15 (m, 2H), 2.16-2.30 (m, 2H), 2.36 (s, 3H), 2.39-2.49 (m, 2H), 2.52-2.67 (m, 2H), 2.84 (s, 3H), 3.96-4.13 (m, 2H), 5.43-5.70 (m, 1H), 7.23 (d, J=8.14 Hz, 2H), 7.30 (s, 1H), 7.49 (d, J=8.48 Hz, 1H), 7.62-7.75 (m, 4H), 8.12 (s, 1H), 8.22 (d, J=1.36 Hz, 1H), 8.68 (d, J=1.36 Hz, 1H) ppm. MS (DCI/NH$_3$): m/z 335 (M+H)$^+$.

EXAMPLE 51

4-{5-[(exo)-8-Methyl-8-aza-bicyclo[3.2.1]oct-3-yloxy]-pyrazin-2-yl}-1H-indole tosylate

EXAMPLE 51A

4-{5-[(exo)-8-Methyl-8-aza-bicyclo[3.2.1]oct-3-yloxy]-pyrazin-2-yl}-1H-indole

The product from Example 50A (200 mg, 0.58 mmol), was coupled with 4-indolylboronic acid (Apollo, 143.3 mg, 0.89 mmol) according to the procedure of Example 9B. $^1$H NMR (300 MHz, CD$_3$OD) δ 2.02-2.28 (m, 4H), 2.34-2.48 (m, 2H), 2.50-2.65 (m, 2H), 2.86 (s, 3H), 3.96-4.07 (m, 2H), 5.45-5.68 (m, 1H), 6.82 (d, J=4.07 Hz, 1H), 7.23 (t, J=7.60 Hz 1H), 7.35 (d, J=3.39 Hz, 1H), 7.41 (d, J=6.44 Hz, 1H), 7.48 (d, J=8.14 Hz, 1H), 8.29 (d, J=1.36 Hz, 1H), 8.65 (d, J=1.36 Hz, 1H) ppm. MS (DCI/NH$_3$) m/z 335 (M+H)$^+$.

EXAMPLE 51B

4-{5-[(exo)-8-Methyl-8-aza-bicyclo[3.2.1]oct-3-yloxy]-pyrazin-2-yl}-1H-indole tosylate The product of Example 51A (120 mg, 0.36 mmol) was treated with p-toluenesulfonic acid monohydrate TsOH.H$_2$O (Aldrich, 68 mg, 0.36 mmol) in EtOAc/EtOH (v. 4:1, 5 mL) at ambient temperature for 10 hours. The mixture was concentrated under reduced pressure to provide the title compound. $^1$H NMR (300 MHz, CD$_3$OD) δ 2.02-2.17 (m, 2H), 2.18-2.32 (m, 2H), 2.36 (s, 3H), 2.38-2.50 (m, 2H), 2.52-2.69 (m, 2H), 2.85 (s, 3H), 4.00-4.11 (m, 2H), 7.17-7.28 (m, 1H), 7.35 (s, 1H), 7.42 (d, J=7.12 Hz, 1H), 7.49 (d, J=8.14 Hz, 1H), 7.70 (d, J=8.14 Hz, 1H), 8.30 (d, J=1.70 Hz, 1H), 8.67 (d, J=1.36 Hz, 1H) ppm. MS (DCI/NH$_3$): m/z 335 (M+H)$^+$.

EXAMPLE 52

6-{5-[(exo)-8-Methyl-8-aza-bicyclo[3.2.1]oct-3-yloxy]-pyrazin-2-yl}-1H-indole tosylate

EXAMPLE 52A

6-{5-[(exo)-8-Methyl-8-aza-bicyclo[3.2.1]oct-3-yloxy]-pyrazin-2-yl}-1H-indole

The product from Example 41C (200 mg, 0.58 mmol), was coupled with 6-indolylboronic acid (Frontier Scientific, 143.3 mg, 0.89 mmol) according to the procedure of Example 9B. $^1$H NMR (300 MHz, CD$_3$OD) δ 1.97-2.16 (m, 2H), 2.14-2.26 (m, 2H), 2.31-2.65 (m, 4H), 2.81 (s, 3H), 3.84-4.05 (m, 2H), 5.33-5.71 (m, 1H), 6.47 (d, J=3.05 Hz, 1H), 7.31 (d, J=3.05 Hz, 1H), 7.48-7.73 (m, 2H), 7.99 (s, 1H), 8.20 (d, J=1.36 Hz, 1H), 8.63 (d, J=1.36 Hz, 1H) ppm. MS (DCI/NH$_3$) m/z 335 (M+H)$^+$.

EXAMPLE 52B

6-{5-[(exo)-8-Methyl-8-aza-bicyclo[3.2.1]oct-3-yloxy]-pyrazin-2-yl}-1H-indole tosylate The product of Example 52A (90 mg, 0.27 mmol) was treated with p-toluenesulfonic acid monohydrate TsOH.H$_2$O (Aldrich, 57 mg, 0.30 mmol) in EtOAc/EtOH (v. 4:1, 5 mL) at ambient temperature for 10 hours. The mixture was concentrated under reduced pressure to provide the title compound. $^1$H NMR (300 MHz, CD$_3$OD) δ 2.01-2.14 (m, 2H), 2.16-2.31 (m, 2H), 2.36 (s, 3H), 2.39-2.51 (m, 2H), 2.50-2.65 (m, 2H), 2.84 (s, 3H), 3.98-4.08 (m, 2H), 5.41-5.68 (m, 1H), 6.48 (d, J=2.37 Hz, 1H), 7.23 (d, J=7.80 Hz, 2H), 7.32 (s, 1H), 7.55-7.67 (m, 2H), 7.71 (d, J=8.48 Hz, 2H), 7.99 (s, 1H), 8.22 (d, J=1.36 Hz, 1H), 8.65 (d, J=1.36 Hz, 1H) ppm. MS (DCI/NH$_3$): m/z 335 (M+H)$^+$.

EXAMPLE 53

(endo)-N-(5-(1H-Indol-5-yl)pyridin-3-yl)-8-methyl-8-azabicyclo[3.2.1]octan-3-amine

EXAMPLE 53A (endo)-N-(5-Bromopyridin-3-yl)-8-methyl-8-azabicyclo[3.2.1]octan-3-amine 8-Methyl-8-azabicyclo[3.2.1]octan-3-one (Aldrich, 695 mg, 5.0 mmol) reacted with bromopyridin-3-amine (950 mg, 5.5 mmol) according to the procedure of Example 20A to give the title compound (650 mg, yield, 44%). $^1$H NMR (300 MHz, CD$_3$OD) δ 1.54-2.25 (m, 8H), 2.29 (s, 3H), 3.16 [s (broad), 2H], 3.50 (t, J=6.61 Hz, 1H), 7.08 (t, J=2.20 Hz, 1H), 7.79 (d, J=1.70 Hz, 1H), 7.85 (d, J=2.37 Hz, 1H) ppm; MS (DCI/NH$_3$): m/z 298 (M+H)$^+$, 296 (M+H)$^+$.

EXAMPLE 53B (endo)-N-(5-(1H-Indol-5-yl)pyridin-3-yl)-8-methyl-8-azabicyclo[3.2.1]octan-3-amine p-tosylate The product of Example 53A (150 mg, 0.5 mmol) was coupled with indole-5-boronic acid (Frontier, 150 mg, 0.93 mmol) according to the procedure of Example 9B to provide the free base of the title compound (82 mg, yield, 50%), which was treated with p-toluenesulfonic acid hydrate (Aldrich, 47 mg, 0.25 mmol) in EtOAc/EtOH (v. 10:1, 5 mL) at room temperature for 16 hours. The precipitate was collected and dried to give the title compound (99.3 mg, yield, 67.2%). $^1$H NMR (300 MHz, CD$_3$OD) δ 2.15-2.30 (m, 2H), 2.30-2.42 (m, 5.5H), 2.42-2.63 (m, 4H), 2.82 (s, 3H), 3.81 (t, J=5.9 Hz, 1H), 3.93 [s (broad), 2H), 6.54 (d, J=2.4 Hz, 1H), 7.21 (d, J=8.1 Hz, 3H), 7.32 (d, J=3.1 Hz, 1H), 7.39 (dd, J=8.4, 1.7 Hz, 1H), 7.47-7.59 (m, 2H), 7.70 (d, J=8.5 Hz, 3H), 7.86 (d, J=1.7 Hz, 1H), 7.90 (d, J=2.4 Hz, 1H), 8.23 (d, J=1.7 Hz, 1H) ppm. MS DCI/NH$_3$): m/z 333 (M+H)$^+$. Anal. Calculated for C$_{21}$H$_{24}$N$_4$.1.50C$_7$H$_8$O$_3$S.1.20H$_2$O: C, 61.78; H, 6.32; N, 9.15. Found: C, 61.78; H, 6.19; N, 8.99.

EXAMPLE 54

(endo)-N-(5-(1H-Indol-4-yl)pyridin-3-yl)-8-methyl-8-azabicyclo[3.2.1]octan-3-amine p-tosylate

EXAMPLE 54A (endo)-N-(5-(1H-Indol-4-yl)pyridin-3-yl)-8-methyl-8-azabicyclo[3.2.1]octan-3-amine The product of Example 53A (150 mg, 0.5 mmol) was coupled with indole-4-boronic acid (Frontier, 150 mg, 0.93 mmol) according to the procedure of Example 9B to provide the title compound (80 mg, yield, 48%), $^1$H NMR (300 MHz, CD$_3$OD) δ 1.78-1.96 (m, 2H), 2.05-2.16 (m, 4H), 2.17-2.30 (m, 2H), 2.33 (s, 3H), 3.21 [s (broad), 2H], 3.63 (t, J=6.8 Hz, 1H), 6.57 (d, J=3.4 Hz, 1H), 7.08 (d, J=7.1 Hz, 1H), 7.15-7.26 (m, 2H), 7.31 (d, J=3.1 Hz, 1H), 7.42 (d, J=7.8 Hz, 1H), 7.89 (d, J=2.7 Hz, 1H), 8.05 (d, J=1.7 Hz, 1H) ppm; MS DCI/NH$_3$): m/z 333 (M+H)$^+$.

EXAMPLE 54B (endo)-N-(5-(1H-Indol-4-yl)pyridin-3-yl)-8-methyl-8-azabicyclo[3.2.1]octan-3-amine p-tosylate The product of Example 54A (80 mg, 0.24 mmol) was treated with p-toluenesulfonic acid hydrate (Aldrich, 47 mg, 0.25 mmol) in EtOAc/EtOH (v. 10:1, 5 mL) at room temperature for 16 hours. The precipitate was collected and dried to give the title compound (85.3 mg, yield, 58.5%). $^1$H NMR (300 MHz, CD$_3$OD) δ 2.17-2.31 (m, 2H), 2.31-2.41 (m, 5.8H), 2.41-2.60 (m, 4H), 2.82 (s, 3H), 3.79 (t, J=5.9 Hz, 1H), 3.93 [s (broad), 2H), 7.16 (dd, J=7.5, 1.0 Hz, 1H), 7.21-7.27 (m, 5.2H), 7.37 (d, J=3.1 Hz, 1H), 7.50 (d, J=8.1 Hz, 1.0H), 7.62-7.66 (m, 1.0H), 7.70 (d, J=8.1 Hz, 3.2H), 7.99 (d, J=2.4 Hz, 1H), 8.24 (d, J=1.4 Hz, 1H) ppm. MS DCI/NH$_3$): m/z 333 (M+H)$^+$. Anal. Calculated for C$_{21}$H$_{24}$N$_4$.1.60C$_7$H$_8$O$_3$S.1.20H$_2$O: C, 61.43; H, 6.28; N, 8.90. Found: C, 61.72; H, 6.26; N, 8.64.

EXAMPLE 55

(endo)-N-(5-(1H-Indol-6-yl)pyridin-3-yl)-8-methyl-8-azabicyclo[3.2.1]octan-3-amine p-tosylate

EXAMPLE 55A (endo)-N-(5-(1H-Indol-6-yl)pyridin-3-yl)-8-methyl-8-azabicyclo[3.2.1]octan-3-amine The product of Example 53A (150 mg, 0.5 mmol) was coupled with indole-6-boronic acid (Frontier, 150 mg, 0.93 mmol) according to the procedure of Example 9B to provide the free base of the title compound (102 mg, yield, 60%). $^1$H NMR (300 MHz, CD$_3$OD) δ 1.80-1.98 (m, 2H), 2.06-2.19 (m, 4H), 2.19-2.32 (m, 2H), 2.35 (s, 3H), 3.24 [s (broad), 2H), 3.64 (t, J=6.8 Hz, 1H), 6.47 (d, J=3.4 Hz, 1H), 7.16-7.21 (m, 1H), 7.22-7.34 (m, 2H), 7.57-7.67 (m, 2H), 7.83 (d, J=2.7 Hz, 1H), 8.06 (d, J=2.0 Hz, 1H) ppm; MS DCI/NH$_3$): m/z 333 (M+H)$^+$.

EXAMPLE 55B (endo)-N-(5-(1H-Indol-6-yl)pyridin-3-yl)-8-methyl-8-azabicyclo[3.2.1]octan-3-amine p-tosylate The product of Example 55A (102 mg, 0.3 mmol) was treated with p-toluenesulfonic acid hydrate (Aldrich, 57 mg, 0.30 mmol) in EtOAc/EtOH (v. 10:1, 5 mL) at room temperature for 16 hours. The precipitate was collected and dried to give the title compound (137.2 mg, yield, 59.4%). $^1$H NMR (300 MHz, CD$_3$OD) 2.16-2.64 (m, 12.2H), 2.82 (s, 3H), 3.78 (t, J=6.3 Hz, 1H), 3.92 [s (broad), 2H), 6.48 (d, J=4.1 Hz, 1H), 7.22 (d, J=7.8 Hz, 2.8H), 7.27 (dd, J=8.1, 1.7 Hz, 1H), 7.30 (d, J=3.1 Hz, 1H), 7.31-7.34 (m, 1H), 7.61-7.66 (m, 2H), 7.70 (d, J=8.1 Hz, 2.8H), 7.88 (d, J=2.4 Hz, 1H), 8.17 (d, J=1.7 Hz, 1H) ppm. MS DCI/NH$_3$): m/z 333 (M+H)$^+$. Anal. Calculated for C$_{21}$H$_{24}$N$_4$.1.40C$_7$H$_8$O$_3$S.0.70H$_2$O: C, 63.11; H, 6.29; N, 9.56. Found: C, 63.17; H, 6.61; N, 9.43.

EXAMPLE 56

(endo)-N-{5-[2-(trifluoromethyl)-1H-indol-5-yl]pyridin-3-yl}-8-Methyl-8-azabicyclo[3.2.1]octan-3-amine fumarate The product of Example 9A (110 mg, 0.4 mmol) was coupled with the product of Example 7A (300 mg, 0.97 mmol) according to the procedure described in Example 9B to provide the free base of the title compound (38 mg, yield, 22.5%), which was (38 mg, 0.09 mmol) was then treated with fumaric acid (12 mg, 0.1 mmol) in EtOAc/EtOH (v. 10:1, 5 mL) at room temperature for 16 hours. The precipitate was filtered and dried to give the title compound (50.4 mg, yield, 99%). $^1$H NMR (300 MHz, CD$_3$OD) δ 2.28-2.37 (m, 4H), 2.42-2.57 (m, 4H), 2.84 (s, 3H), 3.02 [s(broad), 2H], 4.80-4.90 (m, 1H) 6.72 (s, 2.6H), 6.97 (s, 1H), 7.47-7.57 (m, 2H), 7.85 (d, J=8.8 Hz, 2H), 8.17 (s, 1H) 8.30 (s, 1H) ppm. MS DCI/NH$_3$): m/z 402 (M+H)$^+$. Anal. Calculated for C$_{22}$H$_{22}$F$_3$N$_4$O.1.30C$_4$O$_4$H$_4$: C, 59.15; H, 4.96; N, 7.61. Found: C, 59.29; H, 5.07; N, 7.37.

EXAMPLE 57

5-{5-[(endo)-8-Methyl-8-azabicyclo[3.2.1]octan-3-yloxy]pyridin-2-yl}-1H-pyrrolo[2,3-b]pyridine tosylate

EXAMPLE 57A

5-{5-[(endo)-8-Methyl-8-aza-bicyclo[3.2.1]oct-3-yloxy]-pyridin-2-yl}-1H-pyrrolo[2,3-b]pyridine The product of Example 9A (200 mg, 0.80 mmol), was coupled with the product of Example 47A (244.0 mg, 1.0 mmol) according to the procedure of Example 9B. to provide the title compound (190 mg, yield, 71%). $^1$H NMR (300 MHz, CD$_3$OD) δ 1.93-2.27 (m, 8H), 2.33 (s, 3H), 3.20 [s (broad.), 2H], 4.69 (t, J=5.1 Hz, 1H), 6.57 (d, J=3.4 Hz, 1H), 7.39-7.48 (m, 2H), 7.83 (d, J=8.5 Hz, 1H), 8.25 (d, J=2.7 Hz, 1H), 8.46 (d, J=2.0 Hz, 1H), 8.73 (d, J=2.4 Hz, 1H) ppm. MS (DCI/NH$_3$) m/z 335 (M+H)$^+$.

EXAMPLE 57B

5-{5-[(endo)-8-Methyl-8-aza-bicyclo[3.2.1]oct-3-yloxy]-pyridin-2-yl}-1H-pyrrolo[2,3-b]pyridine tosylate The product of Example 48A (80 mg, 0.24 mmol) was treated with p-toluenesulfonic acid monohydrate TsOH.H$_2$O (Aldrich, 57 mg, 0.3 mmol) in EtOAc/EtOH (v. 4:1, 10 mL) at ambient temperature for 10 hours. The precipitated solid was filtered and dried to provide the title compound (100 mg, yield, 79.6%). $^1$H NMR (300 MHz, CD$_3$OD) δ 2.27-2.69 (m, 11H), 2.84 (s, 3H), 3.84-4.08 (m, 2H), 4.84-4.94 (m, 1H), 6.62 (d, J=3.4 Hz, 1H), 7.23 (d, J=8.1 Hz, 2H), 7.47 (d, J=3.7 Hz, 1H), 7.56 (dd, J=8.8, 3.1 Hz, 1H), 7.71 (d, J=8.1 Hz, 2H), 7.92 (d, J=8.8 Hz, 1H), 8.36 (d, J=2.7 Hz, 1H), 8.56 (d, J=2.0 Hz, 1H), 8.77 (d, J=2.0 Hz, 1H) ppm. MS (DCI/NH$_3$): m/z 335 (M+H)$^+$. Anal. Calculated for C$_{20}$H$_{22}$N$_4$O.1.10C$_7$H$_8$SO$_3$.0.80H$_2$O: C, 61.81; H, 6.07; N, 10.41. Found: C, 62.15; H, 5.92; N, 10.05.

EXAMPLE 58

5-{5-[(endo)-8-Methyl-8-azabicyclo[3.2.1]octan-3-yloxy]pyridin-2-yl}indolin-2-one bis(hydrochloric acid)

EXAMPLE 58A 5-(4,4,5,5-Tetramethyl-1,3,2-dioxaborolan-2-yl)indolin-2-one

Under N$_2$, 5-Bromoindolin-2-one (Aldrich, 2.11 g, 10.0 mmol) was coupled with bis(pinacolato)dibon (Frontier Scientific, 3.05 g, 12 mmol) in the presence of KOAc (Aldrich, 1.50 g, 15.0 mmol) under the catalysis of PdCl$_2$(dppf). CH$_2$Cl$_2$ (Aldrich, 163 mg, 0.2 mmol) in anhydrous dioxane (Aldrich, 50 mL) at 85° C. for 15 hours. After the reaction was completed, it was cooled down to ambient temperature and diluted with EtOAc (100 mL). The mixture was then washed with brine (2×10 mL) and concentrated. The residue was purified with chromatography on silica gel (EtOAc/hexanes, v. 1:1, R$_f$=0.5) to provide the title compound (2.43 g, yield, 93.8%). $^1$H NMR (300 MHz, CD$_3$OD) δ 1.24 (s, 12H), 3.51 (s, 2H), 6.88 (d, J=8.5 Hz, 1H), 7.52-7.75 (m, 2H) ppm. MS (DCI/NH$_3$): m/z 260 (M+H)$^+$.

EXAMPLE 58B

5-{5-[(endo)-8-Methyl-8-azabicyclo[3.2.1]octan-3-yloxy]pyridin-2-yl}indolin-2-one The product of Example 9A (200 mg, 0.80 mmol), was coupled with the product of Example 58A (260 mg, 1.0 mmol) according to the procedure of Example 9B. to provide the title compound (130 mg, yield, 46.4%). $^1$H NMR (300 MHz, CD$_3$OD) δ 1.93-2.04 (m, 2H), 2.06-2.15 (m, J=2.4 Hz, 4H), 2.14-2.25 (m, 2H), 2.33 (s, 3H), 3.20 [s (broad), 2H], 4.67 (t, J=5.1 Hz, 1H), 6.96 (d, J=8.1 Hz, 1H), 7.38 (dd, J=8.8, 3.1 Hz, 1H), 7.69-7.80 (m, 3H), 8.18 (d, J=3.1 Hz, 1H) ppm. MS (DCI/NH$_3$) m/z 350 (M+H)$^+$.

EXAMPLE 58C

5-{5-[(endo)-8-Methyl-8-azabicyclo[3.2.1]octan-3-yloxy]pyridin-2-yl}indolin-2-one bis(hydrochloric acid)

The product of Example 48A (80 mg, 0.24 mmol) was treated with p-toluenesulfonic acid monohydrate TsOH.H$_2$O (Aldrich, 57 mg, 0.3 mmol) in EtOAc/EtOH (v. 4:1, 10 mL) at ambient temperature for 10 hours. The precipitated solid was filtered and dried to provide the title compound (100 mg, yield, 79.6%). $^1$H NMR (300 MHz, CD$_3$OD) δ 2.31-2.67 (m, 8H), 2.85 (s, 3H), 3.68 (s, 2H), 3.90-4.08 (m, 2H), 5.03 (t, J=4.6 Hz, 1H), 7.14 (d, J=9.2 Hz, 1H), 7.73-7.82 (m, 2H), 8.22-8.34 (m, 2H), 8.53 (d, J=2.4 Hz, 1H) ppm. MS (DCI/NH$_3$) m/z 350 (M+H)$^+$. Anal. Calculated for C$_{21}$H$_{23}$N$_3$O$_2$.2.00 HCl.3.0H$_2$O: C, 52.95; H, 6.56; N, 8.82. Found: C, 52.67; H, 6.47; N, 8.62.

EXAMPLE 59

5-{5-[(endo)-8-Azabicyclo[3.2.1]octan-3-yloxy]pyridin-2-yl}-1H-indole bis(hydrochloric acid)

EXAMPLE 59A (endo)-3-(6-Chloropyridin-3-yloxy)-8-azabicyclo[3.2.1]octane

To a solution of the product of Example 9A (253 mg, 1.0 mmol) in anhydrous 1,2-dichloroethane (Aldrich, 10 mL) was added 1-chloroethyl carbonochloridate (Aldrich, 286 mg, 2.0 mmol). The mixture was heated to reflux for 15 hours. It was then concentrated, the residue was diluted with 5 mL of methanol. The solution was stirred at 65° C. for 1 h. and then concentrated. The residue was purified with chromatography on silica gel (CH$_2$Cl$_2$:MeOH:NH$_3$.H$_2$O, v. 90:10:2, R$_f$=0.1) to give the title compound (180 mg, yield, 75%). $^1$H NMR (300 MHz, CD$_3$OD) δ 2.03-2.62 (m, 8H), 4.01-4.14 (m, 2H), 4.75-4.82 (m, 1H), 7.37-7.42 (m, 1H), 7.44 (d, J=3.1 Hz, 1H), 8.03-8.13 (m, 1H) ppm. MS (DCI/NH$_3$) m/z 241 (M+H)$^+$, 239 (M+H)$^+$.

EXAMPLE 59B

5-{5-[(endo)-8-Azabicyclo[3.2.1]octan-3-yloxy]pyridin-2-yl}-1H-indole

The product of Example 59A (180 mg, 0.75 mmol), was coupled with 1H-indol-5-ylboronic acid (160 mg, 1.0 mmol) according to the procedure of Example 9B. to provide the title compound (120 mg, yield, 50.1%). $^1$H NMR (300 MHz, CD$_3$OD) δ 1.77-1.94 (m, 2H), 1.96-2.07 (m, 2H), 2.07-2.30 (m, 4H), 3.46-3.59 (m, 2H), 4.73 (t, J=4.9 Hz, 1H), 6.51 (d, J=4.1 Hz, 1H), 7.26 (d, J=3.1 Hz, 1H), 7.39 (dd, J=8.8, 3.1 Hz, 1H), 7.45 (d, J=8.5 Hz, 1H), 7.62 (dd, J=8.5, 1.7 Hz, 1H), 7.77 (d, J=8.8 Hz, 1H), 8.03 (d, J=1.7 Hz, 1H), 8.17 (d, J=2.7 Hz, 1H) ppm. MS (DCI/NH$_3$) m/z 320 (M+H)$^+$.

EXAMPLE 59C

5-{5-[(endo)-8-Azabicyclo[3.2.1]octan-3-yloxy]pyridin-2-yl}-1H-indole bis(hydrochloric acid)

The product of Example 59B (120 mg, 0.38 mmol) was treated with HCl (4 M, in dioxane, 0.2 mL, 0.8 mmol) in EtOAc (5.0 mL) at ambient temperature for 10 hours. The precipitated solid was filtered and dried to provide the title compound (130 mg, yield, 79.6%). $^1$H NMR (300 MHz, CD$_3$OD) δ 2.09-2.26 (m, 2H), 2.28-2.43 (m, 2H), 2.40-2.59 (m, 4H), 4.02-4.23 (m, 2H), 5.02 (t, J=4.4 Hz, 1H), 6.65 (d, J=3.1 Hz, 1H), 7.42 (d, J=3.4 Hz, 1H), 7.57-7.71 (m, 2H), 8.15 (s, 1H), 8.19 (dd, J=9.1, 2.7 Hz, 1H), 8.29 (d, J=9.1 Hz, 1H), 8.44 (d, J=2.7 Hz, 1H) ppm. MS (DCI/NH$_3$) m/z 320 (M+H)$^+$. Anal. Calculated for C$_{20}$H$_{21}$N$_3$O.2.00HCl 1.18H$_2$O: C, 58.08; H, 6.18; N, 10.16. Found: C, 57.73; H, 6.37; N, 9.95.

EXAMPLE 60

(1R,3r,5S,8s)-3-(6-(1H-Indol-5-yl)pyridin-3-yloxy)-8-methyl-8-azabicyclo[3.2.1]octane 8-oxide 3-Chlorobenzoperoxoic acid (Aldrich, 70-75%, 240 mg, 1.0 mmol) was added to a solution of product of example 9B (333 mg, 1.0 mmol) in MeOH (10 mL). It was then stirred at ambient temperature for 4 hours. The solution was directly purified by preparative HPLC [Gilson, column, Xterra® 5 μm, 40×100 mm. Eluting Solvent, MeCN/H$_2$O (0.1 M aqueous ammonium bicarbonate, adjusted to pH 10 with ammonium hydroxide) (v. 10/90 to 75/25 over 20 minutes, Flow rate of 40 mL/minute, uv detector set to 250 nm]. The fractions with lower rention time were collected and concentrated under reduced pressure to provide the title compound (130 mg, yield, 37.2%). $^1$H NMR (300 MHz, CD$_3$OD) δ 2.19-2.42 (m, 4H), 2.45-2.74 (m, 4H), 3.34 (s, 3H), 3.57-3.70 (m, 2H), 4.72 (t, J=5.3 Hz, 1H), 6.52 (d, J=2.4 Hz, 1H), 7.27 (d, J=3.1 Hz, 1H), 7.40-7.52 (m, 2H), 7.64 (dd, J=8.5, 1.7 Hz, 1H), 7.80 (d, J=8.8 Hz, 1H), 8.05 (d, J=2.0 Hz, 1H), 8.23 (d, J=3.1 Hz, 1H) ppm; MS (DCI/NH$_3$) m/z 350 (M+H)$^+$.

EXAMPLE 61

(1R,3r,5S,8r)-3-(6-(1H-Indol-5-yl)pyridin-3-yloxy)-8-methyl-8-azabicyclo[3.2.1]octane 8-oxide 3-Chlorobenzoperoxoic acid (Aldrich, 70-75%, 240 mg, 1.0 mmol) was added to a solution of product of example 9B (333 mg, 1.0 mmol) in MeOH (10 mL). It was then stirred at ambient temperature for 4 hours. The solution was directly purified by preparative HPLC [Gilson, column, Xterra® 5 μm, 40×100 mm. Eluting Solvent, MeCN/H$_2$O (0.1 M aqueous ammonium bicarbonate, adjusted to pH 10 with ammonium hydroxide) (v. 10/90 to 75/25 over 20 minutes, Flow rate of 40 mL/minute, uv detector set to 250 nm]. The fractions with higher rention time were collected and concentrated under reduced pressure to provide the title compound (110 mg, yield, 31.5%). $^1$H NMR (300 MHz, CD$_3$OD) δ 1.96-2.07 (m, 2H), 2.19-2.37 (m, 2H), 2.44-2.59 (m, 2H), 3.06 (dt, J=15.3, 4.2 Hz, 2H), 3.24 (s, 3H), 3.47-3.59 (m, 2H), 4.71-4.81 (m, 1H), 6.52 (d, J=3.1 Hz, 1H), 7.27 (d, J=3.4 Hz, 1H), 7.42-7.50 (m, 2H), 7.64 (dd, J=8.5, 1.7 Hz, 1H), 7.80 (d, J=8.8 Hz, 1H), 8.05 (d, J=1.7 Hz, 1H), 8.24 (d, J=3.1 Hz, 1H) ppm; MS (DCI/NH$_3$) m/z 350 (M+H)$^+$.

EXAMPLE 62

4-{5-[(endo)-8-Azabicyclo[3.2.1]octan-3-yloxy]pyridin-2-yl}-1H-indole trifluoroacetate The product of Example 59A (120 mg, 0.50 mmol), was coupled with 1H-indol-4-ylboronic acid (Frontier, 121 mg, 0.75 mmol) according to the procedure of Example 9B. The crude mixture was purified with preparative HPLC (Gilson, column, Xterra® 5 µm, 40×100 mm. Eluting Solvent, MeCN/H$_2$O containing 0.1% v. TFA (90% to 10% over 25 minutes, Flow rate of 40 mL/minute, uv detector set to 254 nm). The fractions containing the desired product were collected and concentrated under reduced pressure and the residue was stirred in ether/ethanol (v. 10/1, 5 mL) at ambient temperature for 16 hours to provide the title compound. (80 mg, yield, 29.2%). $^1$H NMR (300 MHz, CD$_3$OD) δ 2.06-2.24 (m, 2H), 2.25-2.60 (m, 6H), 4.00-4.33 (m, 2H), 4.90-5.02 (m, 1H), 6.72 (dd, J=3.39, 1.02 Hz, 1H), 7.25-7.32 (m, 1H), 7.34-7.39 (m, 1H), 7.43 (d, J=3.05 Hz, 1H), 7.58 (dt, J=7.80, 1.02 Hz, 1H), 7.93 (dd, J=8.99, 2.88 Hz, 1H), 8.11 (d, J=8.82 Hz, 1H), 8.46 (d, J=2.71 Hz, 1H) ppm. MS (DCI/NH$_3$) m/z 320 (M+H)$^+$. Anal. Calc. for C$_{20}$H$_{21}$N$_3$O.2.00CF$_3$CO$_2$H.0.50H$_2$O: C, 51.80; H, 4.35; N, 7.55. Found: C, 51.84; H, 4.28; N, 7.30.

EXAMPLE 63

5-{5-[(exo)-8-Azabicyclo[3.2.1]octan-3-yloxy]pyridin-2-yl}-1H-indole bis(hydrochloric acid)

EXAMPLE 63A (exo)-3-(6-Chloropyridin-3-yloxy)-8-azabicyclo[3.2.1]octane

To a solution of the product of Example 11A (2.52 g, 9.97 mmol) in 1,2-dichloroethane (25 ml) (anhydrous) was added 1-chloroethyl carbonochloridate (5.54 ml, 49.9 mmol). The mixture was then heated to 100° C. for 50 h. It was then cooled down to ambient temperature, 25 mL of MeOH was added. The mixture was then heated to reflux for 1 hour. It is concentrated and the crude was purified with chromatography on silica gel (CH$_2$Cl$_2$:MeOH:NH$_3$.H$_2$O, v. 90:10:2, R$_f$=0.15) to give the title compound (180 mg, yield, 75%). $^1$H NMR (300 MHz, CD$_3$OD) δ 1.56-1.71 (m, 2H), 1.74-1.94 (m, 4H), 2.01-2.26 (m, 2H), 3.46-3.73 (m, 2H), 4.58-4.76 (m, 1H), 7.32 (d, J=8.1 Hz, 1H), 7.43 (dd, J=8.8, 3.0 Hz, 1H), 8.01 (d, J=2.7 Hz, 1H) ppm. MS (DCI/NH$_3$) m/z 241 (M+H)$^+$, 239 (M+H)$^+$.

EXAMPLE 63B

5-{5-[(exo)-8-Azabicyclo[3.2.1]octan-3-yloxy]pyridin-2-yl}-1H-indole

The product of Example 63A (0.24 g, 1.0 mmol) was coupled with 1H-indol-5-ylboronic acid (Frontier, 0.241 g, 1.50 mmol) according to the procedure of Example 9B to provide the title compound (0.25 g, yield, 79%). $^1$H NMR (300 MHz, CD$_3$OD) δ 1.69-1.83 (m, 2H), 1.86-1.99 (m, 4H), 2.18-2.32 (m, 2H), 3.67-3.87 (m, 2H), 4.69-4.82 (m, 1H), 6.52 (d, J=2.37 Hz, 1H), 7.27 (d, J=3.05 Hz, 1H), 7.45 (dt, J=8.48, 0.85 Hz, 1H), 7.49 (dd, J=8.82, 3.05 Hz, 2H), 7.62 (dd, J=8.48, 1.70 Hz, 2H), 7.76 (d, J=8.14 Hz, 2H), 8.03 (d, J=1.36 Hz, 2H), 8.22 (d, J=2.37 Hz, 1H) ppm; MS (DCI/NH$_3$) m/z 320 (M+H)$^+$.

EXAMPLE 63C

5-{5-[(exo)-8-Azabicyclo[3.2.1]octan-3-yloxy]pyridin-2-yl}-1H-indole bis(hydrochloric acid)

The product of Example 63B (0.25 g, 0.79 mmol) was treated with HCl (Aldrich, 4 M in dioxane, 0.5 mL, 2.0 mmol) in EtOAc/EtOH (v. 10/1, 10 mL). The precipitated solid was filtered and dried to give the title compound (0.20 g, yield, 64.9%). $^1$H NMR (300 MHz, CD$_3$OD) δ 1.94-2.13 (m, 2H), 2.12-2.35 (m, 4H), 2.42-2.68 (m, 2H), 4.09-4.37 (m, 2H), 5.05-5.28 (m, 1H), 6.67 (d, J=3.39 Hz, 1H), 7.43 (d, J=3.05 Hz, 1H), 7.57-7.72 (m, 2H), 8.16 (s, 1H), 8.27-8.39 (m, 2H), 8.52 (d, J=2.37 Hz, 1H) ppm; MS (DCI/NH$_3$) m/z 320 (M+H)$^+$. Anal. Calc. for C$_{20}$H$_{21}$N$_3$O.2.00HCl.0.90H$_2$O: C, 58.80; H, 6.12; N, 10.29. Found: C, 58.50; H, 5.86; N, 10.08

EXAMPLE 64

5-{5-[(endo)-8-Azabicyclo[3.2.1]octan-3-yloxy]pyridin-2-yl}indolin-2-one

The product of Example 59A (119 mg, 0.50 mmol), was coupled with the product of Example 58A (194 mg, 0.75 mmol) according to the procedure of Example 9B. to provide the title compound (150 mg, yield, 89.0%). $^1$H NMR (300 MHz, DMSO-D$_6$) δ 1.86-2.42 (m, 8H), 3.54 (s, 2H), 3.89-4.06 (m, 2H), 4.83 (t, J=4.07 Hz, 1H), 6.88 (d, J=7.80 Hz, 1H), 7.47 (dd, J=8.82, 3.05 Hz, 1H), 7.78-7.94 (m, 3H), 8.32 (d, J=2.71 Hz, 1H), 10.50 (s, 1H) ppm; MS (DCI/NH$_3$) m/z 336 (M+H)$^+$.

EXAMPLE 65

5-{5-[(endo)-8-Azabicyclo[3.2.1]octan-3-yloxy]pyridin-2-yl}-1H-pyrrolo[2,3-b]pyridine The product of Example 59A (200 mg, 0.80 mmol), was coupled with the product of Example 47A (183 mg, 0.75 mmol) according to the procedure of Example 9B. to provide the title compound (80 mg, yield, 49.9%). $^1$H NMR (300 MHz, DMSO-D$_6$) δ 1.89-2.16 (m, 4H), 2.17-2.40 (m, 4H), 3.78-4.26 (m, 2H), 4.86 (t, J=4.24 Hz, 1H), 6.51 (dd, J=3.39, 1.70 Hz, 1H), 7.46-7.58 (m, 2H), 7.97 (d, J=8.82 Hz, 1H), 8.39 (d, J=2.71 Hz, 1H), 8.52 (d, J=2.03 Hz, 1H), 8.88 (d, J=2.03 Hz, 1H), 11.70 (s, 1H) ppm; MS (DCI/NH$_3$) m/z 321 (M+H)$^+$.

EXAMPLE 66

5-{5-[(exo)-8-Azabicyclo[3.2.1]octan-3-yloxy]pyridin-2-yl}-1H-pyrrolo[2,3-b]pyridine The product of Example 63A (200 mg, 0.80 mmol) was coupled with the product of Example 47A (183 mg, 0.75 mmol) according to the procedure of Example 9B. to provide the title compound (120 mg, yield, 74.9%). $^1$H NMR (300 MHz, DMSO-D$_6$) δ 1.82-2.18 (m, 6H), 2.18-2.40 (m, 2H), 3.91-4.30 (m, 2H), 4.71-5.30 (m, 1H), 6.51 (dd, J=3.39, 1.70 Hz, 1H), 7.47-7.55 (m, 1H), 7.61 (dd, J=8.82, 3.05 Hz, 1H), 7.94 (d, J=8.82 Hz, 1H), 8.42 (d, J=2.71 Hz, 1H), 8.52 (d, J=2.03 Hz, 1H), 8.88 (d, J=2.03 Hz, 1H), 11.71 (s, 1H) ppm; MS (DCI/NH$_3$) m/z 321 (M+H)$^+$.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracistemally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, dissolving or suspending the drug in an oil vehicle can administer a parenterally administered drug form.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethyl-cellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, fumarate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl trifilate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Determination of Biological Activity

To determine the effectiveness of representative compounds of this invention as α7 nAChRs, the compounds of the invention were evaluated according to the [$^3$H]-DPPB binding or the [$^3$H]-methyllycaconitine (MLA) binding assay (both measures of α7 NNR binding) and considering the [$^3$H]-cytisine binding assay (measure of α4β2 interactions), which were performed as described below.

[$^3$H]-Cytisine Binding

Binding conditions were modified from the procedures described in Pabreza L A, Dhawan, S, Kellar K J, [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM $CaCl_2$/2 mM $MgCl_2$/50 mM Tris-Cl, pH 7.4, 4° C.). Samples containing 100-200 μg of protein and 0.75 nM [3H]-cytisine (30 $C_i$/mmol; Perkin Elmer/NEN Life Science Products, Boston, Mass.) were incubated in a final volume of 500 μL for 75 minutes at 4° C. Seven log-dilution concentrations of each compound were tested in duplicate. Non-specific binding was determined in the presence of 10 μM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM $CaCl_2$/2 mM $MgCl_2$). Packard MicroScint-20® scintillation cocktail (40 μL) was added to each well and radioactivity determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/1+[Ligand]/K_D]$.

[$^3$H]-Methyllycaconitine (MLA) Binding

Binding conditions were similar to those for [3H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM $CaCl_2$, 2 mM $MgCl_2$, and 50 mM Tris-Cl, pH 7.4, 22° C.). Samples containing 100-200 μg of protein, 5 nM [3H]-MLA (25 $C_i$/mmol; Perkin Elmer/NEN Life Science Products, Boston, Mass.) and 0.1% bovine serum albumin (BSA, Millipore, Bedford, Mass.) were incubated in a final volume of 500 μL for 60 minutes at 22° C. Seven log-dilution concentrations of each compound were tested in duplicate. Non-specific binding was determined in the presence of 10 μM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20® scintillation cocktail (40 μL) was added to each well and radioactivity was determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/1+[Ligand]/K_D]$.

[$^3$H]-DPPB Binding

[$^3$H]-DPPB, [$^3$H]-(S,S)-2,2-dimethyl-5-(6-phenyl-pyridazin-3-yl)-5-aza-2-azonia-bicyclo[2.2.1]heptane iodide, binding to the α7 nAChR subtype was determined using membrane enriched fractions from rat brain minus cerebellum or human cortex (ABS Inc., Wilmington, Del.). Pellets were thawed at 4° C., washed and resuspended with a Polytron at a setting of 7 in 30 volumes of BSS-Tris buffer (120 mM NaCl, 5 mM KCl, 2 mM CaCl$_2$, 2 mM MgCl$_2$, and 50 mM Tris-Cl, pH 7.4, 4° C.). Seven log-dilution concentrations of test compounds containing 100-200 µg of protein, and 0.5 nM [$^3$H]-DPPB (62.8 Ci/mmol; R46V, Abbott Labs) were incubated in a final volume of 500 µl for 75 minutes at 4° C. in duplicate. Non-specific binding was determined in the presence of 10 µM methyllycaconitine. Bound radioactivity was collected on Millipore MultiScreen® harvest plates FB presoaked with 0.3% PEI using a Packard cell harvester, washed with 2.5 ml ice-cold buffer, and radioactivity was determined using a Packard TopCount Microplate beta counter. IC$_{50}$ values were determined by nonlinear regression in Microsoft® Excel or Assay Explorer. K$_i$ values were calculated from the IC$_{50}$s using the Cheng-Prusoff equation, where K$_i$=IC$_{50}$/1+[Ligand]/K$_D$]. [$^3$H]-DPPB was obtained according to the preparation procedures described below.

[Methyl-$^3$H]2,2-Dimethyl-5-(6-phenyl-pyridazin-3-yl)-5-aza-2-azonia-bicyclo[2.2.1]heptane; iodide Preparation

[Methyl-$^3$H]2,2-dimethyl-5-(6-phenyl-pyridazin-3-yl)-5-aza-2-azonia-bicyclo[2.2.1]heptane; iodide used in the [$^3$H]-DPPB binding assay above was prepared according to the following procedures.

Step 1: Preparation of t-Butyl (S,S)-5-(6-Phenyl-pyridazin-3-yl)-2,5-diazabicyclo [2.2.1]heptane-2-carboxylate Triethylamine (20 mL) was added to a suspension of t-butyl (S,S)-2,5-diazabicyclo[2.2.1]heptane-2-carboxylate (3.43 g, 17.3 mmol, Aldrich Chemical Company) and 3-chloro-6-phenylpyridazine (3.30 g, 17.3 mmol, Aldrich Chemical Company) in toluene (50 mL) and the mixture was heated under nitrogen at 100° C. for 7 days. The dark mixture was cooled to room temperature, and the resulting precipitate was isolated by filtration, washed with toluene (15 mL) and dried under vacuum to provide the title compound as an off-white solid (3.00 g). The filtrate was concentrated and the residue wa purified by column chromatography on silica gel, eluting with ethyl acetate, to provide additional product (0.41 g, total yield 3.41 g, 56%): MS (DCI/NH3) m/z 353 (M+H)+.

Step 2: Preparation of (S,S)-2-Methyl 5-(6-phenyl-pyridazin-3-yl)-2,5-diazabicyclo[2.2.1]heptane The product obtained from Step 1 (3.41 g, 9.7 mmol) was dissolved in formic acid (20 mL) and treated with formalin (37% by weight, 1.0 g, 12.3 mmol). The mixture was heated at 100° C. for 1 h, and the brown solution was cooled to room temperature and concentrated under vacuum. The residue was purified by column chromatography on silica gel, eluting with CH2Cl2—CH3OH—NH4OH (95:5:1) to provide the title compound as an off-white solid (2.50 g, 96%): MS (DCI/NH3) m/z 267 (M+H)+.

Step 3: Preparation of [$^3$H]-(S,S)-2,2-Dimethyl-5-(6-phenyl-pyridazin-3-yl)-5-aza-2-azonia-bicyclo[2.2.1] heptane iodide ([$^3$H]-DPPB)

[$^3$H]Methyl iodide in toluene (250 mCi in 0.1 mL, 85 Ci/mmol, American Radiolabeled Chemicals, Inc.) was combined with a solution of the product obtained from Step 2 in dichloromethane (0.788 mg, 2.96 mmole in 0.45 mL). The vial was capped and the mixture was allowed to react overnight at room temperature. Methanol was added and the solvents were evaporated to give 42 mCi. The product was taken up in methanol for HPLC purification.

Step 4: Purification by High Performance Liquid Chromatography (HPLC)

About 7 mCi of [$^3$H]-DPPB was evaporated to dryness and the residue was dissolved in total about 4.5 ml acetonitrile:water:TFA (15:85:0.1). Approximately 0.9 mL per injection were made onto a Phenomenex Luna C18(2) column (5 micron, 250 mm×4.6 mm ID) using an Agilent HPLC system. [3H]-DPPB was eluted by a gradient mobile phase from 10% B to 20% B in 20 min where Mobile Phase A=0.1% trifluoroacetic acid in water and Mobile Phase B=0.1% trifluoroacetic acid in acetonitrile at a flow rate of approximately 1 mL/min. Peak detection and chromatograms were obtained with an Agilent variable wavelength UV detector set at 275 nm. The fractions containing [$^3$H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.

Step 5: Determination of Purity and Specific Activity

[$^3$H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 mL flow cell and a 3:1 ratio of Ultima-Flo M scintillation cocktail to HPLC mobile phase were used. The analyses were performed using a Phenomenex Luna C$^{18}$(2) column (5 microns, 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/min and the UV detection was set at 275 nm.

The radiochemical purity of [$^3$H]-DPPB was found to be >98%. The specific activity was determined to be 62.78 Ci/mmol by mass spectroscopy.

Compounds of the invention had K$_i$ values of from about 1 nanomolar to about 10 micromolar when tested by the [$^3$H]-MLA assay, many having a K$_i$ of less than 1 micromolar. [$^3$H]-Cytisine binding values of compounds of the invention ranged from about 1 nanomolar to at least 100 micromolar. Alternatively, the K$_i$ value as measured by [$^3$H]-DPPB assay can be used in place of the K$_{iMLA}$.

Methods of the Invention

Compounds and compositions of the invention are useful for modulating the effects of nAChRs, and more particularly α7 nAChRs. In particular, the compounds and compositions of the invention can be used for treating and preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen. Also, some compounds of the invention possess affinity at the α4β2 nAChRs in addition to α7 nAChRs, and selective compounds with dual affinities at both receptor subtypes also are expected to have beneficial effects.

The compounds of the invention, including but not limited to those specified in the examples, possess an affinity for nAChRs, and more particularly α7 nAChRs. As α7 nAChRs ligands, the compounds of the invention can be useful for the treatment and prevention of a number of α7 nAChR-mediated diseases or conditions.

For example, α7 nAChRs have been shown to play a significant role in enhancing cognitive function, including aspects of learning, memory and attention (Levin, E. D., J. Neurobiol. 53: 633-640, 2002). As such, α7 ligands are suitable for the treatment of cognitive disorders including, for example, attention deficit disorder, attention deficit hyperactivity disorder (ADHD), Alzheimer's disease (AD), mild cognitive impairment, senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the neuroprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734-4739, 2001). The activation of α7 nAChRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

Schizophrenia is a complex disease that is characterized by abnormalities in perception, cognition, and emotions. Significant evidence implicates the involvement of α7 nAChRs in this disease, including a measured deficit of these receptors in post-mortem patients (Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). Thus, α7 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833-839, 2001). Improved angiogenesis has been shown to involve activation of the α7 nAChR (Heeschen, C. et al, J. Clin. Invest. 110: 527-536, 2002). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin, M. and Changeux, J.-P. PNAS 98:2803-2807, 2001). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384-388, 2003). Therefore, selective α7 ligands demonstrate potential for treating conditions involving TNF-mediated diseases, for example, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reproduct. 68: 1348-1353 2003). Consequently, selective α7 agents demonstrate utility for treating fertility disorders.

Compounds of the invention are particularly useful for treating and preventing a condition or disorder affecting cognition, neurodegeneration, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.010 mg/kg body weight to about 1 g/kg body weight. More preferable doses can be in the range of from about 0.010 mg/kg body weight to about 100 mg/kg body weight. If desired, the effective daily dose can be divided into multiple doses for purposes of administration. Consequently, single dose compositions may contain such amounts or submultiples thereof to make up the daily dose.

Compounds of the invention are α7 nAChRs ligands that modulate function of α7 nAChRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor. Binding to α7 receptor also trigger key signaling processes involving various kinases and phosphatases and protein-protein interactions that are important to effects on memory, cytoprotection, gene transcription and disease modification. Therefore, the administration of a therapeutically effective amount of a compound of formula (I) to a mammal provides a method of selectively modulating the effects of α4β2, α7, or both α4β2 and α7 nicotinic acetylcholine receptors.

Furthermore, the administration of a therapeutically effective amount of a compound of formula (I) to a mammal provides a method of treating or preventing a condition or disorder selected from the group consisting of attention deficit disorder, attention deficit hyperactivity disorder (ADHD), Alzheimer's disease (AD), mild cognitive impairment, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, need for new blood vessel growth associated with wound healing, need for new blood vessel growth associated with vascularization of skin grafts, and lack of circulation, more particularly circulation around a vascular occlusion, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis. More preferred, the administration of a therapeutically effective amount of a compound of formula (I) to a mammal provides a method of treating cognitive disorders, neurodegeneration, and schizophrenia. Furthermore, compounds of formula (I) may also be administered in combination with an atypical antipsychotic.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods of use of the invention, may be made without departing from the spirit and scope thereof.

What is claimed is:

1. The compound of formula (I),

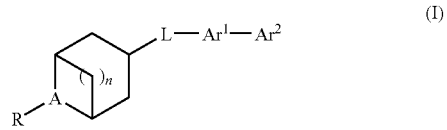

(I)

or a pharmaceutically acceptable salt, ester, amide, or prodrug thereof, wherein n is 1, 2 or 3;

A is N or $N^+$—$O^-$;

R is hydrogen, alkyl, cycloalkylalkyl and arylalkyl;

L is selected from the group consisting of O, S, and —N($R_a$)—;

$Ar^1$ is a pyridinylene group substituted with 0, 1, 2 or 3 substituents selected from the group consisting of acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —$NR_gR_j$, ($NR_gR_j$)alkyl, ($NR_gR_j$)alkoxy, ($NR_gR_j$)carbonyl, and ($NR_gR_j$)sulfonyl, wherein $R_g$ and $R_j$ are each independently selected from the group consisting of hydrogen and alkyl; and $Ar^2$ is a bicyclic heteroaryl substituted with 0, 1, 2, or 3 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —$NR_gR_j$, ($NR_gR_j$)alkyl, ($NR_gR_j$)alkoxy, ($NR_gR_j$)carbonyl, and ($NR_gR_j$)sulfonyl, wherein $R_g$ and $R_j$ are each independently selected from the group consisting of hydrogen and alkyl; and $R_a$ is selected from the group consisting of hydrogen, alkyl and alkylcarbonyl.

2. The compound of claim 1, wherein $Ar^1$ is selected from the group consisting of:

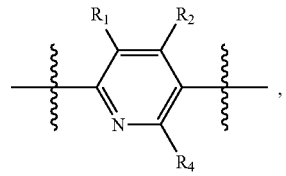

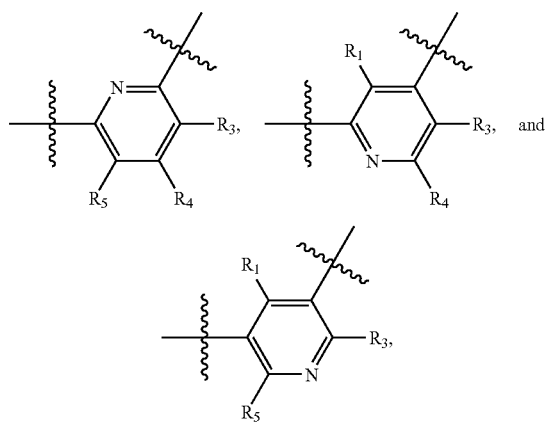

wherein $R_1$, $R_2$, $R_3$, $R_4$ and $R_5$ are independently selected from the group consisting of acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —$NR_gR_j$, ($NR_gR_j$)alkyl, ($NR_gR_j$)alkoxy, ($NR_gR_j$)carbonyl, and ($NR_gR_j$)sulfonyl;

$R_g$ and $R_j$ are each independently selected from the group consisting of hydrogen and alkyl.

3. The compound of claim 1, wherein $Ar^2$ is selected from the group consisting of

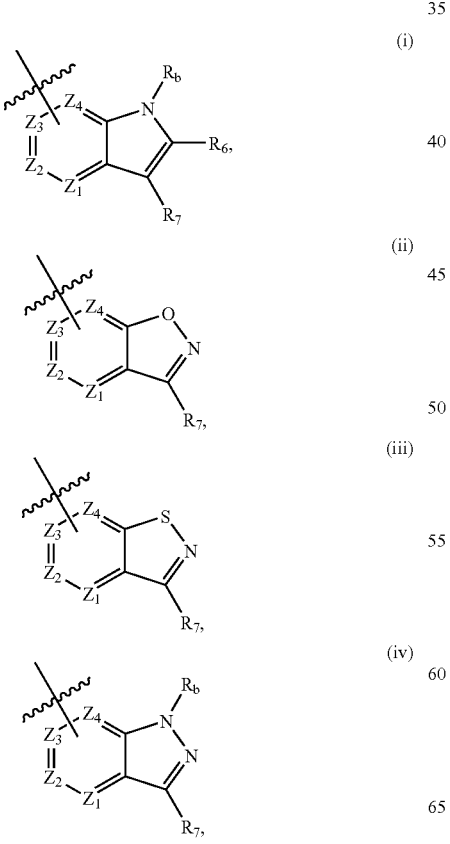

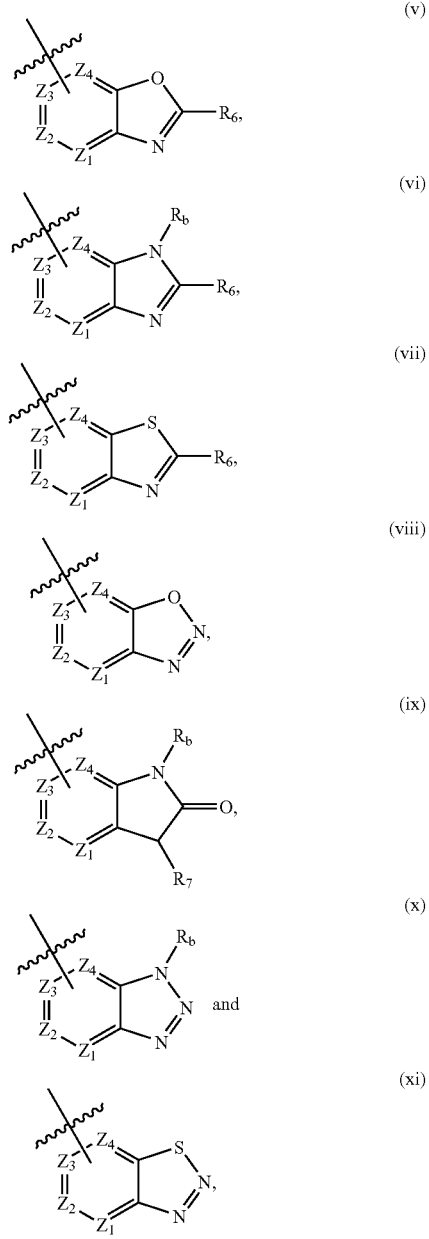

wherein $Z_1$, $Z_2$, $Z_3$ and $Z_4$ are each independently nitrogen or are carbon, wherein the carbon atom is optionally substituted with a substituent selected from the group consisting of hydrogen, halogen, alkyl, —$OR_c$, -alkyl-$OR_c$, —$NR_dR_e$, and -alkyl-$NR_dR_e$;

$R_b$ is selected from the group consisting of hydrogen, alkyl and alkylcarbonyl;

$R_c$ is alkyl;

$R_d$ and $R_e$ are each independently selected from the group consisting of hydrogen and alkyl, $R_6$ and $R_7$ are each independently selected from the group consisting of hydrogen, alkenyl, alkoxy, alkoxyalkoxy, alkoxyalkyl, alkoxycarbonyl, alkoxyimino, alkoxysulfonyl, alkyl, alkylcarbonyl, alkylcarbonyloxy, alkylsulfonyl, alkynyl, carboxy, cyano, formyl, haloalkoxy, haloalkyl, halo, hydrogen, hydroxy, hydroxyalkyl, mercapto, nitro, thioalkoxy, —$NR_gR_j$, ($NR_gR_j$)alkyl, (NR$_g$R$_j$)alkoxy, (NR$_g$R$_j$)carbonyl, and (NR$_g$R$_j$)sulfonyl; R$_g$ and R$_j$ are each independently selected from the group consisting of hydrogen and alkyl.

4. The compound of claim 2, wherein

A is N; R is methyl or hydrogen; L is O; n is 2; and Ar$^2$ is selected from the group of consisting of:

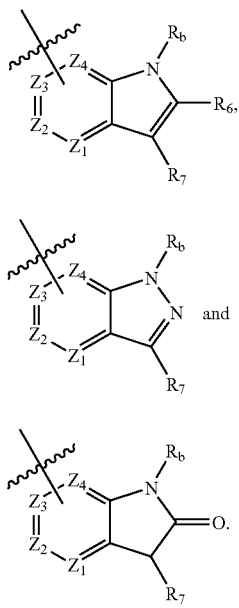

5. The compound of claim 2, wherein

A is N; R is methyl or hydrogen; L is O; n is 2; Ar$^1$ is

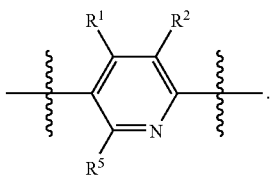

6. The compound of claim 2, wherein

A is N; R is methyl or hydrogen; L is O; n is 2; Ar$^1$ is

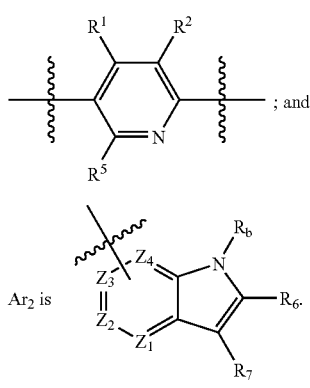

7. The compound of claim 1, selected from the group consisting of:

5-{5-[(endo)-8-methyl-8-aza-bicyclo[3.2.1]oct-3-yloxy]-pyridin-2-yl}-1H-indole;
(endo)-3-(6-benzo[b]thiophen-5-yl-pyridin-3-yloxy)-8-methyl-8-aza-bicyclo[3.2.1]octane;
5-{5-[(exo)-8-methyl-8-aza-bicyclo[3.2.1]oct-3-yloxy]-pyridin-2-yl}-1H-indole;
(exo)-3-[6-(benzofuran-5-yl)-pyridin-3-yloxy]-8-methyl-8-aza-bicyclo[3.2.1]octane;
5-{5-[(exo)-8-methyl-8-aza-bicyclo[3.2.1]oct-3-yloxy]-pyridin-2-yl}-1H-indazole;
5-{5-[(exo)-8-methyl-8-aza-bicyclo[3.2.1]oct-3-yloxy]-pyridin-2-yl}-2-trifluoromethyl-1H-indole;
4-{5-[(exo)-8-methyl-8-aza-bicyclo[3.2.1]oct-3-yloxy]-pyridin-2-yl}-1H-indole;
5-{6-[(endo)-8-methyl-8-aza-bicyclo[3.2.1]oct-3-yloxy]-pyridin-3-yl}-1H-indole;
(endo)-3-(5-benzo[b]thiophen-5-yl-pyridin-2-yloxy)-8-methyl-8-aza-bicyclo[3.2.1]octane;
5-{6-[(exo)-8-methyl-8-aza-bicyclo[3.2.1]oct-3-yloxy]-pyridin-3-yl}-1H-indole;
[6-(1H-indol-5-yl)-pyridin-3-yl]-[(endo-8-methyl-8-aza-bicyclo[3.2.1]oct-3-yl]-amine;
[6-(benzofuran-5-yl)-pyridin-3-yl]-[(endo)-8-methyl-8-aza-bicyclo[3.2.1]oct-3-yl]-amine;
[(endo)-8-methyl-8-aza-bicyclo[3.2.1]oct-3-yl]-[6-(2-trifluoromethyl-1H-indol-5-yl)-pyridin-3-yl]-amine;
[6-(1H-indazol-5-yl)-pyridin-3-yl]-[(endo)-8-methyl-8-aza-bicyclo[3.2.1]oct-3-yl]-amine;
[6-(1H-indol-4-yl)-pyridin-3-yl]-[(endo)-8-methyl-8-aza-bicyclo[3.2.1]oct-3-yl]-amine;
[(endo)-8-aza-bicyclo[3.2.1]oct-3-yl]-[6-(1H-indol-5-yl)-pyridin-3-yl]-amine;
[6-(1H-indol-6-yl)-pyridin-3-yl]-[(endo)-8-methyl-8-aza-bicyclo[3.2.1]oct-3-yl]-amine;
5-{5-[(exo)-8-methyl-8-aza-bicyclo[3.2.1]oct-3-yloxy]-pyridin-2-yl}-1H-pyrrolo[2,3-b]pyridine;
5-{5-[(exo)-8-methyl-8-aza-bicyclo[3.2.1]oct-3-yloxy]-pyridin-3-yl}-1H-indole;
(endo)-N-(5-(1H-Indol-5-yl)pyridin-3-yl)-8-methyl-8-azabicyclo[3.2.1]octan-3-amine;
(endo)-N-(5-(1H-Indol-4-yl)pyridin-3-yl)-8-methyl-8-azabicyclo[3.2.1]octan-3-amine;
(endo)-N-(5-(1H-Indol-6-yl)pyridin-3-yl)-8-methyl-8-azabicyclo[3.2.1]octan-3-amine;
(endo)-N-{5-[2-(trifluoromethyl)-1H-indol-5-yl]pyridin-3-yl}-8-Methyl-8-azabicyclo[3.2.1]octan-3-amine;
5-{5-[(endo)-8-Methyl-8-azabicyclo[3.2.1]octan-3-yloxy]pyridin-2-yl}-1H-pyrrolo[2,3-b]pyridine;
5-{5-[(endo)-8-Methyl-8-azabicyclo[3.2.1]octan-3-yloxy]pyridin-2-yl}indolin-2-one;
5-{5-[(endo)-8-Azabicyclo[3.2.1]octan-3-yloxy]pyridin-2-yl}-1H-indole;
(1R,3r,5S,8s)-3-(6-(1H-Indol-5-yl)pyridin-3-yloxy)-8-methyl-8-azabicyclo[3.2.1]octane 8-oxide;
(1R,3r,5S,8r)-3-(6-(1H-Indol-5-yl)pyridin-3-yloxy)-8-methyl-8-azabicyclo[3.2.1]octane 8-oxide;
4-{5-[(endo)-8-Azabicyclo[3.2.1]octan-3-yloxy]pyridin-2-yl}-1H-indole;
5-{5-[(exo)-8-Azabicyclo[3.2.1]octan-3-yloxy]pyridin-2-yl}-1H-indole;
5-{5-[(endo)-8-Azabicyclo[3.2.1]octan-3-yloxy]pyridin-2-yl}indolin-2-one;
5-{5-[(endo)-8-Azabicyclo[3.2.1]octan-3-yloxy]pyridin-2-yl}-1H-pyrrolo[2,3-b]pyridine;

5-{5-[(exo)-8-Azabicyclo[3.2.1]octan-3-yloxy]pyridin-2-yl}-1H-pyrrolo[2,3-b]pyridine.

8. A pharmaceutical composition comprising a therapeutically effective amount of a compound of claim 1 in combination with a pharmaceutically acceptable carrier.

9. A compound that is 5-{5-[(endo)-8-Azabicyclo[3.2.1]octan-3-yloxy]pyridin-2-yl}-1H-indole or a salt thereof.

10. A compound that is 5-{5-[(exo)-8-Azabicyclo[3.2.1]octan-3-yloxy]pyridin-2-yl}-1H-indole or a salt thereof.

11. A compound that is 5-{5-[(endo)-8-methyl-8-aza-bicyclo[3.2.1]oct-3-yloxyl]-pyridin-2-yl}-1H-indole or a salt thereof.

12. A compound that is 5-{5-[(exo)-8-methyl-8-aza-bicyclo[3.2.1]oct-3-yloxy]-pyridin-2-yl}-1H-indole or a salt thereof.

13. A compound that is 4-{5-[(exo)-8-methyl-8-aza-bicyclo[3.2.1]oct-3-yloxy]-pyridin-2-yl}-1H-indole or a salt thereof.

14. A compound that is 5-{6-[(endo)-8-methyl-8-aza-bicyclo[3.2.1]oct-3-yloxy]-pyridin-3-yl}-1H-indole or a salt thereof.

* * * * *

UNITED STATES PATENT AND TRADEMARK OFFICE
CERTIFICATE OF CORRECTION

PATENT NO. : 7,872,017 B2  Page 1 of 1
APPLICATION NO. : 11/748527
DATED : January 18, 2011
INVENTOR(S) : Ji et al.

It is certified that error appears in the above-identified patent and that said Letters Patent is hereby corrected as shown below:

Claims:

Column 75 Line 8 - After " 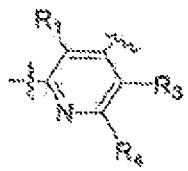 " Delete "and"

Column 75 Approx. Line 20 - After " 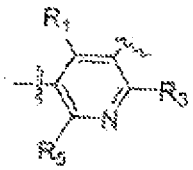 "

Insert -- 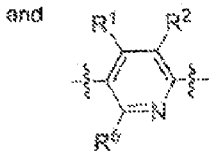 --

Signed and Sealed this
Twenty-fifth Day of December, 2012

David J. Kappos
*Director of the United States Patent and Trademark Office*